United States Patent
Macneil et al.

(10) Patent No.: US 10,561,369 B2
(45) Date of Patent: Feb. 18, 2020

(54) SYSTEM AND METHOD TO IDENTIFY REMOTE SOURCES ASSOCIATED WITH A BIOLOGICAL RHYTHM DISORDER

(71) Applicant: Topera, Inc., Santa Clara, CA (US)

(72) Inventors: William Robert Macneil, Oakville, MO (US); Ruchir Sehra, Scottsdale, AZ (US)

(73) Assignee: Topera, Inc., Santa Clara, CA (US)

( * ) Notice: Subject to any disclaimer, the term of this patent is extended or adjusted under 35 U.S.C. 154(b) by 32 days.

(21) Appl. No.: 15/587,913

(22) Filed: May 5, 2017

(65) Prior Publication Data

US 2017/0332971 A1    Nov. 23, 2017

Related U.S. Application Data

(60) Provisional application No. 62/338,177, filed on May 18, 2016.

(51) Int. Cl.
    *A61B 5/00*      (2006.01)
    *A61B 5/11*      (2006.01)
    (Continued)

(52) U.S. Cl.
    CPC ........ *A61B 5/6859* (2013.01); *A61B 5/02405* (2013.01); *A61B 5/1102* (2013.01);
    (Continued)

(58) Field of Classification Search
CPC ... A61B 5/0422; A61B 5/1102; A61B 5/6859; A61B 5/7282
See application file for complete search history.

(56) References Cited

U.S. PATENT DOCUMENTS

| | | |
|---|---|---|
| 2013/0006131 A1 | 1/2013 | Narayan et al. |
| 2014/0276152 A1* | 9/2014 | Narayan .............. A61B 5/0006 600/508 |

(Continued)

FOREIGN PATENT DOCUMENTS

WO    WO2015130829 A1    9/2015

OTHER PUBLICATIONS

Search Report and Written Opinion issued in International Application No. PCT/US2017/031304 dated Jul. 25, 2017.

*Primary Examiner* — William J Levicky
(74) *Attorney, Agent, or Firm* — Hoffmann & Barron, LLP

(57) ABSTRACT

A system to generate a representation of a rhythm disorder that includes identifying remote or polar sources associated with a cardiac rhythm disorder is disclosed. The system includes generating a representation based on the cardiac information signals received from the sensors by transformation of spline-sensor locations of the catheter to x-y coordinate pairs of locations. A first offset is determined resulting from a perturbation to corresponding x-y coordinate pairs of locations associated with the representation, the first offset displacing coordinate pairs of sensor locations of the representation at least one unit of displacement in a first direction. A remote source associated with a cardiac rhythm disorder is identified when activations associated with the cardiac information signals rotate in sequence at least once, or emanate centrifugally for at least a first time period, the source being identified based on the representation as displaced.

A corresponding method and computer-readable medium are also disclosed.

35 Claims, 39 Drawing Sheets

(51) Int. Cl.
*A61B 5/042* (2006.01)
*A61B 5/024* (2006.01)

(52) U.S. Cl.
CPC .......... *A61B 5/7278* (2013.01); *A61B 5/7282* (2013.01); *A61B 5/742* (2013.01)

(56) References Cited

U.S. PATENT DOCUMENTS

| | | |
|---|---|---|
| 2014/0276157 A1 | 9/2014 | Macneil et al. |
| 2014/0371609 A1* | 12/2014 | Narayan .............. A61B 5/0006 600/508 |
| 2015/0133760 A1 | 5/2015 | Kordis et al. |
| 2016/0015283 A1 | 1/2016 | Narayan et al. |

* cited by examiner

Basket Catheter Splines and Electrodes

Spline A of Basket Facing Tricuspid Valve in Right Atrium

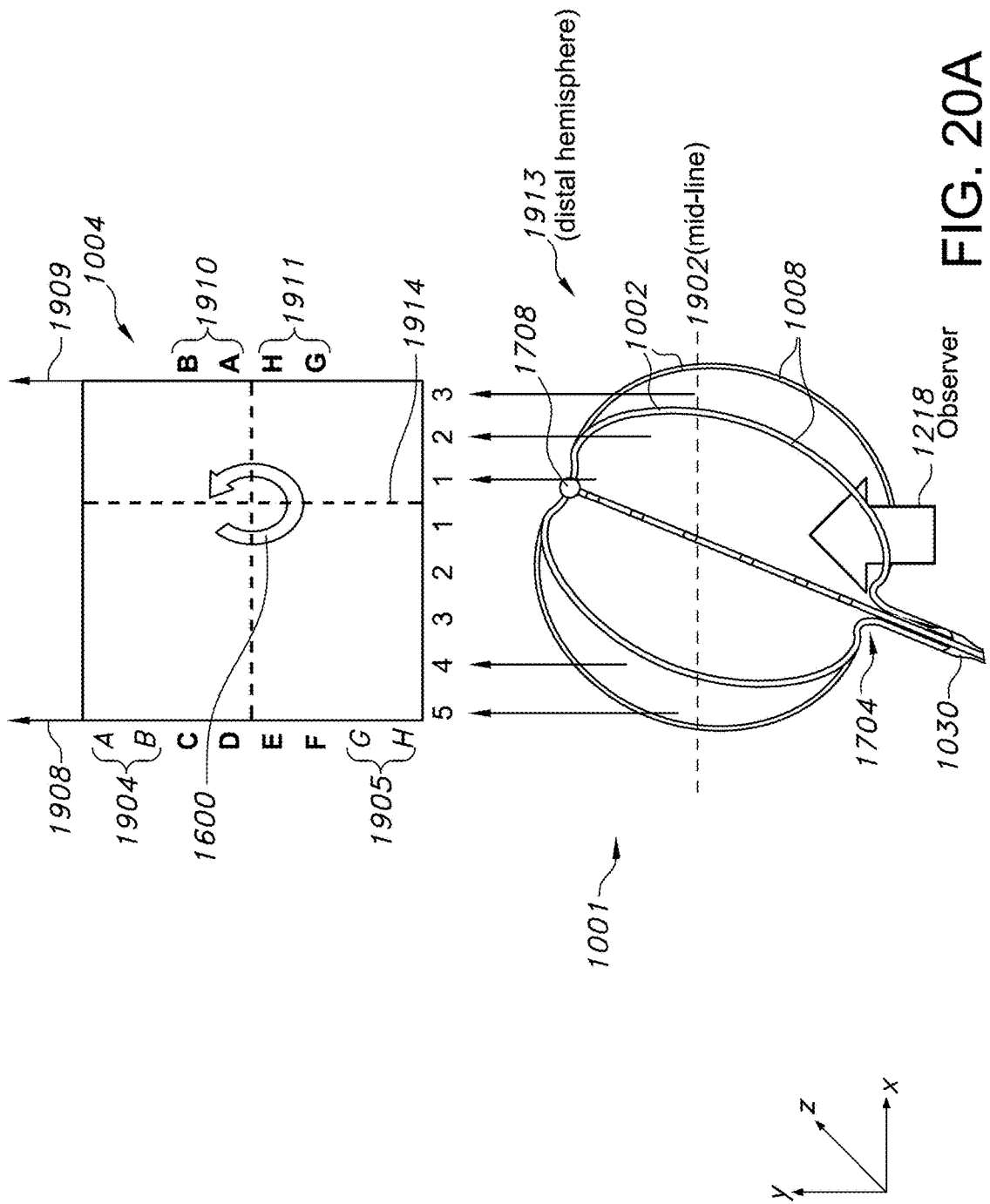

SYSTEM AND METHOD TO IDENTIFY REMOTE SOURCES ASSOCIATED WITH A BIOLOGICAL RHYTHM DISORDER

CROSS-REFERENCE TO RELATED APPLICATION

The present application claims the benefit of U.S. Provisional Application No. 62/338,177, filed on May 18, 2016, the specification of which is incorporated by reference herein in its entirety for all purposes.

FIELD OF THE DISCLOSURE

The present application relates generally to biological rhythm disorders. More specifically, the present application is directed to a system and method to identify a source including polar sources and/or remotely located sources in relation to a catheter and/or sensors of a catheter, the sources associated with a biological rhythm disorder, such as a heart rhythm disorder.

BACKGROUND

Brief Discussion of Related Art

Heart (cardiac) rhythm disorders are common and represent significant causes of morbidity and death throughout the world. Malfunction of the electrical system in the heart represents a proximate cause of heart rhythm disorders. Heart rhythm disorders exist in many forms, of which the most complex and difficult to treat are atrial fibrillation (AF), ventricular tachycardia (VT) and ventricular fibrillation (VF). Other rhythm disorders are more simple to treat, but may also be clinically significant including atrial tachycardia (AT), supraventricular tachycardia (SVT), atrial flutter (AFL), supraventricular ectopic complexes/beats (SVE) and premature ventricular complexes/beats (PVC).

Previously, treatment of heart rhythm disorders—particularly complex rhythm disorders of AF, VF and polymorphic VT—has been difficult because the location in the heart that harbors the source of the heart rhythm disorder could not be identified. There have been various theories of how complex rhythm disorders function and clinical applications for treating these complex rhythm disorders. However, none of the applications proved fruitful in the treatment of complex rhythm disorders.

Recently, there has been a breakthrough discovery that for the first time identified sources associated with complex heart rhythm disorders. This technological breakthrough successfully reconstructed cardiac activation information (onset times) in signals obtained from electrodes of catheters introduced into patients' heart to identify rotational activation patterns (rotational sources), centrifugal activations or other centrifugal propagation (focal sources) that cause a large percentage of the heart rhythm disorders worldwide. Treatment of the heart rhythm disorders including complex rhythm disorders can thus be targeted to the rotational sources in the patients' heart to eliminate the heart rhythm disorders. Such treatment can be successfully delivered by ablation, for example.

While a rotational source of a complex heart rhythm disorder can be identified as described above, the identification of a rotational source in a polar or remote region of the heart relative to the position of the catheter as delivered into the organ of the patient, and the determination of the likely location of the rotational source in the patient's organ have not been identified. In some instances, two or more rotational sources may be continuously rotating in a patient's heart. While, the rotational sources may be apparent if the sources are not remotely located, it is not known how to discern, locate and identify these rotors that exist in polar and/or remote regions relative to the catheter and/or its location and further, relative to sensors of a catheter, not readily discernible on a grid representation of the cardiac information signals.

There are no known systems or methods to determine the approximate location of a remote and/or polar rotational, centrifugal or focal source(s) associated with a heart rhythm disorder, relative to a catheter and/or sensors, including the approximate rotational path of a processing rotational source as associated with a complex cardiac rhythm disorder.

SUMMARY

The present disclosure is applicable to various rhythm disorders, including heart rhythm disorders, as well as other biological rhythm disorders, such as neurological seizures, esophageal spasms, bladder instability, irritable bowel syndrome, and other biological disorders for which biological activation information and/or focal sources have been reconstructed to permit determination, diagnosis, and/or treatment of a rotational source causing the biological rhythm disorders. It is particularly useful, however, in complex rhythm disorders of the heart, in order to find the location of the rotational sources of the disorders such that they can be treated with precision and expediency.

Among the advantages of the present disclosure is the ability to use reconstructed cardiac (or biological) activation information associated with rotational, centrifugal arrangements or focal sources of the rhythm disorder, such that a determination of the location of the rotational, centrifugal arrangement or focal source including a remotely located rotational, centrifugal or focal source can be identified and subsequently treated with precision.

Another advantage is identifying the location of sources associated with complex cardiac rhythm disorders. Treatment of the heart rhythm disorders can thus be targeted to these rotational or focal sources in the patient's heart in order to eliminate these complex cardiac rhythm disorders. As an example, such treatment can be successfully targeted with greater precision and delivered by ablation.

Another advantage is that the present invention provides a system and a method, which can be carried out rapidly while a sensing device—such as a catheter having sensors thereon—is used in or near the patient and can be followed by treatment of cardiac tissue to ameliorate the rhythm disorder and in many cases cure the rhythm disorder. Treatment may thus occur immediately upon computing the likely location of the source of the rhythm disorder, since it will provide the location in the patient of the continuous source that is sustaining, or driving, the rhythm disorder even if remotely located in an otherwise undetectable region of the heart.

Still another advantage of the present disclosure is that precise identification of the location of a remotely located rotational source or polar source, can help eliminate the heart rhythm disorder including complex cardiac rhythm disorders, while also helping to limit or spare the destruction of otherwise healthy heart tissue of the patient that may only insignificantly contribute to driving the source of the heart rhythm disorder.

As used herein, reconstructed activation information is signal data of cardiac or biological signals each of which has been processed to identify activation onset times at a sensor location distinct from nearby or adjacent sensor locations for one or more beats of a biological or cardiac rhythm disorder.

As used herein, activation onset time is a time point at which activation commences in a cell or tissue of a patient, as opposed to other time points during activation.

As used herein, activation is a process whereby a cell commences its operation from a quiescent (diastolic) state to an active (electrical) state.

In accordance with an embodiment or aspect, a method of identifying a source associated with a cardiac rhythm disorder is disclosed. The method comprises receiving cardiac information signals from sensors of a catheter associated with a patient's heart during the cardiac rhythm disorder. A representation is generated using the cardiac information signals received from the sensors by transformation of spline-sensor locations of the catheter to x-y coordinate pairs of locations. A first offset is determined resulting from a perturbation to corresponding x-y coordinate pairs of locations associated with the representation, the first offset displacing coordinate pairs of sensor locations of the representation at least one unit of displacement in a first direction. A source associated with the cardiac rhythm disorder is identified when activations associated with the cardiac information signals rotate in sequence at least once, or emanate centrifugally for at least a first time period, the source being identified based on the representation as displaced.

In yet a further disclosed embodiment, the method further comprises determining a second offset of corresponding coordinate pairs of locations of the representation in one or more second units of displacements in at least one direction, in identifying one or more remote or polar sources. The method further includes the unit of displacement including at least one of an angle between splines, spline-sensor offset, a spline offset, a sensor offset, and an angle of tilt. The method yet further includes that the perturbation associated with the representation includes displacing the coordinate pairs of locations in one or more units of displacement in two or more directions, the unit of displacement being above a threshold. The method yet further includes determining an angle of tilt above a threshold, the perturbation displacing coordinate pairs of locations of the representation in two or more directions in order to identify one or more sources of the cardiac rhythm disorder. The method yet further includes at least one source of the cardiac rhythm disorder is a remote source or polar source relative to the sensors or the catheter. The method further includes determining an approximate location of the source based on sensor locations associated with the cardiac information signals that rotate in sequence at least once, or emanate centrifugally for at least a first time period using transformed spline-sensor (x-y) coordinate points of the representation. The method yet further includes determining an approximate location of the source based on a polygon formed of coordinate pairs of sensor locations bounding at least one source. The method yet further includes the polygon being formed by three or more co-located positional vertices bounding the source as the source rotates or emanates centrifugally for one or more time periods on or near the polygon. The method yet further includes determining a likely core associated with at least one rotational or centrifugal path based on the polygon bounding the rotational or centrifugal path for at least one time period. The method yet further includes identifying at least one continuous rotational or centrifugal path of one or more sources located near or within the polygon bounding the source. The method yet further includes detecting an angular tilt associated with coordinate pairs of sensors of the catheter model, calculating at least one spline-sensor translation of the plurality of spline-sensor references to x-y coordinate points based on the angular tilt displacing the representation; and determining a path of a rotational or centrifugal source using positional vertices bounding the source in a polygon as it rotates or emanates centrifugally for one or more time periods on or near the polygon. The method yet further includes identifying a remotely located rotational or centrifugal source relative to the representation by applying one or more offsets to the representation in one or more units of displacement as determined, the remotely located rotational or centrifugal source being displaced within grid boundaries of the representation.

The method in yet further disclosed embodiments, includes translation of the at least one spline-sensor by detecting the angle between two splines of the catheter as indicated in the representation; calculating the translated sensor-spline value using: the tilt angle formed between the original axis of the representation and the representation once tilted and the detected angle between two splines; and applying the translated sensor-spline value to a transformed x-y coordinate representation of the cardiac information signals. The method yet further includes determining an origin of the spline-sensor location(s) wherein the representation is fragmented into a panoramic grid representation in order to identify the likely location of the remotely located source of the cardiac rhythm disorder. The method yet further includes determining an origin of a sensor location, wherein the representation is fragmented into the panoramic grid representation in order to identify the likely location of a remote source located at or near a polar region of the heart relative to the representation.

In yet another disclosed embodiment, a method of identifying a remote or polar source associated with a cardiac rhythm disorder comprises receiving a representation of cardiac information signals from a plurality of sensors associated with the patient's heart during the cardiac rhythm disorder. A tilt of a catheter model of cardiac information signals in at least one direction is detected wherein the tilt rotates the catheter model at least one spline-sensor unit. At least one spline-sensor translation of the cardiac information signals associated with the catheter model, is calculated using the detected rotational tilt associated with the catheter model. A rotational source associated with transformed cardiac information signals, is identified by applying the spline-sensor translation to the representation of cardiac information signals.

In yet a further embodiment, disclosed is a method of identifying a remote source associated with a biological rhythm disorder. The method comprises receiving biological information signals from sensors of a catheter associated with a patient's heart during the cardiac rhythm disorder. A representation is generated using the biological information signals received from the sensors by transformation of spline-sensor locations of the catheter to x-y coordinate pairs of locations. A first offset is determined resulting from a perturbation to corresponding x-y coordinate pairs of locations associated with the representation, the first offset displacing coordinate pairs of sensor locations of the representation at least one unit of displacement in a first direction. A remote source associated with the biological rhythm disorder is identified when activations associated with the biological information signals rotate in sequence at least once, or emanate centrifugally for at least a first time period, with the source being identified based on the representation as displaced.

In accordance with another embodiment or aspect, a system associated with identifying a source associated with a cardiac rhythm disorder is disclosed. The system comprises a plurality of sensors disposed at multiple locations in relation to a heart that sense cardiac information signals, and a processor interfacing with the plurality of sensors. The processor is configured to receive cardiac information signals from sensors of a catheter associated with a patient's heart during the cardiac rhythm disorder. A representation is generated using the cardiac information signals received from the sensors by transformation of spline-sensor locations of the catheter to x-y coordinate pairs of locations. A first offset is determined resulting from a perturbation to corresponding x-y coordinate pairs of locations associated with the representation, the first offset displacing coordinate pairs of sensor locations of the representation at least one unit of displacement in a first direction. A source associated with the cardiac rhythm disorder is identified when activations associated with the cardiac information signals rotate in sequence at least once, or emanate centrifugally for at least a first time period, the source being identified based on the representation as displaced.

In yet a further disclosed embodiment, the system comprises a processor further configured to determine a second offset of corresponding coordinate pairs of locations of the representation in one or more second units of displacements in at least one direction, in identifying one or more remote sources. The system further includes that unit of displacement include at least one of an angle between splines, spline-sensor offset, a spline offset, a sensor offset, and an angle of tilt. The system further includes that the perturbation associated with the representation includes displacing the coordinate pairs of locations in one or more units of displacement in two or more directions, the unit of displacement being above a threshold. The system further comprises that the processor is further configured to determine an angle of tilt above a threshold, the perturbation displacing coordinate pairs of locations of the representation in two or more directions in order to identify one or more sources of the cardiac rhythm disorder.

The system in yet further disclosed embodiments includes that at least one source of the cardiac rhythm disorder is a remote source relative to the sensors or the catheter. The processor is further configured to determine an approximate location of the source based on sensor locations associated with the cardiac information signals that rotate in sequence at least once, or emanate centrifugally for at least a first time period using transformed spline-sensor (x-y) coordinate points of the representation. The system includes that the processor is further configured to determine an approximate location of the source using a polygon based on coordinate pairs of sensor locations bounding at least one source. The system further includes the processor is further configured to generate the polygon based on three or more co-located positional vertices bounding the source as the source rotates or emanates centrifugally for one or more time periods on or near the polygon. The system is further configured to determine a likely core associated with at least one rotational or centrifugal path based on the polygon bounding the rotational or centrifugal path for at least one time period. The system further includes that the processor is further configured to identify at least one continuous rotational or centrifugal path of one or more sources located near or within the polygon bounding the source.

In yet a further disclosed embodiment, the system further includes the processor is further configured to: detect an angular tilt associated with coordinate pairs of sensors of the catheter model; calculate at least one spline-sensor translation of the plurality of spline-sensor references to x-y coordinate points based on the angular tilt displacing the representation; and determine a path of a rotational or centrifugal source using positional vertices bounding the source in a polygon as it rotates or emanates centrifugally for one or more time periods on or near the polygon. In yet a further disclosed embodiment, the processor is further configured to identify a remotely located rotational or centrifugal source relative to the representation by applying one or more offsets to the representation in one or more units of displacement as determined, with the remotely located rotational or centrifugal source being displaced within grid boundaries of the representation.

In yet a further disclosed embodiment, the system includes that the translation of the at least one spline-sensor comprise the processor being further configured to detect the angle between two splines of the catheter as indicated in the representation; calculate the translated sensor-spline value using the tilt angle formed between the original axis of the representation and the representation once tilted and the detected angle between two splines; and apply the translated sensor-spline value to a transformed x-y coordinate representation of the cardiac information signals.

In yet a further disclosed embodiment, the system includes that the processor is configured to determine an origin of the spline-sensor location(s), wherein the representation is fragmented into a panoramic grid representation in order to identify the likely location of the remotely located source of the cardiac rhythm disorder. The processor is further configured to determine an origin of a sensor location, wherein the representation is fragmented into the panoramic grid representation in order to identify the likely location of a remote source located at or near a polar region of the heart relative to the representation.

In yet a further disclosed embodiment, a system associated with identifying a remote source associated with a cardiac rhythm disorder comprises a plurality of sensors disposed at multiple locations in relation to a heart to sense cardiac information signals; and a processor interfacing with the plurality of sensors. The processor is configured to receive a representation of cardiac information signals from a plurality of sensors associated with the patient's heart during the cardiac rhythm disorder; detect a tilt of a catheter model of cardiac information signals in at least one direction, wherein the tilt rotates the catheter model at least one spline-sensor unit; calculate at least one spline-sensor translation of the cardiac information signals associated with the catheter model using the detected rotational tilt associated with the catheter model; and identify a rotational source associated with transformed cardiac information signals by applying the spline-sensor translation to the representation of cardiac information signals.

In yet a further disclosed embodiment, a system associated with identifying a remote source associated with a biological rhythm disorder is disclosed. The system comprises a plurality of sensors disposed at multiple locations in relation to a heart to sense cardiac information signals, and a processor interfacing with the plurality of sensors. The processor is configured to: receive biological information signals from sensors of a catheter associated with a patient's heart during the cardiac rhythm disorder; generate a representation using the biological information signals received from the sensors by transformation of spline-sensor locations of the catheter to x-y coordinate pairs of locations; determine a first offset resulting from a perturbation to corresponding x-y coordinate pairs of locations associated with the representation, the first offset displacing coordinate pairs of sensor locations of the representation at least one unit of displacement in a first direction; and identify the remote source associated with the biological rhythm disorder when activations associated with the biological information signals rotate in sequence at least once, or emanate centrifugally for at least a first time period, with the source being identified based on the representation as displaced.

In accordance with further disclosed embodiment or aspect, a computer-readable medium stores instructions which, when executed by a processor or computing device, cause the processor or computing device to perform operations. The operations include receiving cardiac information signals from sensors of a catheter associated with a patient's heart during the cardiac rhythm disorder; generating a representation using the cardiac information signals received from the sensors by transformation of spline-sensor locations of the catheter to x-y coordinate pairs of locations; determining a first offset resulting from a perturbation to corresponding x-y coordinate pairs of locations associated with the representation, the first offset displacing coordinate pairs of sensor locations of the representation at least one unit of displacement in a first direction; and identifying a source associated with the cardiac rhythm disorder when activations associated with the cardiac information signals rotate in sequence at least once, or emanate centrifugally for at least a first time period, with the source being identified based on the representation as displaced.

In accordance with further embodiment or aspect, a computer-readable medium that stores instructions which, when executed by a processor or computing device, cause the processor or computing device to perform operations that include receiving a representation of cardiac information signals from a plurality of sensors associated with the patient's heart during the cardiac rhythm disorder; detecting a tilt of a catheter model of cardiac information signals in at least one direction, wherein the tilt rotates the catheter model at least one spline-sensor unit; calculating at least one spline-sensor translation of the cardiac information signals associated with the catheter model using the detected rotational tilt associated with the catheter model; and identifying a rotational source associated with transformed cardiac information signals by applying the spline-sensor translation to the representation of cardiac information signals.

These and other purposes, goals and advantages of the present application will become apparent from the following detailed description read in connection with the accompanying drawings.

BRIEF DESCRIPTION OF THE DRAWINGS

The application includes at least one drawing executed in color. Copies of this application with color drawing(s) will be provided by the Patent and Trademark Office upon request and payment of the necessary fee.

Some embodiments or aspects are illustrated by way of example and not limitation in the figures of the accompanying drawings in which:

FIG. 20A illustrates an adjusted view of a 3-D catheter model with a split performed between sensors in order to center the rotor circuit region with the grid;

DETAILED DESCRIPTION

Figure 1:
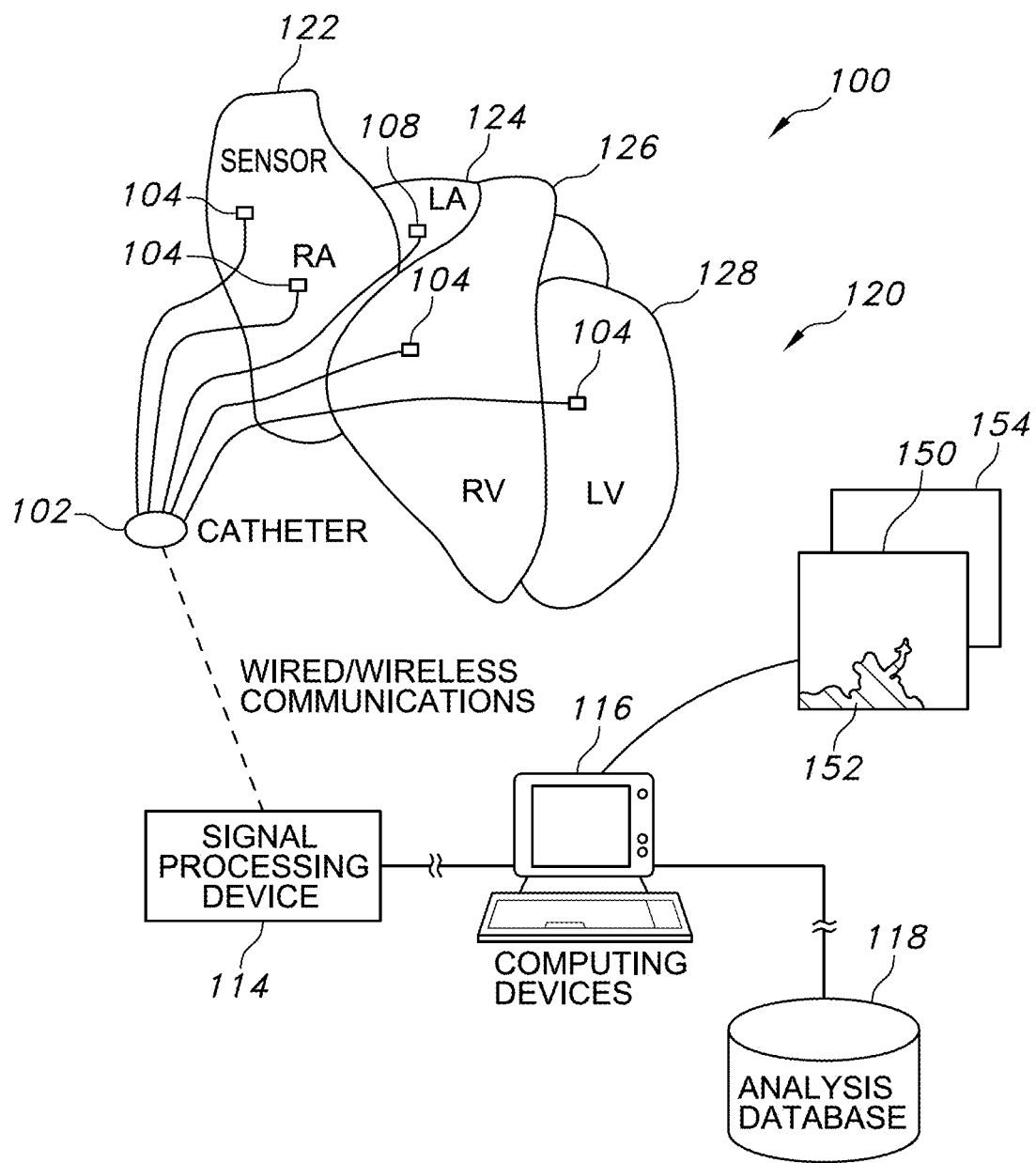
FIG. 1 illustrates a system to identify the location of a rotational source or focal source of a heart rhythm disorder.

A system and method to identify the location of a rotational source of a biological rhythm disorder, such as a heart rhythm disorder, including remote sources located at or near polar regions of an organ (for example, polar sources), in relation to a basket catheter and/or its sensors, for example, is disclosed herein. In the following description, for the purposes of explanation, numerous specific details are set forth in order to provide a thorough understanding of example embodiments or aspects. It will be evident, however, to one skilled in the art, that an example embodiment may be practiced without all of the disclosed specific details.

In accordance with an embodiment of the invention, there is provided a system and method to represent causes of the biological or heart rhythm disorder in a format that can assist the physician in treatment. For example, a visual display screen may be connected to a processor to allow for viewing of the activation trail and to allow for visual location of the core of a rotor, focal source or other cause of the disorder, and in particular when such rotor, source or other cause of a biological rhythm disorder is remotely located with respect to the sensing device, catheter, sensors of catheter or other device implemented in the collection and arrangement of cardiac information data. Audio formats may also be used alone or in combination with the visual format. For example, in addition to or instead of the visual depiction of the source such that the core can be visually identified, the coordinates of the source and its core can be provided to the user by audio indications as to the location and cause of the disorder. Visual depiction is particularly desirable because it provides the practitioner with a clear representation of the cause and provides a reference for identifying the core of the cause, which greatly facilitates the selection of treatments. For example, a visual representation of the actual rotor or focal beat allows the practitioner to accurately determine where to direct the ablation catheter or other treatment, once the remotely located activity is identified by the practitioner and the source of the disorder is discernible.

In accordance with another embodiment of the invention, once the cause and/or source of the disorder is identified, use of a treatment device or method, to modify or destroy the site of an identified and localized source may be employed to treat or eliminate the rhythm disorder. Non-limiting examples of treatment devices and methods include the use of destructive energy (ablation) such as by ablation catheters, surgical ablation methods, surgical removal or using devices inside the heart such as implanted leads or other physical device, stimulating energy (pacing), direct delivery of pharmacologic agents, cellular therapy or other intervention techniques. In one embodiment, a catheter capable of sensing signals from the body, and particularly from the heart, may also include a means of treatment, such as the ability to delivery ablation energy, stimulation energy, drug therapy, cellular therapy such as stem cells or gene therapy, or other treatment means. Thus, such a catheter may be employed both in the detection and in the treatment of the disorder.

The present invention is particularly suited for the detection, diagnosis and treatment of complex heart rhythm disorders such as, for example, VF, polymorphic VT, torsade de pointes and AF, where once the localized cause is accurately identified and pinpointed, accurate and targeted ablation of the localized cause may be implemented. As discussed above, identification and physical location of the cause at a remote or polar location of an organ relative to a sensing device, such as a basket catheter, or other sensing device that collects, reconstructs and/or images cardiac information, was previously not possible, and hence extraordinarily difficult even for experienced practitioners to treat successfully, much less substantially ameliorate or eliminate.

FIG. 1 illustrates an example system for identifying the location of one or more sources in connection with a heart rhythm disorder 100. The example system 100 is configured to identify rotational activity, persistent rotational activity, any rotational sources such as rotors, centrifugal patterns or propagation (whether radially emanating or other apparent dispersal), the approximate core of one or more sources, drivers and/or other activity associated with cardiac signals detected from a patient's heart 120 in order to identify or locate the source of a heart rhythm disorder. The heart 120 includes a right atrium 122, left atrium 124, right ventricle 126 and left ventricle 128.

The example system 100 includes a catheter 102, signal processing device 114, computing device 116 and analysis database 118.

In the shown embodiment, the catheter 102 is configured to detect cardiac information including activation information in the heart and to transmit the detected cardiac electrical information to the signal processing device 114, either via a wireless or wired connection. The catheter includes an array of probes/sensors 104, which can be inserted into the heart through the patient's blood vessels. Sensors 104 may provide unipolar and/or bipolar signals.

In a preferred embodiment, a basket-type catheter is introduced in the patient's heart. It is noted that the rotational sources of various heart rhythm disorders can be situated at different locations in different chambers of the heart and can rotate in different directions (e.g., clockwise, counterclockwise) about various centers of rotation. The rotational sources may be located at the outer perimeters of the heart which may pose additional challenges in viewing the computer-generated two-dimensional electrical grid views of these rotational sources. The sources may also be persistent in nature but, nonetheless, can also precess to other locations of the heart. The sources may also overlap in their rotational paths with other sources including with detected focal beats that may be repeating, very repetitive or otherwise persistent in its manifested form of activity.

In some embodiments or aspects, one or more of the sensors 104 are not inserted internally into the patient's heart 120. For example, sensors, other sensing device and/or other cardiac information signal(s) detection device, may detect cardiac electrical information via the patient's surface (e.g., electrocardiogram) or remotely without contact with the patient (e.g., magnetocardiogram or other methods to identify electrical information via the inverse solution). As another example, sensors may also derive cardiac electrical information from cardiac motion of a non-electrical sensing device (e.g., echocardiogram). In various embodiments or aspects, these sensors and/or other sensing devices, can be used separately or in different combinations, and further these separate or different combinations can also be used in combination with sensors inserted into the patient's heart 120 or other organ.

The sensors 104 are positioned spatially at respective various sensor locations either adjacent to or contacting tissue in the heart 120 or near the heart 120. The sensors 104 can detect cardiac electrical activity at the sensor locations and can generate corresponding sensing cardiac information signals which are output to the signal processing device 114. The sensors 104 may further be configured to deliver energy to ablate the heart 120 at the various sensor locations, particularly when the sensor location is adjacent to or contacting heart tissue.

The signal processing device 114 is configured to process (e.g., clarify and amplify) the sensing cardiac signals generated detected by the sensors 104 and to output corresponding cardiac signals. The computing device 116 receives or accesses the cardiac signals for analysis or processing (which refers to receiving or accessing) the cardiac signals and processes them in accordance with the methods disclosed herein. In some embodiments, the signal processing device 114 is configured to provide unipolar signals, however, in other embodiments, the signal processing device 114 may provide bipolar signals.

The disclosed methods are used to identify the location of rotational activity (clockwise or counterclockwise) and/or cardiac activation information, other electrical activity, rotational activity, a core associated with the rotational activity, an approximate core associated with the rotational activity, focal activity, focal beats—the origin from which, centrifugal activation emanates—and/or other activity including that of: a core of a rotational source, persistent repetitive activations and/or any other activity, and activations, repetitive or otherwise, as propagated or detected from the cardiac signals. The sources associated with biological or heart rhythm disorders may be located in regions of the heart or organs that are more remote or considered edge activity with regard to the position of the basket catheter subassembly in interior regions of the heart. Some of the sources may appear to be in polar or edge regions of the organ or heart relative to the delivery of the basket catheter subassembly in the organ or heart, and therefore, rotational activity is generally considered more difficult to locate and identify. In accordance with the disclosed invention, methods are described herein below for detecting sources including focal sources or other centrifugal patterns that are remotely located relative to the position of the basket catheter subassembly in the heart or organ.

The computing device 116 is configured to receive (or access) cardiac signals from the signal processing device 114 and further configured to analyze or process the cardiac signals in accordance with methods, functions or logic disclosed herein to determine regularity in various regions of the patient's heart, including polar or edge regions of the heart, such that it is possible to locate and identify a source(s) of the heart rhythm disorder and thus, to eliminate the identified source(s). In accordance with the disclosed methods, a basket style catheter may be introduced into the heart. The signals as processed generate a 3-dimensional model of the heart that may be rotated at various spline/electrode points in order to assist with the identification of the location of the rotational source and generate a 2-dimensional grid representation or other map of the rotational source (e.g. rotor) of the heart rhythm disorder.

The computing device 116 generates a first representation 150, for example, in the form of an activation propagation map (APM) video that combines and spatially lays out data from a plurality of monophasic action potential (MAP) voltage representations of the cardiac signals. The APM video includes a sequence of APM frames that are associated with a series of time increments over a time interval. Arrow 152, in the shown example, indicates rotational movement of displayed information. Each element in the MAP representation is associated with a respective sensor 104 of the array of sensors. A MAP representation includes voltage (or charge) versus time and other indexes. In other contemplated embodiments, further illustrated in FIG. 1, are one or more second representations associated with one or more sources of a complex rhythm disorder, such one or more second representations being generated in the form of visual, auditory, tactile, other sensory data and/or combinations or variations thereof. The first representation 150 may be in the form of a display, a clinical representation, sensory representation, other representation and/or combination thereof, which assists the practitioner in identification of and treatment of the rhythm disorder by facilitating the identification of the source of the rhythm disorder. The one or more second representations 154 may be in the form of a display, a clinical representation, sensory representation, other representation and/or combination thereof which assists the practitioner in identification of and treatment of the rhythm disorder by facilitating the identification of the source of the rhythm disorder. Other representations discernible to a practitioner in the treatment of the rhythm disorder, including a multisensory representation, whereby one or more sensory modalities, such as sight, sound, touch, smell, tactile, and/or motion, may be integrated as one or more clinical and/or sensory representations, whether delivered to and/or stored on a device, display, computer readable medium, representation tool or device, and/or memory, which in effect, steer the practitioner prior to and during the treatment of the rhythm disorder.

The first representation 150 and one or more second representations 154 shown in the system in FIG. 1, are associated with sensory representations of the identification or location of causes or sources of rhythm disorders, whether visual, auditory, tactile, combinations thereof, which is/are used to direct and assist the physician in treating or eliminating the rhythm disorder. For example, this module may include a display screen which permits the textual, graphic and/or auditory visualization on the screen of the rotor, focal or other cause of the disorder to be more clearly visualized or located by the practitioner. In some embodiments, the one or more second representations 154 are generated as a "movie" clip of the disorder, as located and presented on the screen in movie video format. Such clip is a real-time presentation of the actual cause and location of the disorder. For example, once the analysis of the data has been performed in accordance with the process of the disclosure, i.e., the identification of location of the source of the complex rhythm disorder that is remotely located relative to the catheter sensors, will be shown on the screen in the form of an activation trail. If the pattern of the activation trail signifies a series of activations revolving around a central core, then a rotor has been found, and is in fact, a cause of the disorder. Similarly, if the pattern of the activation trail signifies a series of activations that emanate radially from a central core region, then a focal beat has been found and is in fact a cause of the disorder. Thus, the process permits the direct finding of the cause of the disorder, which were otherwise, situated in remote locations or polar regions, and non-discernible when converted to 2-dimensional grid formats or other visual representations. The convenient visualization of the existence, type and location of the disorder for the practitioner is thereby generated in the first representation 150 and/or in the one or more second representations 154.

An auditory representation may be generated in the form of one or more second representations 154, such as for example, an auditory signal, tactile signal or similar sensory signal, that vocalizes or converts cardiac information into representative auditory or tactile representations associated with the identification, location and other characteristics indicative to the practitioner of sources for biological rhythm disorders. As an example, a tactile sensory representation is generated by converting processed cardiac information signals into tactile images. The tactile images are felt by the user enabling them to obtain visual or auditory information by touch about the identification of the location and other information associated with the source of the complex rhythm disorder that is otherwise discernible through vision and/or hearing. Further tactile images may be produced by tactile vibrations of at least a portion of a tactile display or tactile sensory representation. Such representations may even further guide the practitioner in more precisely locating the source of the complex rhythm disorder while performing relevant procedures. Any such first representation 150 and/or second representations 154 may be delivered to a display device, a computer readable medium which stores the representation or other device which generates the representations (150, 154) including clinical representation(s). In order to detect rotational activity such as rotors, information such as rotational angles, solid angles, angular velocity, and tangential velocity at the circumference of rotation and phase information, may be used in the detection thereof. For focal sources, information may also include centrifugal indexes (such as velocity and acceleration), and centripetal indexes (such as velocity and acceleration). Centripetal indexes typically indicate a passive area (not a source), but may indicate a source that is moving away from the sensor. For all sources, quantification includes stigmata of dynamic movement such as Doppler shift, disorganization in the core, and measures of entropy since the source may move constantly and dynamically within the region of the heart.

Information may also include activation onset time information associated with the electrical activity sensed by a sensor 104 of the array of sensors. The MAP representation can be mapped as curves on time and voltage axes, as well as several other representations including polar plots and three-dimensional plots.

As used herein, activation onset time is a time point at which activation commences in a cell or tissue, as opposed to other time points during activation. Activation is a process whereby a cell commences its operation from a quiescent (diastolic) state to an active (electrical) state.

The computing device 116 receives, accesses, or generates the signal representations, such as APM video, to the first representation 150. An example of generation of an APM video, and a signal representation in the form of a monophasic action potential (MAP) is described in U.S. Pat. No. 8,165,666, which is incorporated herein by reference in its entirety. In particular, FIG. 11 of the '666 patent illustrates an APM video 150 of MAPs. Other signals of value include noise-free unipolar electrograms and processed unipolar electrograms. Similarly, other systems and methods can reconstruct cardiac or biological activation information to include activation times, phase information and onset.

The first representation 150, for example, the APM video, may be generated by systems and methods that can display, process or reconstruct cardiac or biological electrical information over time to generate a dynamic video representation of activation information, electrical activity, rotational activity and/or a core associated with the rotational activity, centrifugal activity, focal activity and/or the origin from where centrifugal or rotational activation emanates or propagates, including persistent or repeated emanation radially or other apparent forms of dispersal.

In one embodiment or aspect, rotational activation is indicated from phase mapping by a phase singularity, in which the dynamic activation information may exhibit rotational motion. The APM video as generated in the first sensory representation 150, for example, may display an indicator of a phase singularity, such as a white dot, that may be determined by calculations performed per frame. Each frame displays information based on measurements made at the time of the frame. The degree of confidence in each rotational driver in this embodiment is indicated by the persistence of a phase singularity over time. Singularities detected for only a short amount of time may be displayed in only a few frames so that the visual indication is not visible, is barely visible, and/or quickly disappears. When there is persistence, the frame-by-frame rotational motion may be visible and detectable to a viewer.

Figure 2:
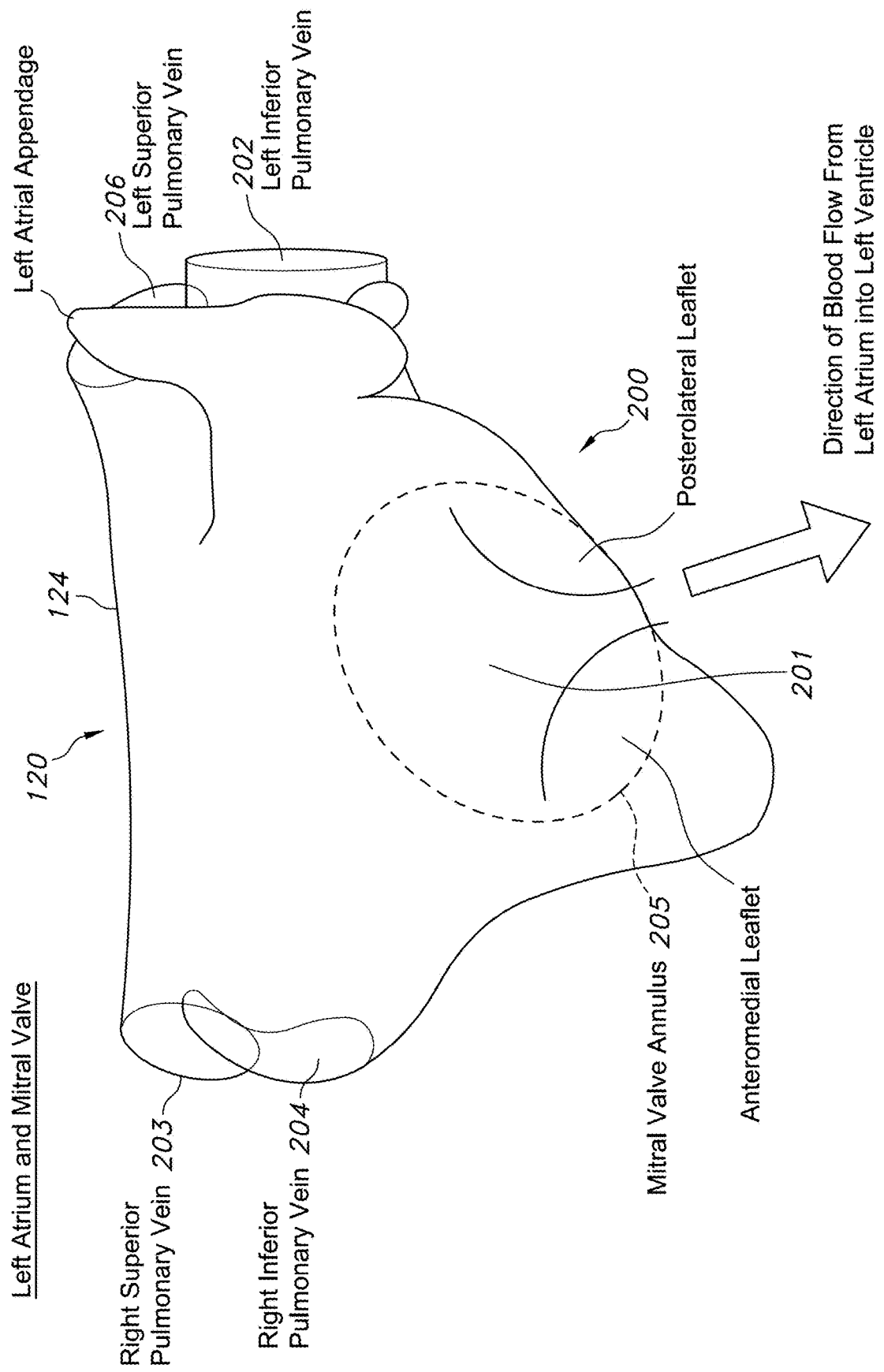
FIG. 2 illustrates a sample diagram of the left atrium and mitral valve of the heart.

FIG. 2 illustrates a diagram of the left atrium (200) and mitral valve (205) of the heart (200) prior to insertion of for e.g., a basket-style mapping catheter. The catheter is generally deliverable using a catheter guide or delivery sheath into the desired vein. It is positioned generally facing one of the valve annulus, which in the left atrium (200) is the mitral valve annulus (205). Electrical events in the heart (120) are generally recorded using sensing electrodes or sensors. These electrodes may be catheters placed within the chambers or vasculature of the heart, including custom-designed recording catheters. The electrodes may also be extensions of leads from an implanted pacemaker or cardioverter-defibrillator, catheters used to record monophasic action potentials, or other signals, that typically arrive via the right superior vena cava and the inferior vena cava (collectively "vena cavae"), the right superior pulmonary vein (203), the right pulmonary vein (204), the left superior pulmonary vein (206), the left inferior pulmonary vein (202) or coronary sinus.

Figures 3A, 3B:
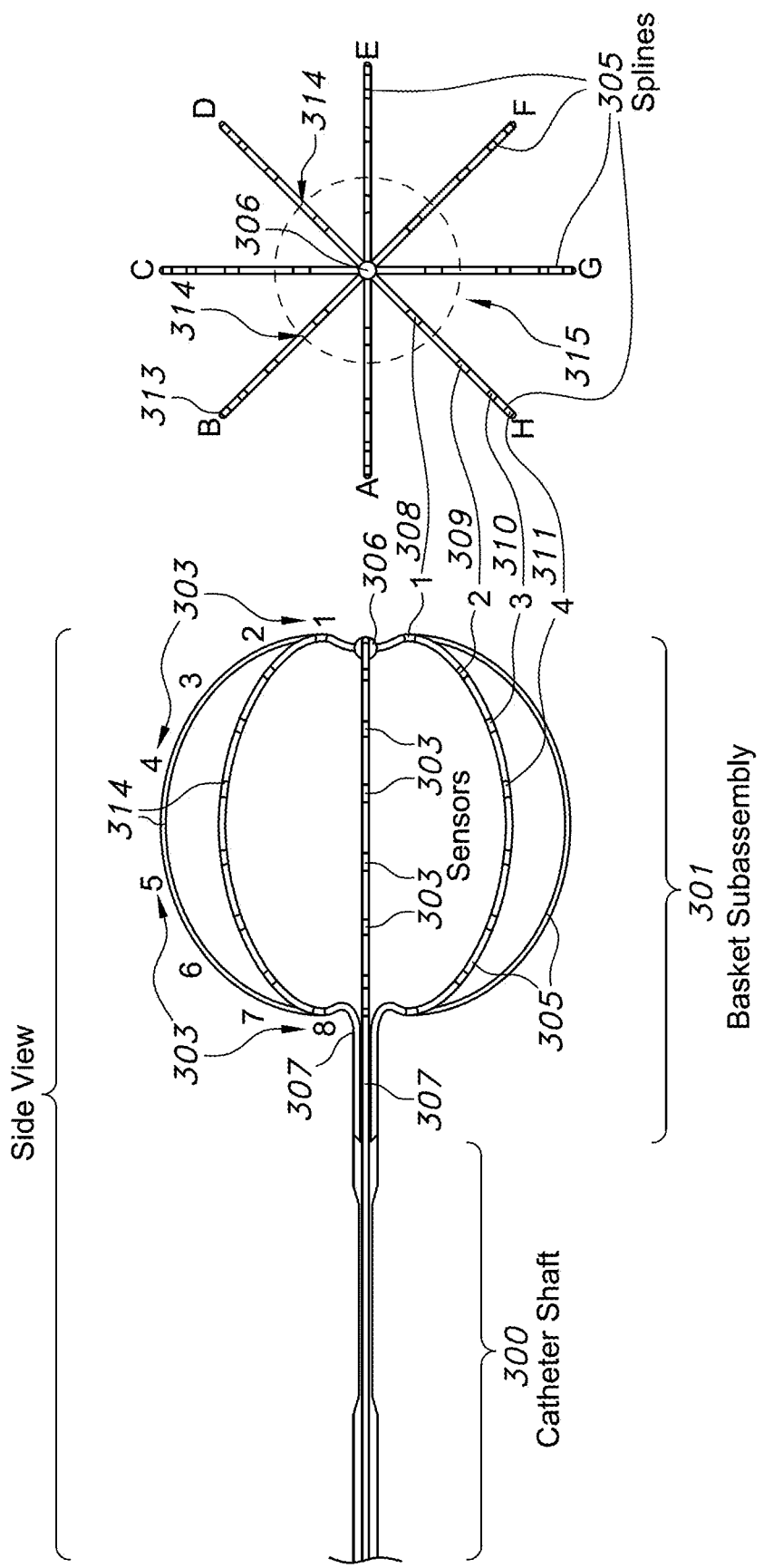
FIG. 3A illustrates an expanded side view of a basket catheter sub-assembly.
FIG. 3B illustrates a front perspective view of the splines of the basket catheter subassembly (301) of FIG. 3A.

FIG. 3A illustrates an expanded side view of a basket catheter including the basket subassembly shown with splines in their radially expanded state. In the shown embodiment of the basket catheter assembly (301), included is a catheter shaft (300) connecting to splines (A-H) (305) in the basket subassembly's radially expanded configuration. The splines (305) of the basket assembly (301) are sufficiently flexible to match the contours of the inner walls of the heart where the catheter is positioned e.g., the left atrium. Along the surface of each spline (305) are up to eight electrodes or sensors (303) which traverse in equi-distances and in some embodiments at varying distance therebetween, along the outer surface of each spline (305). The electrodes or sensors (303) are used to detect multiple local electric voltages from the endocardial surface. The splines (305) of the spline basket subassembly (301) are secured by a distal tip (306) at one end, i.e. the distal end of the basket (301) and further secured by a proximal anchor (307) at an opposed end, i.e. proximal end, of the basket (301). Other embodiments may implement basket subassemblies of other configurations.

FIG. 3B illustrates a front perspective view of the splines of the basket subassembly (301) of FIG. 3A. Each spline (305) is shown radially and symmetrically expanded lengthwise up to its medial point (314) designated at the intersection of dotted line (315). The sensors (303) shown in FIG. 3A designated as sensors or electrodes numbers 1-4 (elements (308)-(311)) (i.e. most distal to most proximal points) correspond to the electrodes designated as numbers 1-4 (elements (308)-(311)) in FIG. 3B (i.e. from most distal to most proximal points on the spline (305)). It is generally desirable to prevent spline/electrode misidentification under fluoroscopy. Recent advances in basket assembly catheter designs have addressed issues of misidentification and positional instability of the basket assembly catheter once deployed in the location of the heart i.e. left or right atrium as described in U.S. Pat. No. 8,644,902, incorporated by reference herein.

The splines (305) as shown in both FIGS. 3A and 3B, designated A through H, are generally flexible for guiding a plurality of exposed electrodes (at least 308 through 311), the splines having proximal portions (313), distal portions (306) and medial portions (314) there between. The basket catheter design helps facilitate three-dimensional and two-dimensional graphical mappings of a rotational source associated with a heart rhythm disorder in a patient. A rotational source can be evaluated by a physician to be along the electrode reference 303, anywhere between about electrodes 1-8, and along the spline reference 307, anywhere between about splines A-H, of the basket-type catheter once deployed into the patient's heart. It is noted that the rotational sources of different heart rhythm disorders can be disposed at different locations e.g. in different chambers, right or left atrium or portions of the heart, and can rotate in different directions (e.g., clockwise) about various centers of rotation.

Figure 4:
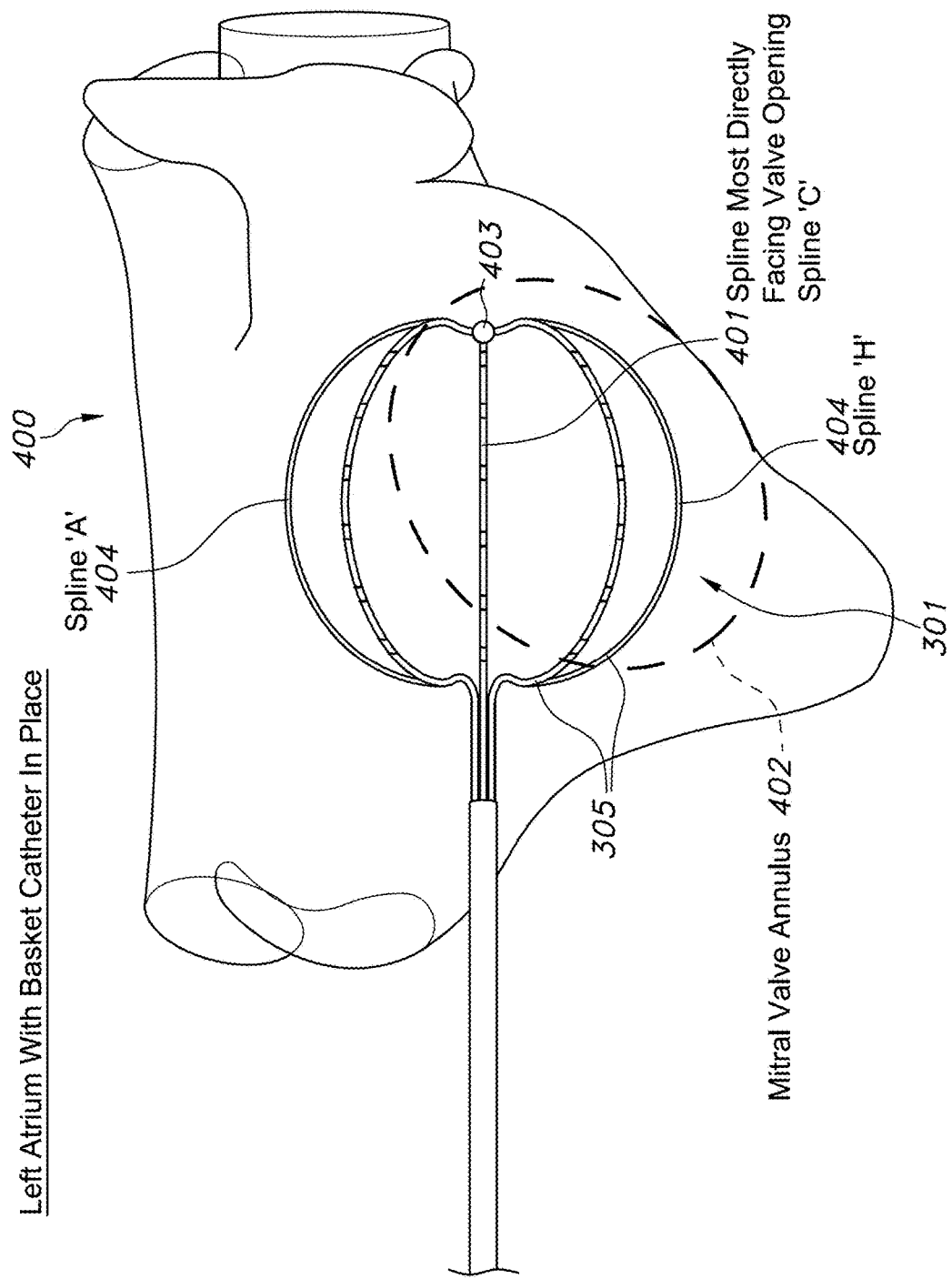
FIG. 4 is an illustration of the basket catheter subassembly as delivered in the left atrium of the heart.

FIG. 4 is an illustration of the basket catheter subassembly (403) delivered in the left atrium of the heart (400) with spline C (401) most directly facing the mitral valve annulus (402). It is noted that generally, any one of the splines designated A-H (404), may be delivered in the atrium of the heart while facing the mitral valve annulus (402). However, the placement and delivery of the catheter subassembly (403) generally depends on the patient's anatomical proportions and the area of the heart of greater interest (i.e. exhibiting symptoms) to the surgeon performing the procedure. The catheter may be delivered into other chambers of the heart, e.g. left atrium, right ventricle, left ventricle or combinations of chambers, including the endocardial or epicardial surfaces. Since the heart is not a uniform or planar structure, the spatial arrangement of electrodes (303) on each spline (305) may vary depending on the delivery of the basket catheter (403) into the subject region of the heart (400). In addition, in certain embodiments, different catheters with various spatial arrangements of the sensors (303), such as spiral radial spokes or other spatial arrangements may be used. The splines (305) of the basket catheter (301) generally conform to the contours of the walls of the chamber of the heart (120). Therefore, the spatial arrangement of the sensors (303) as located along each spline (405) varies depending on the structure of the patient's heart (120) and ultimately, how the splines/sensors are oriented in and against the walls of the heart (120).

Figure 5:
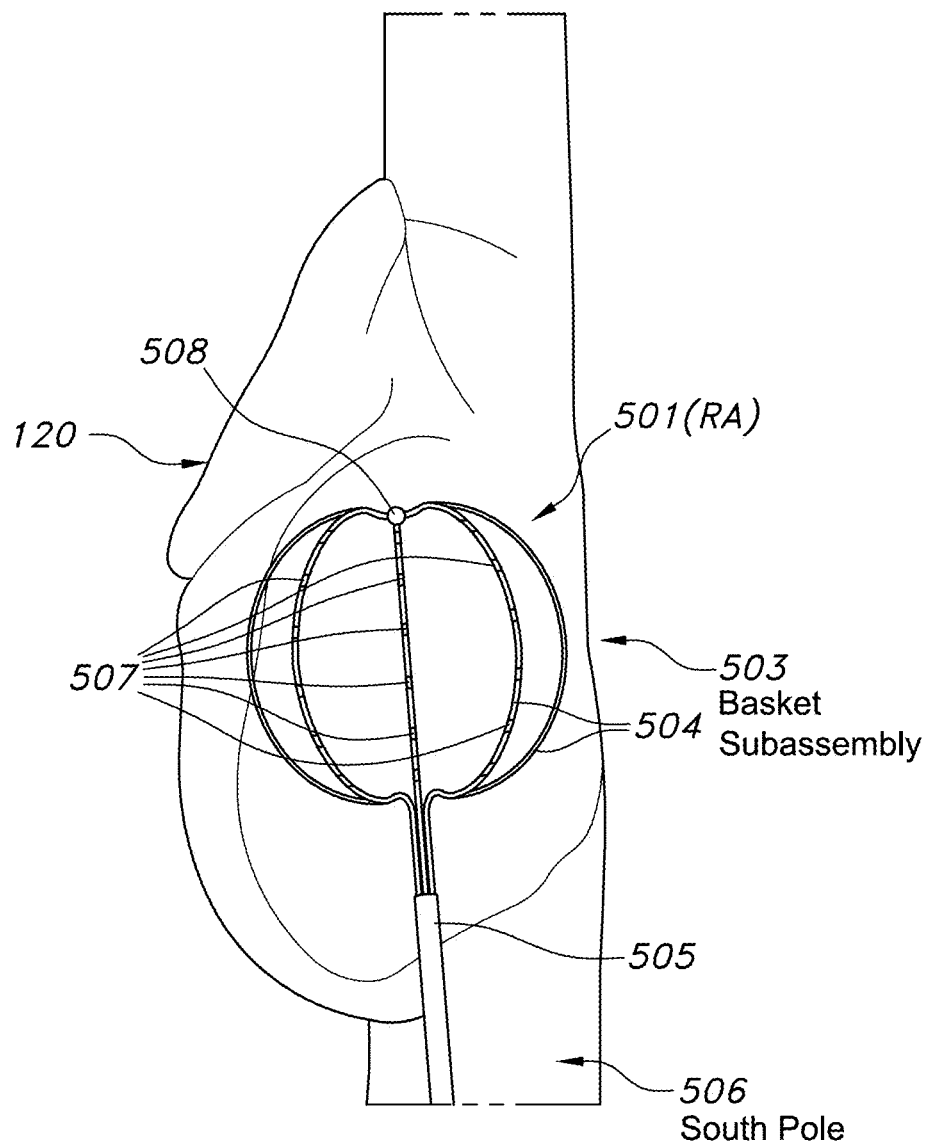
FIG. 5 is an illustration of the basket catheter subassembly delivered in the right atrium of the heart.

FIG. 5 is an illustration of the basket catheter subassembly (503) delivered in the right atrium (501) of the heart (120) with at least one spline (504) directly facing the tricuspid valve. In this particular embodiment, the catheter is delivered from the southern pole (506) of the heart (120). Spline A of the basket subassembly (503), for example, directly faces the tricuspid valve of the right atrium (501). It is noted that generally any one of the splines designated A-H (504) may be delivered into the atrium of the heart with any one of those splines delivered directly facing the tricuspid valve (also generally depending on the patient's anatomical proportions and the area of the heart of greater interest (i.e. exhibiting symptoms) to the surgeon performing the procedure). The catheter subassembly (503) includes splines (504) for guiding a plurality of electrode sensors (507) that are spatially arranged along each spline (504) and used to detect local electric voltages from endocardial surface thereat. The splines (507) of the basket catheter (503) generally conform to the contours of the walls of the chamber of the heart (501). The most distal portion is shown at distal tip (508). Therefore, the spatial arrangement of the sensors (507) as located along each spline (504) varies depending on the anatomical structure of the patient's heart. It is also noted that variations in techniques for delivery of the catheter may occur.

In one embodiment, the catheter is navigated through muscle into a desired vein. A catheter, typically a long guide sheath, may be used and a vessel or cavity may be punctured with a sharp hollow needle or trocar. The introducing catheter may be positioned using guidewire into the subject cavity or vessel of the heart. In these scenarios, the catheter is delivered into the cavity of the heart but, the splines and thus, sensing electrodes, have limited maneuverability once a vessel or cavity has been punctured. Thus, the disclosed methods permit for the respective 3-D modeling of the signals including for the identification of rotational sources. The disclosed methods include the possibility to rotate the 3-D catheter image for analysis of the respective captured signals so that the mathematical translation of respective signals to a 2-dimensional grid may occur in accordance with disclosed embodiments.

Figure 6:
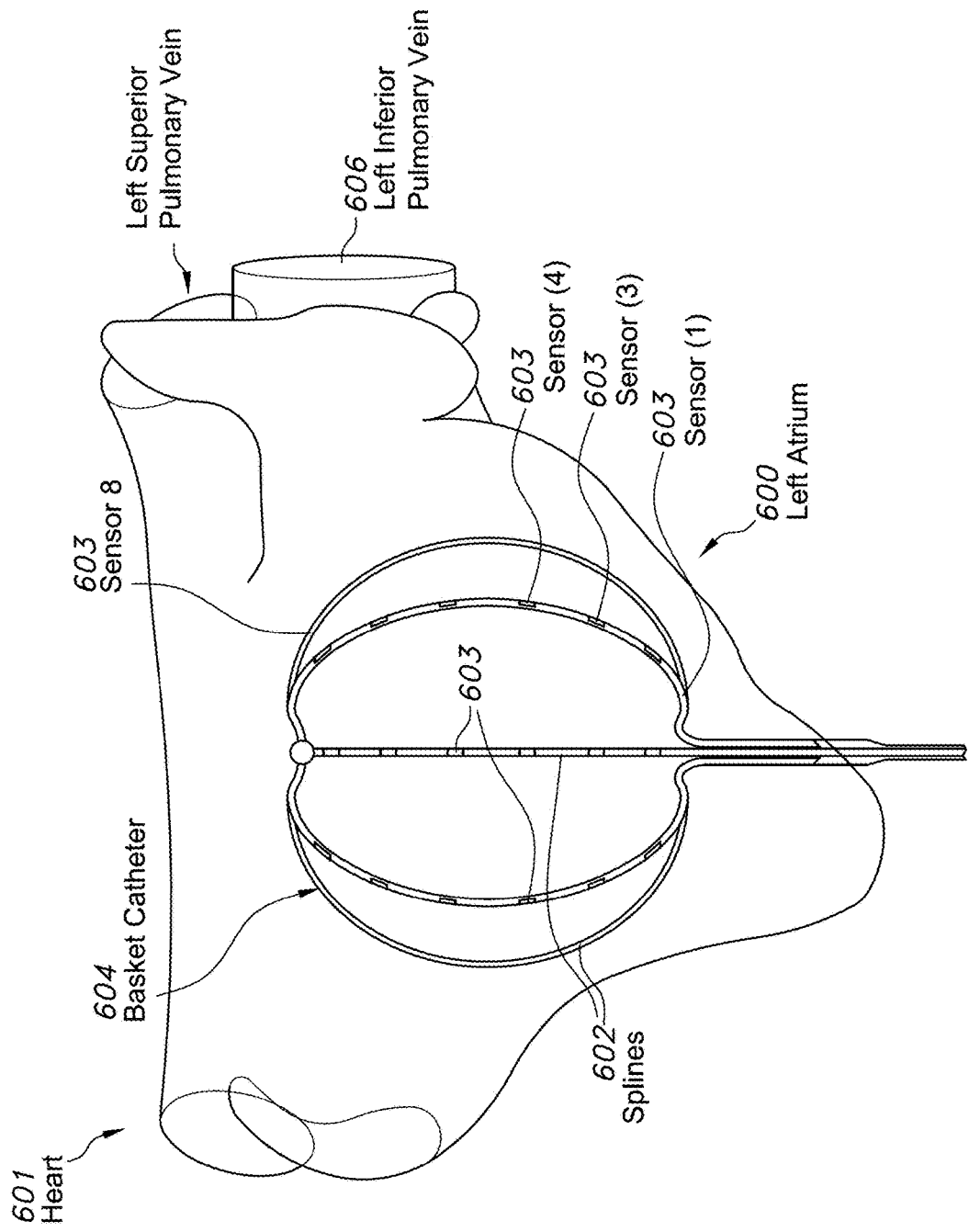
FIG. 6 is an illustration of the basket catheter subassembly as delivered in the left atrium of the heart.

FIG. 6 illustrates the left atrium (600) of the heart (120) with basket catheter subassembly (604) delivered with the catheter guide positioned in the south region of the heart. The splines (605) (designated A-H) are radially expanded with sensors (603) (designated 1-8) located along each spline (605). In the shown embodiment, the catheter subassembly (604) is introduced and delivered into the left atrium (600) of the heart (601) via the right atrium through a puncture procedure through the septal wall, thus gaining access to the left atrium (600) of the heart (120).

Figure 7:
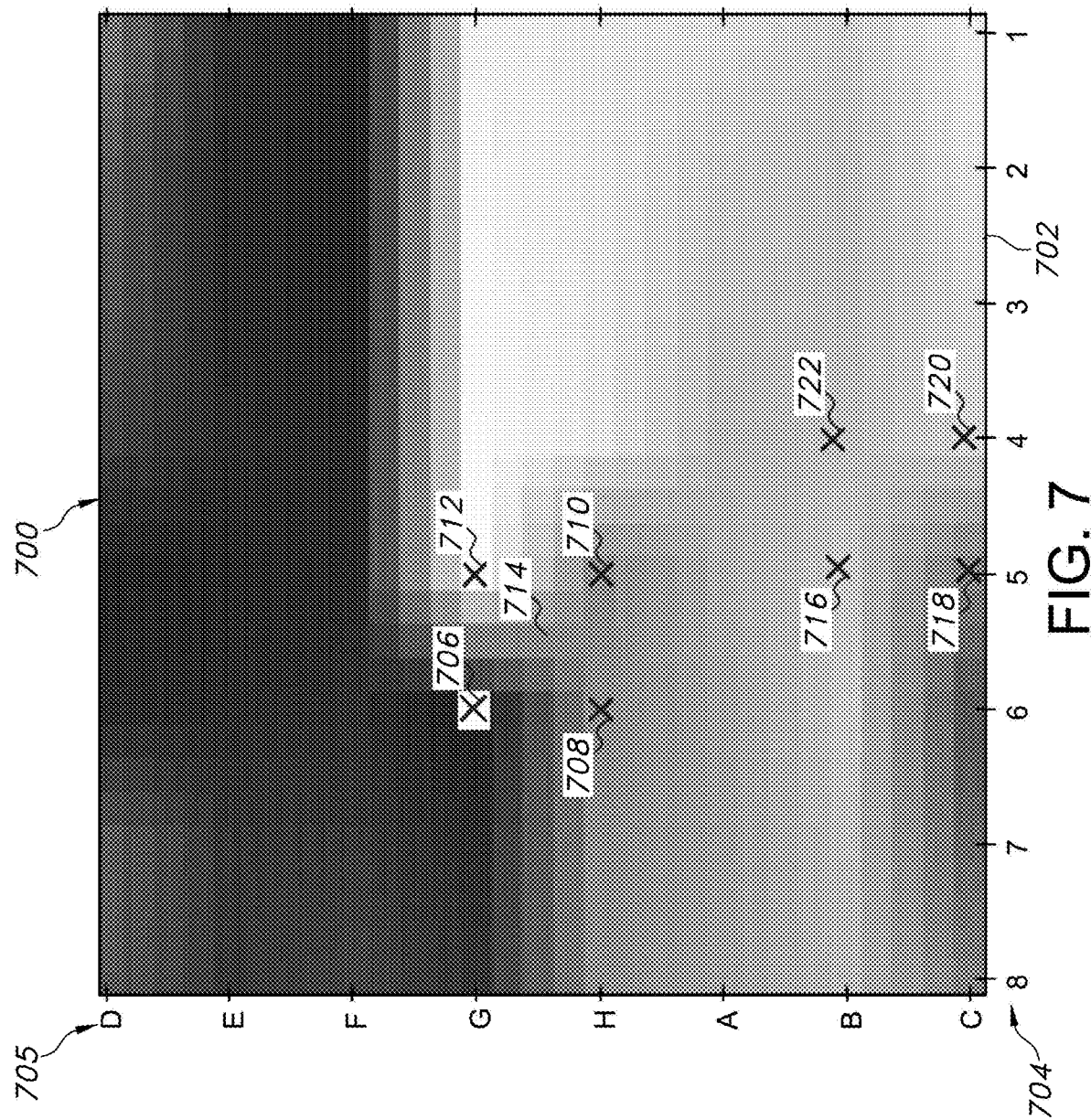
FIG. 7 is an illustration of a 2-dimensional grid mapping a series of activation propagation map (APM) video frames associated with locations of sensor elements.

FIG. 7 illustrates a grid with sensing elements related to locations of sensors illustrated in FIG. 1. FIG. 7 provides an example two-dimensional APM frame 700 of a series of frames (e.g., an APM video 150) that correspond to sequential, evenly-spaced time increments (e.g., every millisecond (msec) or every 10 msec) in a time interval. The time interval can be two-ten seconds, or a different interval. Each APM frame 700 can be generated by sampling multiple MAP signals at time t of the time interval.

APM frame 700 includes a grid 702 having an electrode reference 704 labeled 1-8 and a spline reference 705 labeled A-H. The electrode reference 704 and spline reference 705 have 64 intersecting elements, also referred to as sensor elements, which correspond to respective sensors 104 of the array of sensors (e.g., 64 sensors). For example, sensor elements 706, 708, 710, 712 correspond to respective intersections on the grid 702 (1-8, A-H), and further correspond to respective sensors 104 of the array of sensors. Specifically, the sensor elements 706, 708, 710, 712 are located on grid 702 at intersecting elements that may be labeled (6,G), (6,H), (5,H), and (5,G), respectively.

Grid 702 is segmented into a plurality of areas, with each area defined or bounded by at least three sensor elements. The areas are configured as polygons (e.g., a triangle, rectangle, or square), and some cases can cover the entire grid 702. The sensor elements that define each area are positioned at vertices of the area. An example area 714 is a square having vertices at intersecting elements that may be labeled (6,G), (6,H), (5,H), and (5,G). Area 714 is defined by sensor elements 706, 708, 710, 712 that are positioned at the four vertices of a square (G-H, 6-5). In the example shown, the entire grid 702 is covered by contiguous, non-overlapping square areas, with each square area being bounded or defined by four sensor elements. Area 714 corresponds to an area of the heart 120 defined or bounded by the sensors 104, which correspond to the sensor elements 706, 708, 710, 712. In another embodiment, the areas may overlap. Similarly, an example second area is defined by sensor elements 716, 718, 720, 722, which correspond to respective sensors 104.

The sensor elements of the APM frame 700 are assigned a gray-scale level that corresponds to the voltage (or charge) of the MAP signals. The gray-scale levels for elements located between the sensor elements 706, 708, 710, 712 may be determined using interpolation (e.g., based on the representative MAP signals). U.S. Pat. Nos. 8,521,266, 8,700, 140, and U.S. patent application Ser. No. 13/844,562, which are each incorporated herein by reference in their entirety, describe systems and methods to generate a series of APM frames.

A series of APM frames 700 may be displayed in a sequence, e.g., as a video stream (APM video 150). A viewer may be able to see changes in the represented voltage (or charge) depicted over time. This approach may display either a rotational source or focal source. In this example, the change in voltage has a rotational pattern over time, indicating that a phase singularity has been sensed by sensors 104. More notable are rotational sources or centrifugal patterns (focal sources) that are persistent. Less notable are rotational patterns that are inconsistent, fleeting, and/or non-persistent; they may change rotational direction or precess and/or have an insubstantial degree of rotation. In fact, some of the rotational patterns may not be displayed for a sufficient number of frames to be visible to a viewer, whereas other rotational patterns may be visible, but may then disappear or precess. Despite all of this, the AMP video 150 of APM frames 700 can provide useful information to a surgeon, including dynamic changes over time and the rotational patterns on the grid 702.

In cases when the rotational pattern precesses and may no longer be visible to the surgeon on the 2-dimensional grid 700 display, the disclosed method does provide for a rotational shift of the 3-D catheter model (for example, a representation) on its axis, and permits a viewing on the 2-dimensional grid-display 702 (for example, a representation, whether sensory or clinical representation) at a certain set of user-selected spline-sensor locations at a certain time frame. The rotor may possibly re-appear in full or partial view to the surgeon on the 2-dimensional grid 702 in cases where the rotor is persistent and merely processed and disappeared from the grid 702 view. The disclosed methods are described in greater detail hereinbelow.

Figure 8:
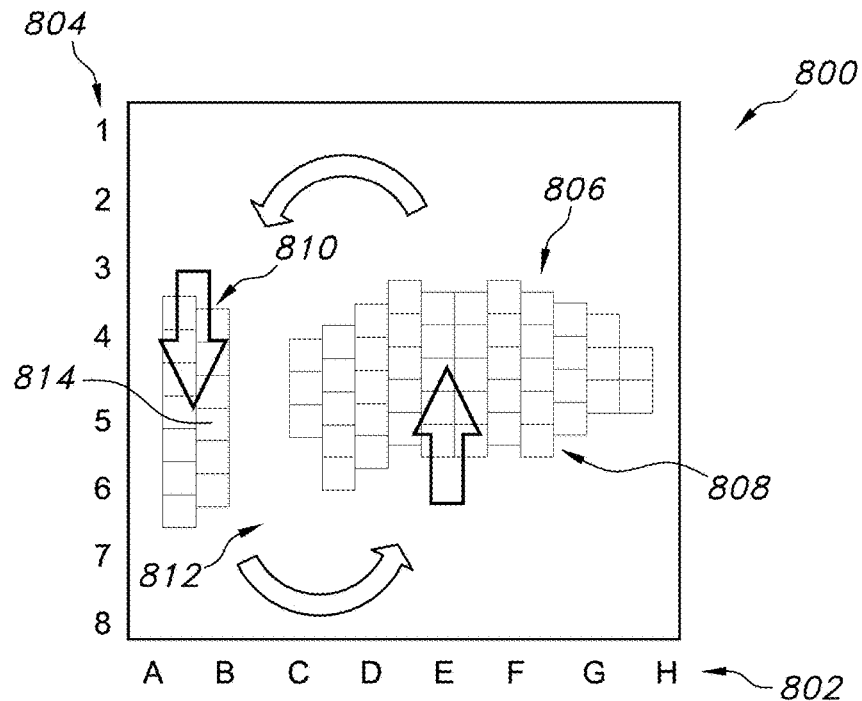
FIG. 8 is an illustration of an example graphical mapping of an example rotational source associated with a heart rhythm disorder in a patient.

FIG. 8 illustrates an example graphical mapping 800 of an example rotational source 806 associated with a heart rhythm disorder in a patient. For example, the rotational source 806 is a source of a heart rhythm disorder in a right atrium of the patient's heart that is observed to progress in a counter-clockwise rotational pattern about a subjective rotation center 812 (one or more of the locations marked with question marks), which can be evaluated by a physician to be along the electrode reference 804, anywhere between about electrodes 4-5-6, and along the spline reference 802, anywhere between about splines B-C, of a basket-type catheter (not shown) introduced into the patient heart. It is noted that the rotational sources of different heart rhythm disorders can be disposed at different locations in different chambers of the heart and can rotate in different directions (e.g., clockwise) about various centers of rotation.

The example rotational source 806 can include a plurality of activation mappings 808, 810 that progress in the counter-clockwise rotational pattern about the subjective rotational center 812 over time of a cycle, e.g., 100 ms-300 ms. Each of the activation mappings 808, 810 can include elements 814 that represent a charge level (or voltage level) of a sensor at a spline reference 802 and a sensor reference 804. The activation mappings 808, 810 represent reconstructed activation information (reconstructed signal data of cardiac signals) identifying activation onset times at a plurality of sensors for one or more beats of a cardiac rhythm disorder (including activations propagating from a rotational or focal source point). For example, the activation mappings 808, 810 can be generated by the system and method for reconstructing cardiac activation information patented in U.S. Pat. No. 8,165,666 and U.S. patent application Ser. No. 13/840, 354, which are incorporated herein by reference in their entirety.

For example, the activation mappings 808, 810 (or activation wave fronts) can be a monophasic action potential (MAP) voltage representation generated for multiple processed cardiac signals shown in FIG. 11 of the '666 patent. Specifically, multiple cardiac signals are processed as described in the '666 patent and MAP representations are generated based on these processed signals. The electrical activity of all the MAP representations can be mapped in a sequence showing the example activation mappings 808, 810 at different time points, e.g., activation mapping 808 being earlier than activation mapping 810. While only two activation mappings 808, 810 (or activation wave fronts) are shown for clarity and brevity of this disclosure, it should be noted that additional activation mappings can be part of the rotational source 806 about the subjective rotational center 812.

Similarly, other systems and methods that can reconstruct cardiac or biological activation information to generate rotational sources can be used as input into the present system and method of identifying the location of a rotational path including remotely located sources relative to the basket splines and/or sensors as positioned in the heart. Also possible, is identifying an approximate core of rotation associated with these rotational sources.

In some instances, a rotational source 806 may have one or more diffuse sections, such as activation wave front 808. The activation wave front 808 generally rotates around the subjective rotation center 812, spreading out diffusely or propagating radially or somewhat radially about a section of the patient's heart, and appears to contribute insignificantly to driving the heart rhythm disorder more significantly than one or more of the other activation wave fronts 810 of the rotational source 806.

Figure 9:
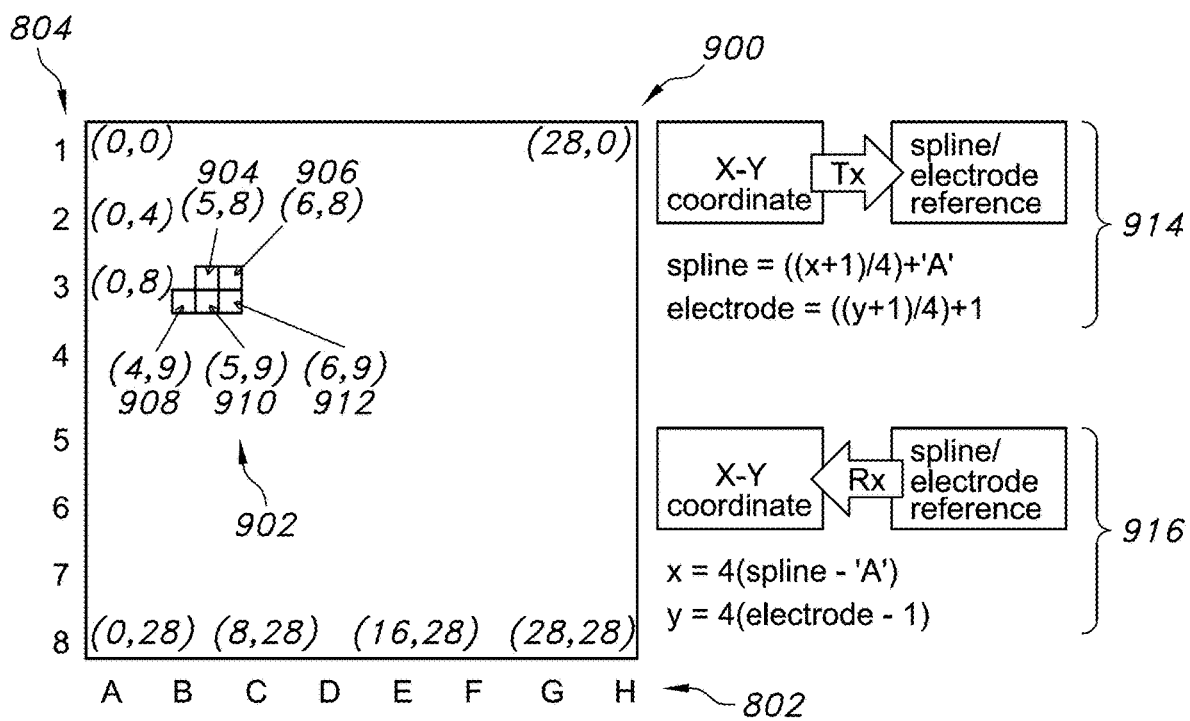
FIG. 9 illustrates an example an x-y coordinate graphical mapping of a spline-sensor element in FIG. 1.

FIG. 9 illustrates an example Cartesian (x-y coordinate) graphical mapping 900. The Cartesian graphical mapping 900 presents an example method of transforming reconstructed signal data of cardiac signals from the spline/electrode references 802, 804 illustrated in the graphical mapping 900 to the x-y coordinates illustrated in this Cartesian graphical mapping 900, [which are implemented in one or more calculations and/or determinations described with reference to 2-D graphical mappings shown in FIGS. 10A-11B. Moreover, additional spline offset and/or spline-sensor offset algorithms may be applied in the case of rotation shift and/or rotational tilt (for example, by generating an angular adjustment to the position of the catheter of the 3-D spline catheter model 1001 (for example, a representation) in two or more directions, as described hereinbelow in connection with FIG. 13 and FIG. 18.

In the shown example, the Cartesian graphical mapping 900 extends from x-y (0, 0) to x-y (28, 28). The example plurality of x-y coordinate locations 902 can represent the element 914 of activation wave front 810 in FIG. 8. The coordinate locations 902 (including locations 904-912) and their associated charge (voltage) levels can be interpolated from the element 914 of the graphical mapping 800. Accordingly, the other elements of the activation wave fronts 808, 810 in FIG. 1 can be similarly transformed to the Cartesian coordinates.

A transformation Tx 914 can transform an x-y coordinate location to a spline-electrode reference. For example, a location at an x-y coordinate (4, 8) can be transformed to the following spline-electrode reference:

$$\text{spline}=((x+1)/4)+A=((4+1)/4)+A=1.25+A=B; \text{ and}$$

$$\text{electrode}=((y+1)/4)+1=((8+1)/4)+1=2.25+1=3.25=3.$$

In some embodiments, the spline-electrode reference values are rounded to a nearest whole spline and whole electrode. In various other embodiments, a fractional spline can be utilized for certain applications.

A transformation Rx 916 is a reverse of the transformation Tx 914. The transformation Rx 216 can transform the foregoing spline-electrode reference to an x-y coordinate location. For example, the spline-electrode location B-3 can be transformed to the following x-y coordinate location:

$$x=4(\text{spline-}A)=4(B-A)=4(1)=4; \text{ and}$$

$$y=4(\text{electrode-}1)=4(3-1)=4(2)=8.$$

In the foregoing examples, the electrodes have the benefit of actual numbers assigned to them. However, the splines have letters assigned. To perform mathematical operations set forth above, the splines are represented by numbers as follows: A, B . . . H represented by 1, 2 . . . 8.

Accordingly, the following spline calculations can be easily performed:

$$A - A = (1 - 1) = 0;$$

$$B - A = (2 - 1) = 1;$$

$$\cdots$$

$$H - A = (8 - 1) = 7.$$

The spline representations can also be used to perform other spline calculations, such as addition, as well as other mathematical calculations as described in the '354 Application, incorporated herein in its entirety.

Figure 10A:
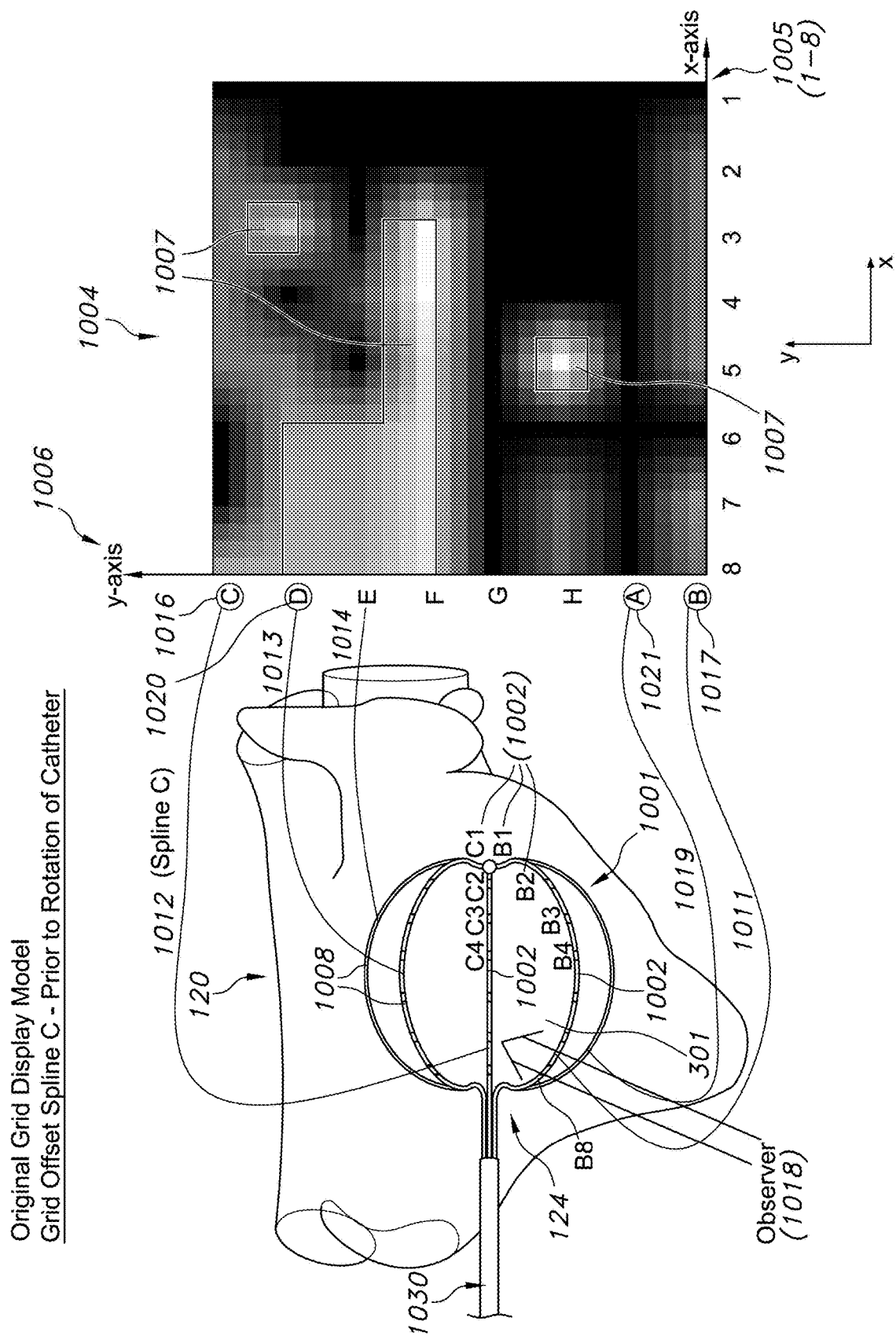
FIG. 10A is an illustration of a basket catheter subassembly as delivered facing the mitral valve of the left atrium of a patient with corresponding grid display.

FIG. 10A is an illustration of a basket catheter subassembly as delivered facing the mitral valve of the left atrium (124) of a patient with corresponding grid display (1004). As shown, the catheter subassembly (301) is positioned with Spline C (1012) facing the mitral valve (205) annulus as shown in the 3-D model (1001) in FIG. 2. The observer (1018) is viewing between splines C and B prior to splitting the 3-D view to form the corresponding panoramic grid projection (1004). The corresponding 2-dimensional grid (1004) depicts the transformed signal data of cardiac signals from each of the spline/electrode references such as for example, described in FIG. 9.

In particular, electrodes designated in the grid (1004) as sensor elements 1-8 (1005) along the x-axis of the grid (1004) and splines A-H (1006) located along the y-axis of the grid, depict the cardiac or biological signals detected by each of the splines A-H (1008) and corresponding sensors 1-8 (1002) located on the surface of each spline A-H (1008). The corresponding mapping of cardiac signals detected by each sensor and spline is shown as (x,y) coordinate points on the x-y plane formed by the grid (1004) (x is the number for each sensor and y is the letter for each spline). Spline C (1012) is translated into grid display (1004) applying algorithms described in detail hereinbelow. Spline C (1012) is shown in grid display as the first corresponding offset spline (1016) upon a split of the 3-D catheter model (1001) but, prior to any rotation or angular tilting of the shaft (1030) of the 3-D catheter model (1001). Spline B (1011) corresponds to the last offset spline (1017) on the y-axis of the grid (1004). Thus, an angular adjustment or tilt to the original position of the catheter model (1001) has been generated.

Performing a split at or between any of the two splines (1008) by application of mathematical algorithms described in greater detail hereinbelow, allows the user to view the cardiac activity of a patient in a comprehensive grid format (1004). A comprehensive video frame of a potential rotational source, rotor, repetitive centrifugal source or repeating activations at a particular point(s) in time is/are visible in the transformed 2-D grid (1004) or a series of frames in the grid (1004). In effect, the 3-D model capturing various cardiac signals at each sensor location is sliced into a flattened 2-D grid to allow the user to view and analyze with greater accuracy electrical activity associated with cardiac rhythm disorders and possibly identify rotational sources therefrom.

The disclosed method provides an accurate close-up and 2-D view of processed cardiac signals so that the rotational sources are more easily identifiable by the surgeon in the grid (1004). The 3-D basket catheter model (1001) has not yet been rotated in this particular figure. As shown in the grid (1004), the lighter and lightest portions as delineated within bounded portions (1007) are indicative of areas representative of more significant activations (possibly of greater intensity too), repeating activations (including activations propagated from centrifugal sources), focal sources and/or rotational source(s) associated with cardiac rhythm disorders. The darker portions of the grid (1004) located outside the bounded portions (1007), show insignificant or no activations.

In this particular embodiment, the surgeon has located activity associated with a potential source of a cardiac rhythm disorder within outlined portions (1007) (e.g. a rotor or rotational source) or at least substantial activity indicative of repeating activations, activation onsets and/or a potential activation trail(s) of activation onset times that are generally indicative of areas associated with sources of cardiac rhythm disorder(s) and that may require ablation treatment if they are repetitive and determined to be the driver, the inner core of the source(s) and/or the source(s) of cardiac rhythm disorder in the patient.

Figure 10B:
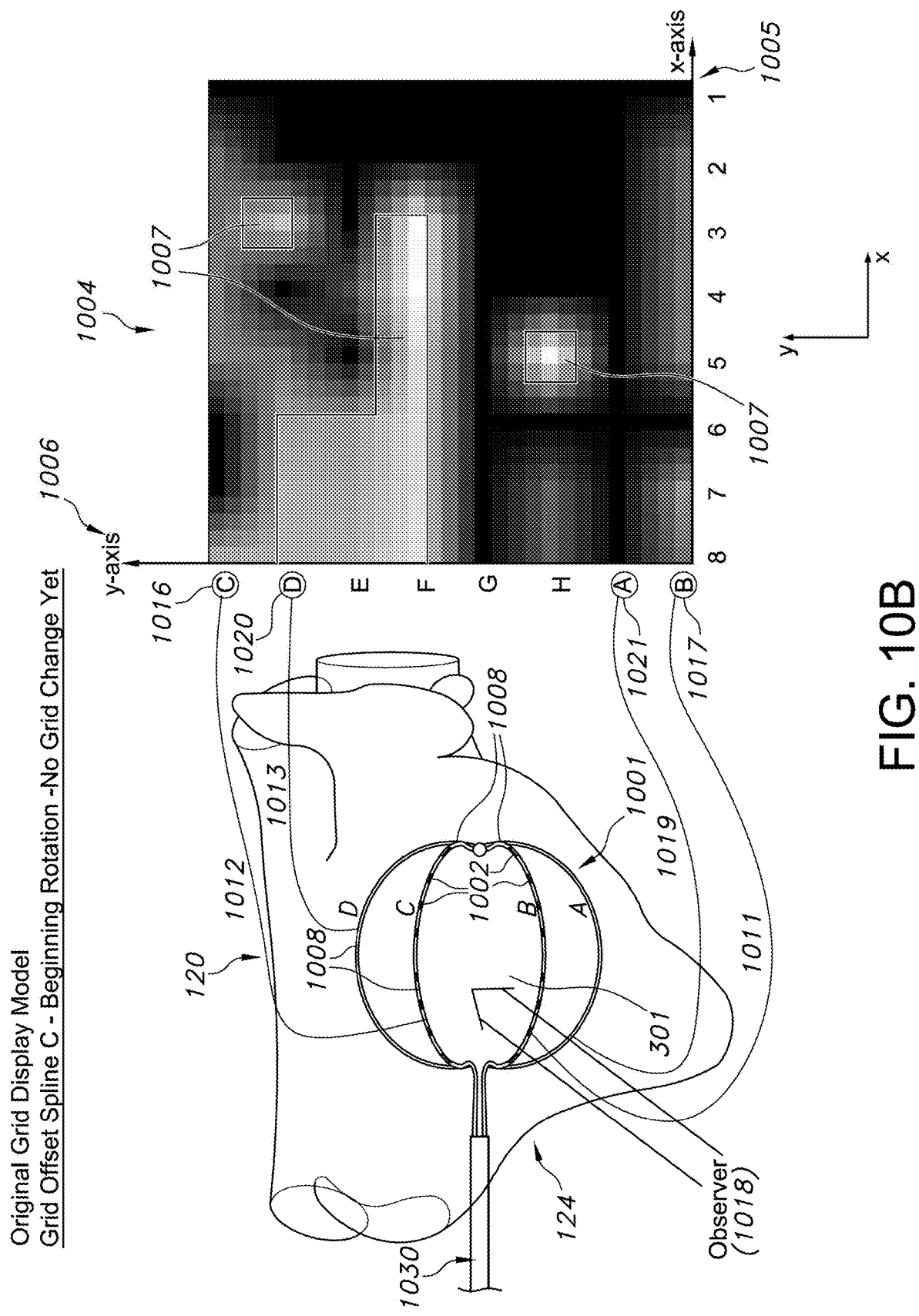
FIG. 10B is an illustration of the basket catheter subassembly as delivered facing the mitral valve of the left atrium of a patient with corresponding grid display in which rotation of the 3-D catheter model commenced.

FIG. 10B is an illustration of the basket catheter sub-assembly (301) as delivered facing the mitral valve of the left atrium of a patient with corresponding grid display. FIG. 10(*b*) shows the commencement of a rotation of the catheter model (1001) in either a clockwise or counterclockwise direction. As shown in corresponding grid (1004), there is no significant shifting of lighter bounded portions (1007) and therefore, demonstrates that the grid will not shift unless the 3-D model rotates and splits the view at or approximately near one of the splines such that the splines are shifted upon translation to the grid display at the y-axis spline elements (1006).

In both FIGS. 10A and 10B, splines designated C, D, A, and B (1012, 1013, 1019, and 1011, respectively) correspond, once translated, to grid y-axis elements (1006) at points 1016, 1020, 1021 and 1017, respectively.

The grid (1004) as shown in both FIG. 10A and FIG. 10B may represent, for example, transformed reconstructed signal data of cardiac signals from each of the spline/electrode references (1008) and (1002). Spline C (1012) in grid display (1004) is shown in this embodiment as the first corresponding offset spline (1006) prior to any rotation or angular tilting of the 3-dimensional catheter model. Even after a small rotation of the 3-D catheter model (1001) of FIG. 10A, the snapshot of grid (1004) remains static to the observer in FIG. 10B. The lack progression shown in the grid display (1004) of FIG. 10B, is illustrative that the rotation of the 3-D catheter model (1001) must be greater than or equal to a pre-determined threshold, such that rotation above the threshold shifts the observer's (1018) (that is viewing the model between two splines) viewpoint to the next spline. Therefore, once the rotation of the 3-D catheter model (1001) is determined to be greater than or equal to such a threshold, it will effect an offset change of corresponding y-axis spline elements (1006) on the grid (1004) (for example, a grid representation) which essentially, results in a split of the observer at or near one of the splines (1008) in the observer's range of view (1018) of the 3-D model (1001). A rotation that produces the next offset in the consecutive spline elements (1006) of grid (1004) (for example, a grid representation as displaced resulting from a perturbation applied thereto causing an offset by at least one displacement unit), can be realized by rotation of the 3-D model (1001) anywhere between 0°-360° degrees (for example, in offset units in a first direction). As an example, the user may rotate the 3-D model just 5° degrees, and that may be sufficient to cross the threshold that effects a shifting or displacement of the splines (1006) on the grid (1004) due to the rotational perturbation applied by the unit of angular displacement.

As already described, it is noted that in certain embodiments the sensors are spatially arranged with respect to the patient's heart (120) and therefore any corresponding array of sensors of the catheter used to reconstruct activation information or processing of electrical cardiac signals may cover different portions of the heart (120). Since the heart (120) is not a uniform or planar structure, the spatial arrangement of electrodes or sensors in such an array can be varied with respect to the shape of the heart (120) to improve the detection of electrical signals or activity in the heart (120). Different catheters with various spatial arrangements of the sensors in the sensor array may also be used, such as spiral, radial spokes or other spatial arrangements.

Also, as described in connection with FIG. 4 of U.S. Pat. No. 8,594,777, incorporated herein in its entirety, is an example array of sensors of catheter and an example selection of signals from the sensors to reconstruct cardiac activation information (e.g. activation onsets). The number of neighboring signals for a given analysis signal can be fewer or greater depending on the spatial arrangement of the sensors in the array, the chamber of the heart analyzed and the heart rhythm disorder under treatment.

Therefore, depending on the user's frame of reference in viewing the 3-D model (1001), the actual degree of separation of each of the splines (305) on the actual catheter sub-assembly (301) as delivered in the patient's heart (120), and other factors described above, these factors may impact the degree of rotation required to cause a split at the splines (1008) on the 3-D model (1001) and a corresponding shift in the translated grid y-axis spline elements (1006).

Figure 10C:
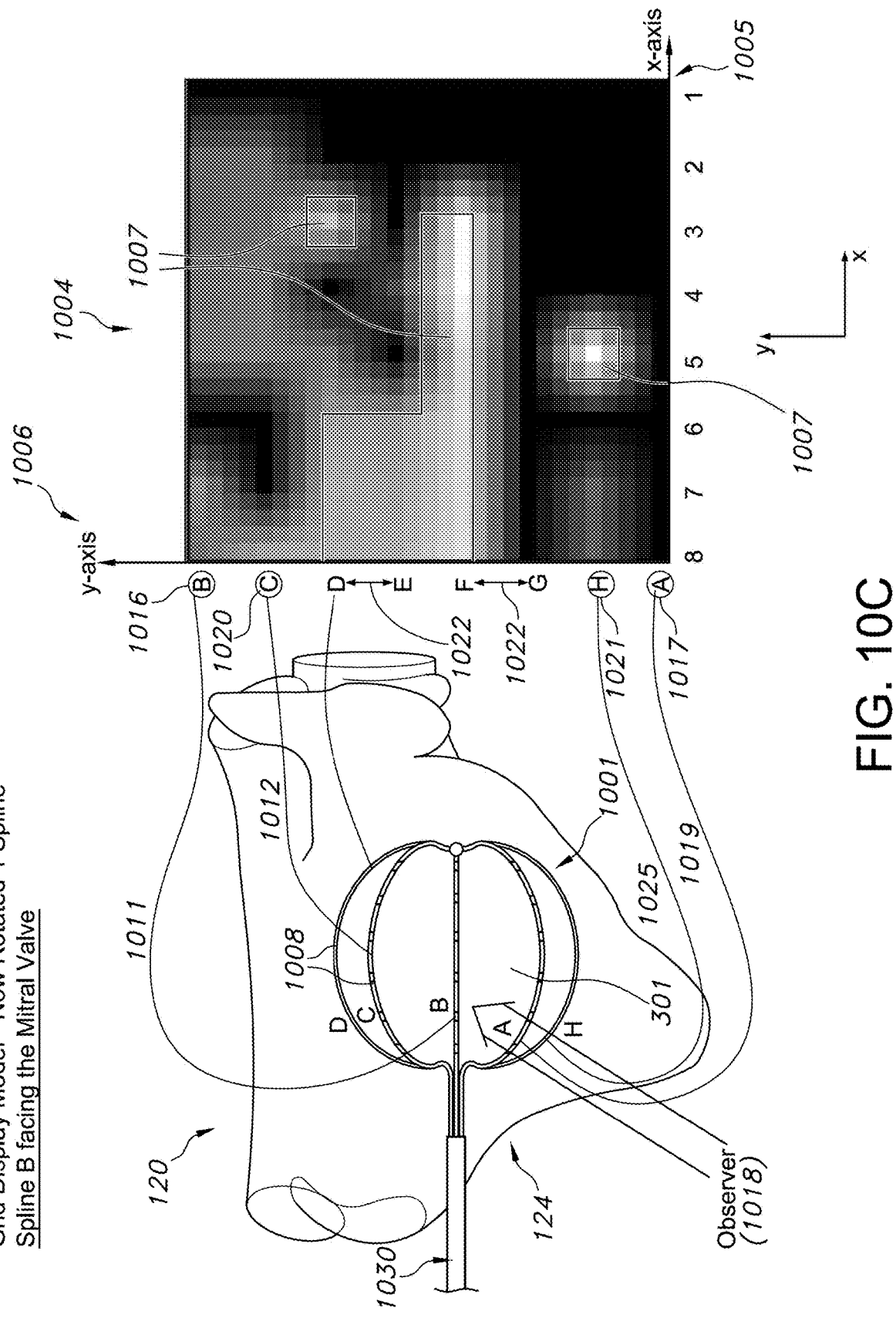
FIG. 10C is an illustration of the basket catheter subassembly as delivered facing the mitral valve of the left atrium of a patient with corresponding grid display after one spline rotation of the 3-D catheter model.

FIG. 10C is an illustration of the basket catheter sub-assembly (301) as delivered facing the mitral valve of the left atrium (124) of a patient with corresponding grid display after one spline rotation of the 3-D catheter (1001) model. FIG. 10C shows the 3-D catheter model (1001) after rotated one-spline rotation clockwise (relative to FIG. 10A), resulting in Spline-B facing the mitral valve (201). As shown in corresponding grid (1004), the lighter bounded portions (1007) indicating greater areas of activations and/or other activity such as rotational activity of activations that rotate for example, in sequence for at least a first time period; centrifugal propagation that emanates for example, for at least a first time period; or focal source identifiable for example, for at least a first time period, have also shifted in a downward direction at least one spline segment (1022). This further illustrates the point that the grid elements found in grid (1004) will not shift unless the 3-D model rotates above a predetermined threshold sufficient to split the view of the observer at or near one of the splines. The spline elements (1008) will shift upon translation to the grid display as indicated at the y-axis spline elements (1006).

In FIG. 10C, splines designated B, C, H and A (1011, 1012, 1025 and 1019) once translated to grid (1004) correspond to y-axis elements (1006) at points 1016, 1020, 2021, and 1017, respectively). The split as translated to the grid (1004) is apparent between splines B (1016) and A (1017) as visible on the grid (1004), respectively.

Figure 10D:
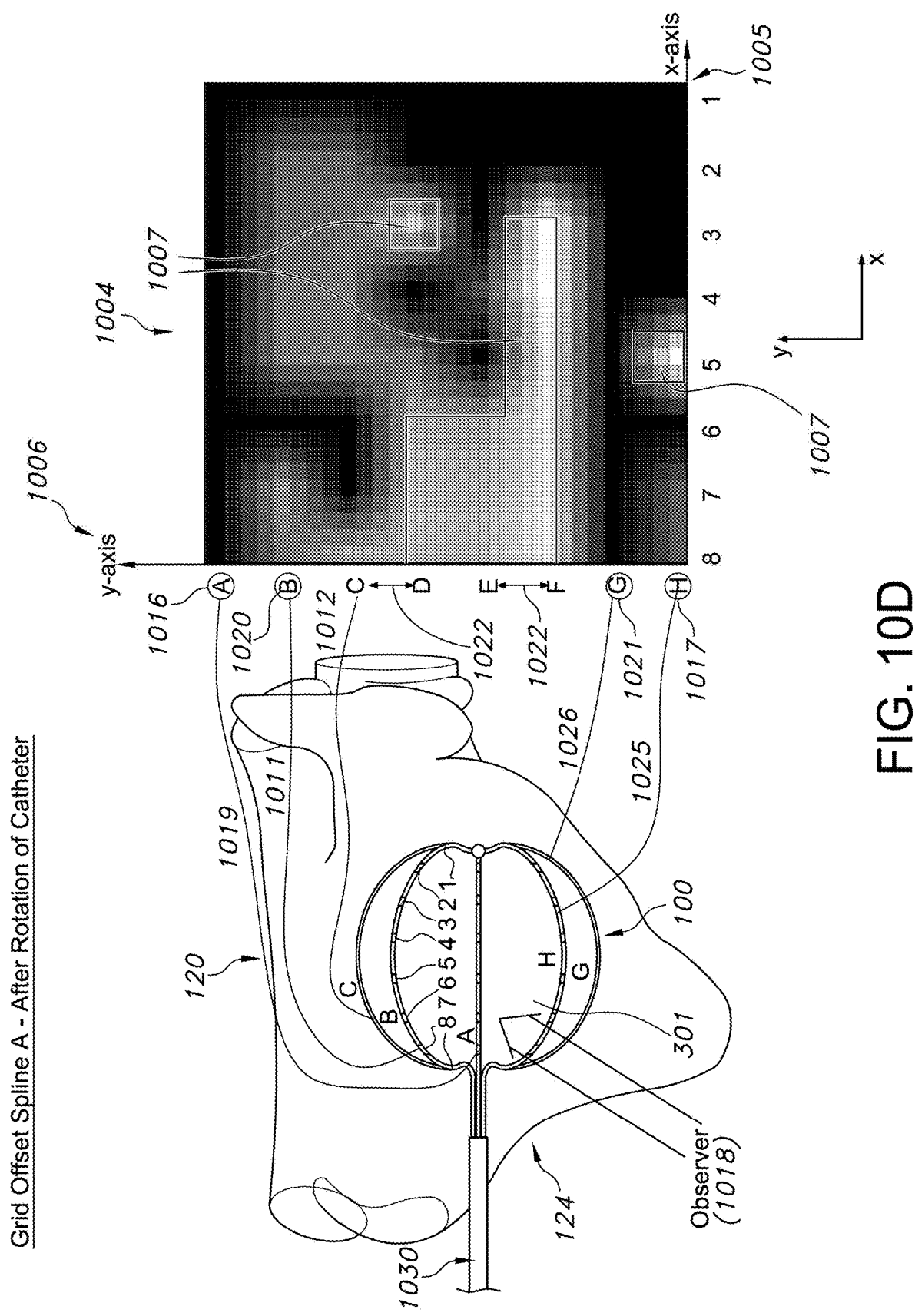
FIG. 10D is an illustration of the basket catheter subassembly as delivered facing the mitral valve of the left atrium of a patient with corresponding grid display after one spline rotation of the 3-D catheter model from FIG. 10C.

FIG. 10D is an illustration of the basket catheter sub-assembly (301) as delivered facing the mitral valve (205) of the left atrium (124) of a patient with corresponding grid display after one spline rotation of the 3-D catheter (1001) model relative to FIG. 10C. FIG. 10D shows the 3-D catheter model (1001) after rotated one-spline rotation clockwise (relative to FIG. 10C), resulting in Spline-A (1019) facing the mitral valve (201). As shown in corresponding grid (1004), the lighter bounded portions (1007) indicating greater areas of activations and/or other activity such as rotational activity, centrifugal activity or focal source, have also shifted in a downward direction at least one spline segment (1022).

In FIG. 10D, splines designated A, B, G and H (1019, 1011, 1026, and 1025) once translated to grid (1004) correspond to y-axis elements (1006) at points 1016, 1020, 2021, and 1017, respectively. The split as translated to the grid (1004) is apparent between splines A (1016) and H (1017), respectively as visible on the grid (1004) at those points.

As indicated in the grid displays of both FIGS. 10A-10D using a gray-scale level for activity between sensors, the lightest portions of bounded areas (1007) are generally areas that indicate more significant electrical activity and/or changes in the represented voltage (or charge) depicted at a particular time interval. However, a viewer of a series of APM frames in video format as depicted in one frame on a grid display (1004), may be able to see rotational activity over time. The APM video of APM frames does provide useful information to the surgeon including dynamic changes over time and the rotational patterns on a grid display (1004) of MAP (monophasic action potential) voltage representation generated for each processed signal. FIG. 11 as described in the '666 patent illustrates monophasic action potential (MAP) voltage representation generated from each processed signal. Multiple signals may be processed and MAPs generated based on the processed signals. The electrical activity of all MAPS is mapped into a sequence of example activation mappings to show activation onsets.

Figure 11A:
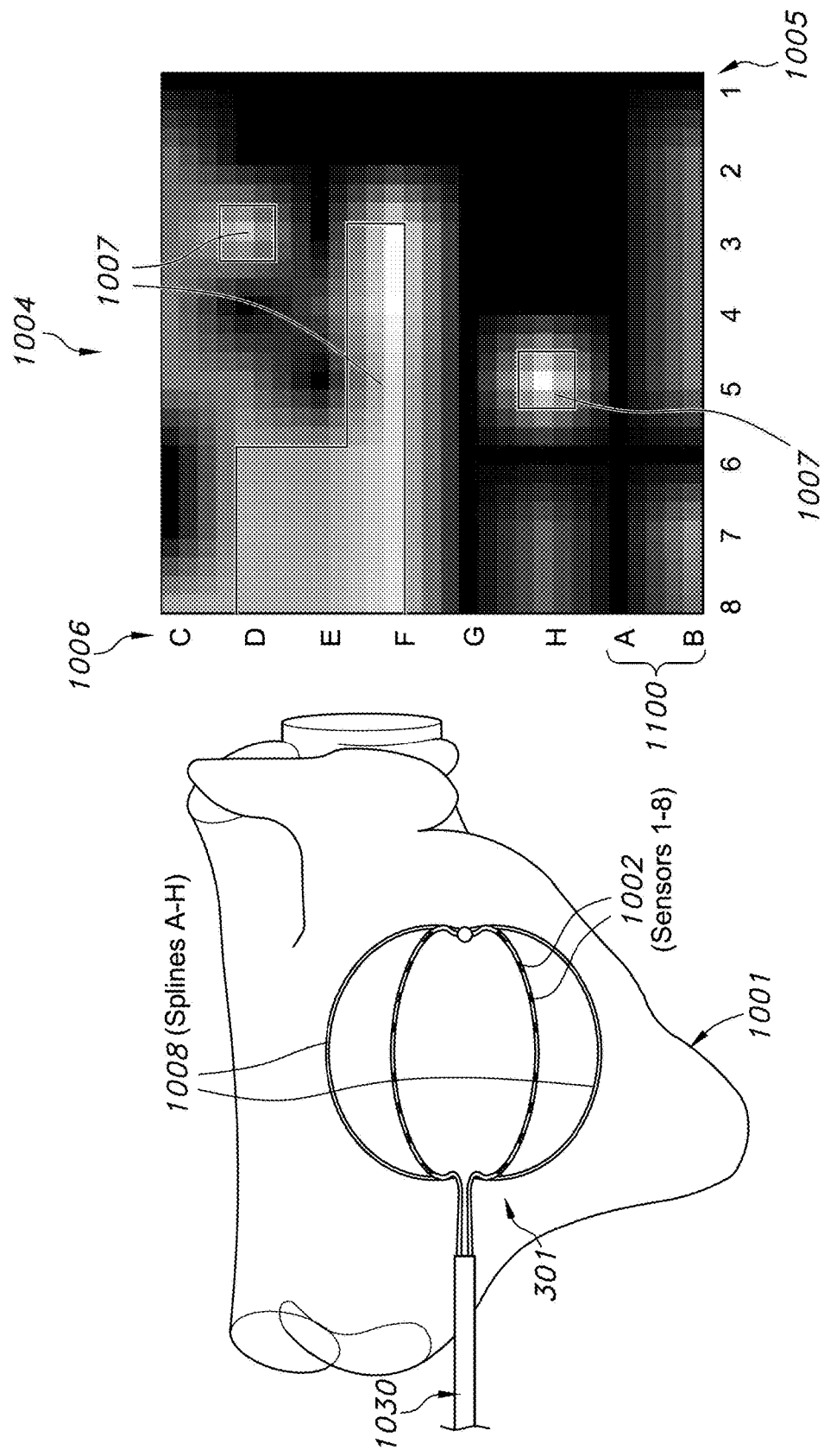
FIG. 11A is an illustration of the basket catheter subassembly as deployed facing the mitral valve of the left atrium of a patient with corresponding grid display.

FIG. 11A is an illustration of the basket catheter sub-assembly as imaged once delivered facing the mitral valve of the left atrium of a patient with corresponding grid display (1004). This illustration is prior to the rotation of the 3-dimensional catheter model 1001 as originally delivered in the heart (120) of the patient by the surgeon. It is noted that generally, the actual catheter sub-assembly (301) is not rotated once positioned against the interior walls of the atrium of the patient's heart (120). However, the catheter imaged model (1001) is able to be rotated so that the sensor-spline signals are shifted accordingly on the grid display (1004) depending on the chosen direction to rotate the 3-dimensional model. In addition, the view is split to capture activity of greater interest and translate to the corresponding grid (1004). Such splitting between two splines from the 3-dimensional view can be generated at any of the splines and/or at any of the sensors of the user's selection. The corresponding grid-offset view is a "flattened" view of the 3-dimensional model which is split between two splines and translated to its corresponding 2-dimensional form at each corresponding spline-sensor location. Various factors may affect the user's selection to rotate the 3-dimensional globe in one direction verses another direction as well as to split the view between two particular sensors. The user may generally be inclined to rotate or split the view between two splines and/or sensors in order to identify as visualized, the rotational source on the grid (for example a representation in which activations rotate in sequence at least once or for at least a time period. In certain embodiments, this visualization may be the driving factor in determining the direction chosen by the user to apply a rotational shift, two-dimensional shift and/or an angle of tilt to the catheter model (1001).

In addition, in other embodiments of the present disclosure, the 3-dimensional model may be generated with a particular tilt applied at a particular angle in order to locate particular electrical activity that was otherwise, visually incomprehensible or non-discernible to the viewer and not indicative of, for example, a rotor that, for example, rotates at least once, or a rotational source, for example, when it rotates at least once or activations rotate in sequence for at least a first time period. These instances usually occur when a rotor or rotational source is located in a remote region relative to the original delivery of the catheter sub-assembly (301) into the regions of the heart (120). These types of instances are referred to as edge conditions. For example, such edge conditions may be characterized by a rotor that may persist along an edge, perimeter or even a polar region of the heart that is otherwise unrecognizable or undetectable with the original placement of the catheter subassembly (301). Thus, in such cases, the rotor is not detected or otherwise, identifiable at any of the respective locations of each sensor/spline as lodged in place against the walls of the heart (120) during the procedure. In such cases, there may be seen dispersed random electrical activity rather than any rotational activity (whether persistent or not) associated with a rotational source or rotor.

Figure 11B:
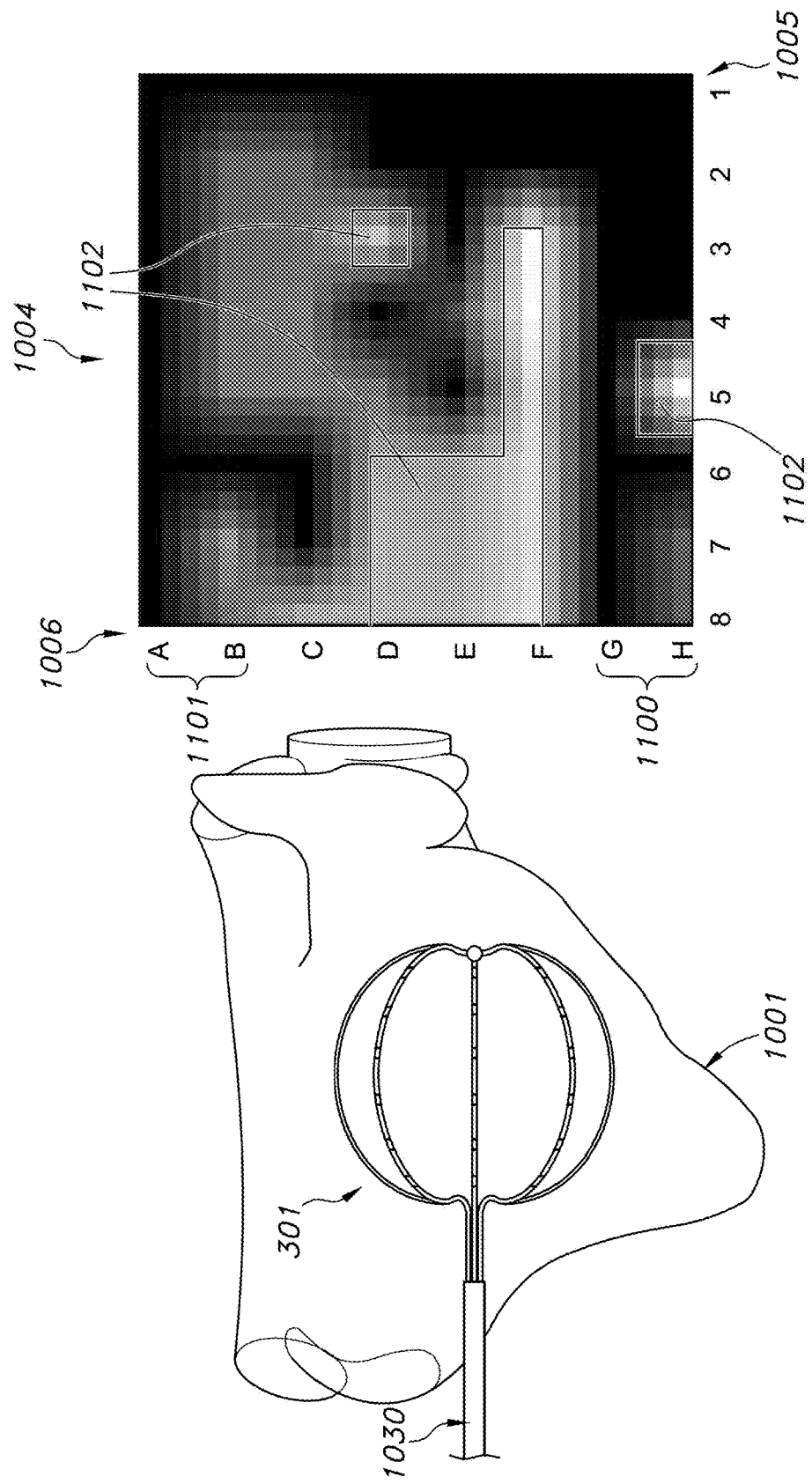
FIG. 11B is an illustration of the basket catheter subassembly of FIG. 11A after rotation of the 3-dimensional catheter model.

FIG. 11B is an illustration of the basket catheter sub-assembly of FIG. 11A after rotation of the 3-dimensional catheter model (1001) (rather than rotation of the physical basket catheter sub-assembly (301) as delivered in the patient's heart (120)). In the shown embodiment, the representation is rotated as illustrated in the 3-dimensional catheter model (1001) such that splines A-H shift on the corresponding grid (1006) in a downward direction. In this particular embodiment, splines A and B originally shown at the bottom of the grid at 1100 of FIG. 11A, have since been shifted (for example, displaced at least one spline-sensor unit) to the upper portion of the grid (1004) at position (1101) of the spline axis of the grid (1006) of FIG. 11B. The rotational shift of the 3-dimensional catheter image model directly corresponds to a translation or offset (for example, displacement of the catheter model representation) of the corresponding grid display (1004) in a particular direction (for example, a displacement of the grid representation in one or more directions). Additionally, the lighter portions generally indicating greater electrical activity as shown in (1007) of FIG. 11A, have shifted towards the bottom portion of the grid (1004) as shown in outlined areas (1102) of FIG. 11B.

Figure 12A:
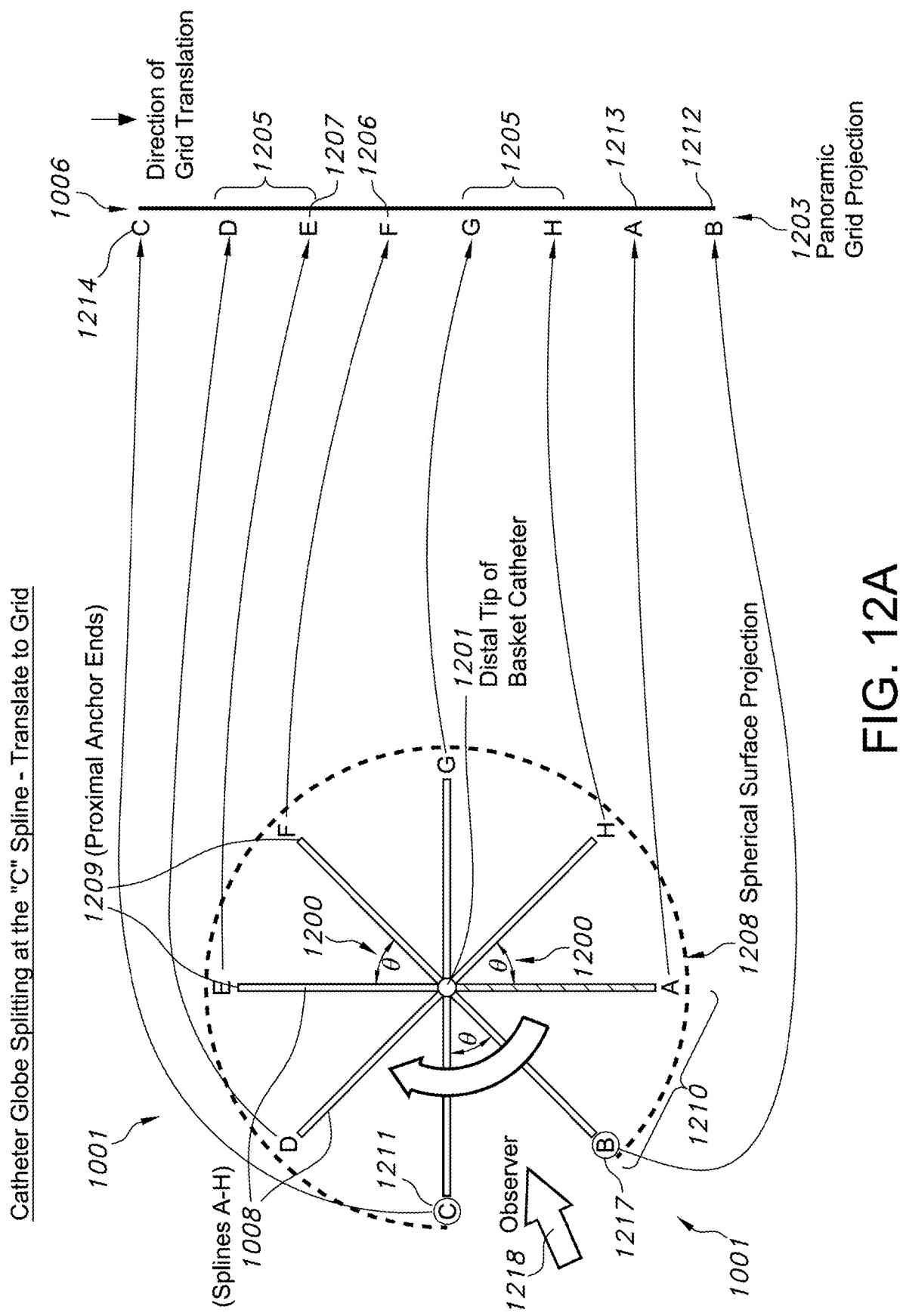
FIG. 12A illustrates a top view of the catheter subassembly with radially extended splines as aligned prior to rotation of the 3-dimensional catheter model.

FIG. 12A illustrates a top view of the 3-dimensional (3-D) model of the catheter sub-assembly (301) depicting splines A-H prior to any rotation of the 3-D catheter model. This is an initial static state of a series of frames representing cardiac signals obtained from the sensors spatially associated with the patient's heart (120). As shown, the splines (1008) are joined at the distal tip (1201) of the basket catheter (1001).

The sensors along each spline (1008) detect the cardiac signals that are processed and analyzed by the surgeon. The angles θ (1200) existing between each radially extended spline (1008) are shown as having approximately a 45° angle. Therefore, the eight splines (1008) designated A to H, respectively, are separated by an angle θ (1200). Such a relationship is a predetermined angular relationship (also subject to variability) used to generate a symmetric or substantially symmetric 3-dimensional model of the catheter model (1001). Such symmetry is implemented in generating a mathematically related translation of retrieved cardiac or biological signals to resultant panoramic grid projections (1203).

The shown embodiment depicts the 3-dimensional catheter model with an applied split of the 3-D model at approximately the location of spline C (1211) in the reference catheter model (1001). The splitting generally occurs from the perspective of the observer's viewpoint (1218). The observer's viewpoint (1218) lies approximately between spline B (1217) and C (1211) but, after application of respective algorithms (described in greater detail hereinbelow), the split is determined to be closer to the C-spline (1211) and thus, will result at the C-Spline (1211). Therefore, the split at spline C (1211) will be translated to a 2-dimensional panoramic grid (1203) projection of the cardiac and/or biological signals captured by the sensors (1002) along each spline (1008). As shown in the grid axis (1006), spline C (1214) as translated is located at the uppermost portion of the grid spline elements (1006) at point (1214). Spline B (1212) as translated is located at the lowest portion of the grid axis at point (1212). Therefore, a splitting or slicing of the 3-D model view, occurs between splines B and C, and is translated in the grid projection (1203) of the 3-D catheter model (1001) as shown at points (1214) and points (1212).

The radially extended splines (1008) which each extend from the distal tip (1201) to the proximal anchor end (1209), theoretically form the circumference of the spherical surface projection (1208). The panoramic grid (1203) projection may also be shifted along the Y-axis as indicated by spline elements (1006) in a downward direction by shifting or rotating the 3-dimensional catheter model (1001) at least less than or equal to one rotational spline unit (1210) (for example, displacement of the representation in one or more x-y sensor coordinate locations). The 3-D catheter model (1001) may further be rotated more than one rotational spline unit (1210). A point of reference is selected at either the actual location of a spline, approximately near a spline or between two splines at which to split the 3-dimensional model. A resultant transformed panoramic grid projection (1203) is generated from various processed cardiac signals as shown, for example, in the translated grid display (1004) of FIG. 10B. The practitioner can view on the grid display (1004), any electrical activity associated with rotational sources such as a rotor, focal source, centrifugal propagation, radial emanation or other activation activity or other type of dispersal indicative of source(s) of cardiac rhythm disorder(s) including complex cardiac rhythm disorder(s).

Figure 12B:
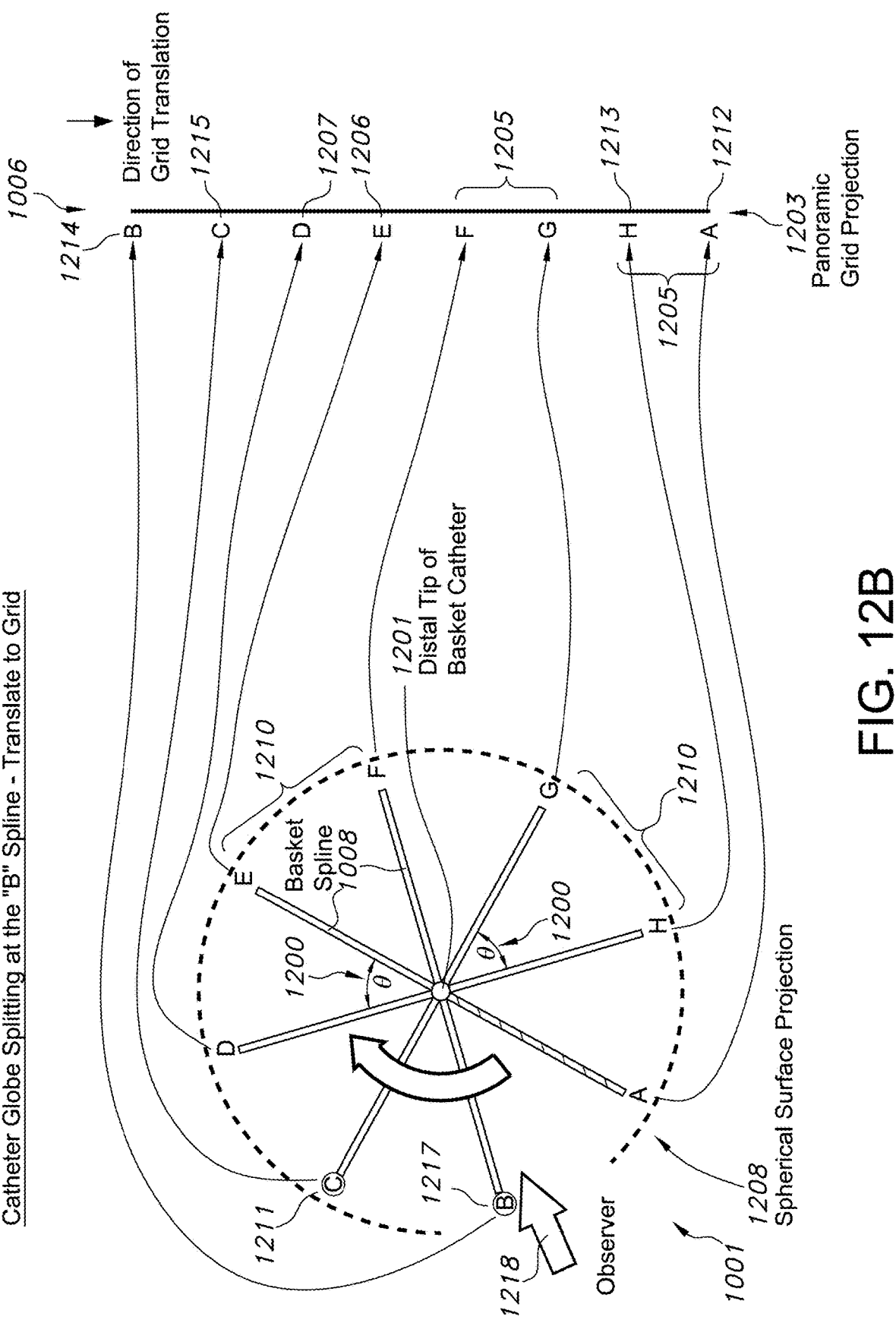
FIG. 12B illustrates a top view of the catheter subassembly with radially extended splines after rotation of the 3-dimensional catheter model in one clockwise unit.

FIG. 12B illustrates a top view of the catheter sub-assembly depicting aligned splines after rotation of one spline unit (1210) of the 3-dimensional catheter sub-assembly model in a clockwise direction. Angles Θ (1200) are also shown having approximately a 45° angle. The eight splines (1008) designated A to H, respectively are separated by the angle Θ (1200). In the exemplary figure, the 3-dimensional catheter model (1001) may be rotated either in one angle units of Θ (1200) or one spline unit or segment (1210). Other variations of rotational units may be implemented as well. The shown embodiment depicts the 3-dimensional catheter model having a split of the 3-dimensional catheter model (1001) at or near Spline B (1217). In relation to FIG. 12A, the 3-dimensional catheter model (1001) is rotated at least one spline unit (1210) or ⅛ of the spherical circumference (1208) unit (1210) in a clockwise direction. The resulting panoramic grid (1203) projection shifts the Y-axis spline elements (1006) from their original orientation shown in FIG. 12A in a downward direction or at least one y-axis spline unit (1205) in a downward direction as shown in FIG. 12B. The directional components and units are representative only and therefore, other embodiments include counterclockwise rotational shifts of the 3-dimensional catheter model (1001) with varying shifts in the translation of the panoramic grid projection.

Spline offset element A originally positioned at lower section (1213) of the y-axis (1006) of FIG. 12A, has since shifted to the lowest section (1212) of grid offset elements (1006) of grid projection (1203). Spline offset element B, originally located at section (1212) of FIG. 12A shifted to topmost section (1214) of grid projection (1203) of FIG. 12B. Spline offset element C originally located at section (1214) of FIG. 12A shifted to section (1215), representing one downward shift of one y-axis spline unit (1205). Spline element E originally positioned in section (1207) of FIG. 12A has shifted down one y-axis spline unit (1205) to position (1206) shown in FIG. 12B. This downward shift in y-axis spline elements (1006) is a result of the observer view (1218) splitting or slicing the 3-D catheter model (1001) at Spline B (1217). This splitting of the view (1218) at spline b (1217) permits flattening of what is otherwise a 3-dimensional non-discernible view of rotational activity such as a rotor and/or centrifugal emanation. The direction of the grid translation is displaced in a downward direction. Spline C (1214) is situated at the top portion of the grid representation, once translated, and spline B (1212) is situated at the bottom-most portion of the grid representation, once translated.

Figure 12C:
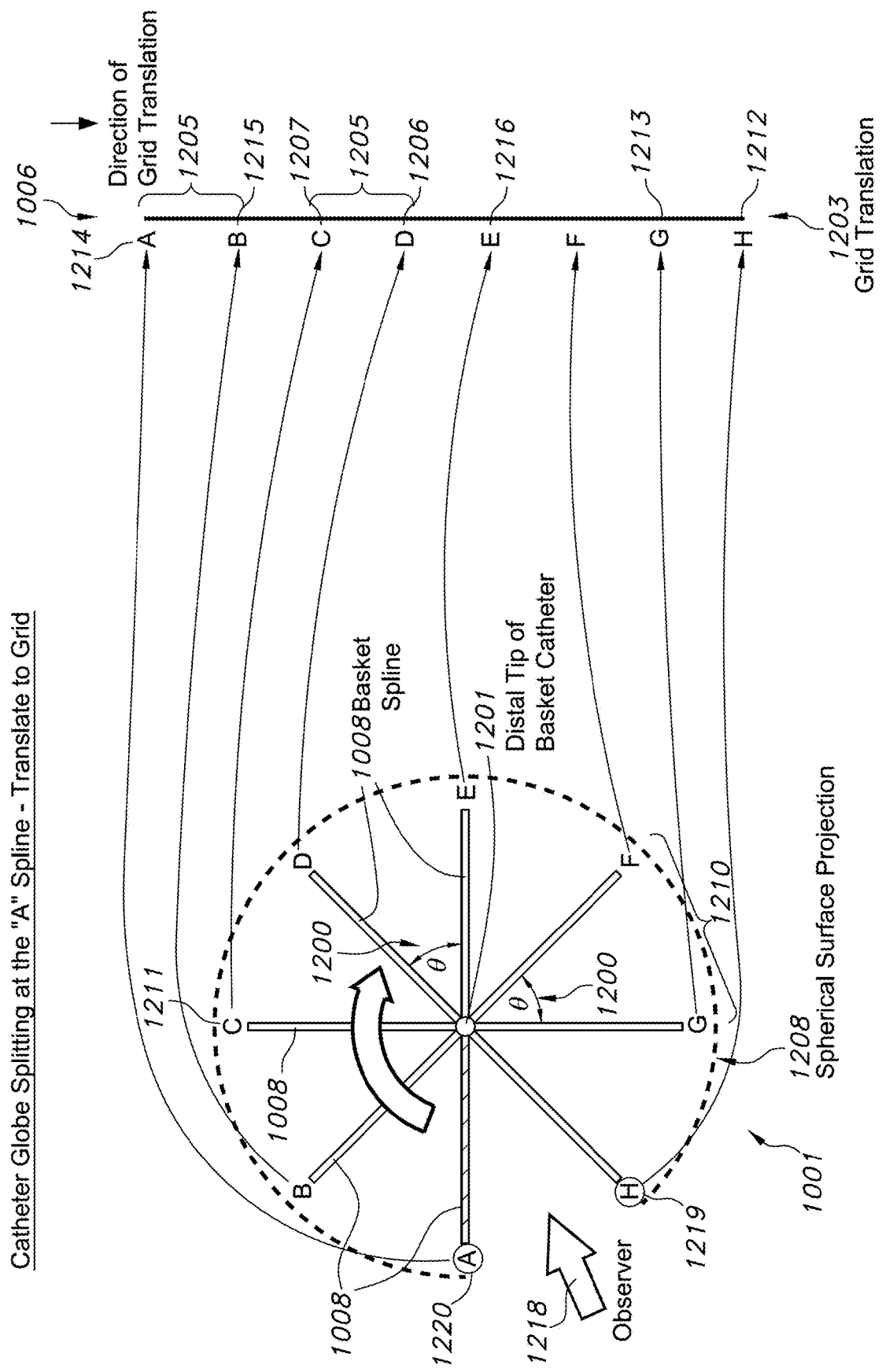
FIG. 12C illustrates a top view of the catheter after rotation of the 3-dimensional catheter model in one clockwise unit.

FIG. 12C illustrates a top view of the catheter sub-assembly with radially extended splines aligned after splitting at the A-spline following a rotation of two spline units (1210) (for example, two offset units displacing the sensor locations in a first unit in a first direction) of the 3-dimensional catheter sub-assembly model in a clockwise direction (using the original static position of 3-D catheter model FIG. 12A as a frame of reference). In the exemplary figure, the 3-dimensional catheter model (1001) may be rotated either approximately in two angle units of Θ (1200) or in two spline segments (1210). Other variations of rotational units (for example, offset units in one or more directions) may be implemented as well in the displacement of the original position of signals of spline-sensors of the 3-D catheter representation. Angles Θ (1200) are also shown having approximately a 45° angle, however the angles may vary in other embodiments. The shown embodiment depicts the 3-dimensional catheter model (1001) with a split of the view occurring at or near Spline A (1220) as shown in FIG. 12C. Using the catheter model (1001) FIG. 12A as an original frame of reference, the 3-D catheter model (1001) was rotated approximately two spline units (1210) or ⅔ of spherical circumference (1208) unit (1210) in a clockwise direction. However, in this embodiment, the 3-D model (1001) is rotated just enough to move the observer to the next 2 splines which effected the downward shift on the grid (1203). Noting the viewpoint of the observer (1218), the observer is closer to spline A (1220) than spline H (1219) but, not by a significant amount, less than one spherical unit (1210). Therefore, the rotation in a clockwise direction is executed until a discrete split of the grid (1203) is effected at Spline A (1220).

The split is performed generally in order to translate the data into a panoramic grid projection with as much data visible to the practitioner in the panoramic grid (1203). The split occurs from the observer's viewpoint (1218) which in this case lies closer to Spline A (1220). Once the mathematical algorithms (noting that other mathematical algorithms are also contemplated in performing the disclosed operations) are applied for performing the split and translation to the grid (1203), the resultant split mathematically is effected at Spline A (1220) in this embodiment. The rotation of the catheter model (1001) results in a panoramic grid (1203) projection with downwardly shifted Y-axis spline elements (1006), two spline elements from their original orientation in FIG. 12A.

However, using FIG. 12B as an original frame of reference, the spline elements (1006) have shifted only one spline unit (1205) in a downward direction. The directional components and units are representative only and therefore, other embodiments include counterclockwise rotational shifts of the 3-dimensional catheter model with varying shifts of units in the 3-dimensional model, which may be implemented to form an ideal translation of the panoramic grid projection with maximum viewing and exposure of relevant signals for the practitioner observing the signals.

As also shown in FIG. 12C, spline offset element A originally positioned at lowest section (1212) of the y-axis (1006) of FIG. 12B, has since shifted to the topmost section (1214) of y-axis grid offset elements (1006). Spline offset element B, originally located at section (1214) of FIG. 12B shifted to section (1215) of FIG. 12C. Spline offset element C originally located at section (1215) of FIG. 12B shifted to section (1207), representing a downward shift of one y-axis spline unit (1205). Spline element E originally positioned in section (1206) of FIG. 12B is shifted or displaced down (for example in the south or negative y-axis direction) by one y-axis spline unit (1205) to position (1216) shown in FIG. 12C.

However, using FIG. 12A as an original frame of reference, the spline elements (1006) have each shifted downward two spline units (1006) with the exception that Splines A & B located in the bottommost sections (1212) and (1213) of grid elements (1006) in FIG. 12(a), have shifted to the top sections (1214) and (1215), respectively of FIG. 12C.

Figure 13:
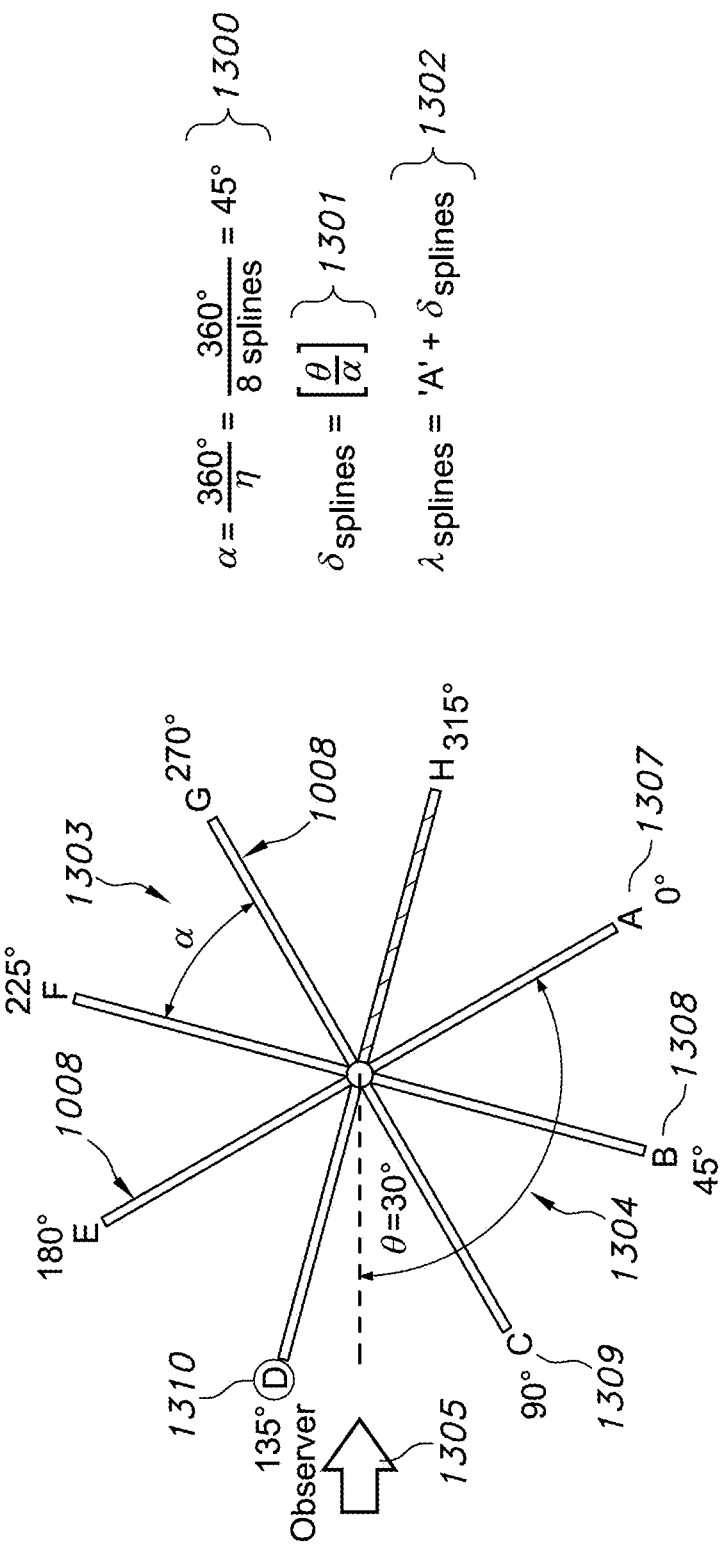
FIG. 13 illustrates an example method of calculating 2-D spline translations to grid resulting from a split of a 3-D catheter model at a spline.

FIG. 13 illustrates an example method of calculating 2-D spline-offset translations to grid resulting from a split of the view of a 3-D catheter model at a particular spline. It illustrates an example set of algorithms that are implemented in performing a split of the 3-D catheter model at a spline-level relative to the observer's view (1305). In addition, this method determines the translation from the roll angle or rotational spline-shift applied to the 3-D catheter model in identifying the source of the cardiac rhythm disorder. In this example, α=the angle between two splines (1303), which can also be variable. In the shown example, there are illustrated eight splines of the basket catheter (301), with α=45°, with application of the value of the number of splines η=8 splines to the formula (1300) as indicated below.

$$\alpha = \frac{360°}{\eta} = \frac{360°}{8 \text{ splines}} = 45° \tag{1300}$$

δsplines is a spline offset value, more particularly defined as an offset number of splines apart that a subject spline is from an arbitrary first spline. This value is considered a discrete spline offset value. As an example, using spline "A" (1307) is an arbitrary first spline located at 0°, the subject "B" spline (1308) is considered to have a spline offset value of 1 or $\delta_{splines}=1$. Spline "C" (1309) has a spline offset value of 2 or $\delta_{splines}=2$ also using spline "A" (1307) as an arbitrary first spline.

$$\delta_{splines} = \left\lfloor \frac{\theta}{\alpha} \right\rfloor \tag{1301}$$

Θ (1304) is a value in degrees of the rotation of the 3-D model (1001) (the basket assembly is shown in its top view (1306) in FIG. 13) relative to the observer's viewpoint (1305). This degree of rotation may also be referred to as the roll angle applied to the 3-D catheter model (1001). A roll angle is applied in order to effect a translation of the cardiac information signals to the 2-D grid (1004) in a centered view or a sufficiently shifted view away from the borders of the 2-D grid. The effect is that the roll angle shifts an originally non-discernible view of the translated cardiac signals such that a source of a cardiac rhythm disorder is identifiable. The roll angle is determined and applied to the 3-D model when the translation or rendering of a source on the 2-D grid was previously non-discernible in the original translation of cardiac information signals obtained from the plurality of sensors (1002). In the shown example, Θ may range from 0° to 359° inclusive. In the shown example, viewing the catheter model (1001) from a distal tip front view (1306), the 3-D catheter model is rotated about the catheter shaft (1030) either clockwise or counterclockwise Θ degrees relative to the position of spline A (1307) located at 0°. As an example, in order to determine Θ (1304) located between splines A (1307) and D, the formula (1301) is applied in the example shown below:

(1301)

$$\delta_{splines} = \left\lfloor \frac{\theta}{\alpha} \right\rfloor \tag{1301}$$

with $\delta_{splines}=3$ (spline offset value between splines A and D) calculated as follows, applying a roll angle of θ=120°.

$$\delta_{splines} = \left\lfloor \frac{\theta}{\alpha} \right\rfloor \tag{1301}$$
$$\delta_{splines} = \frac{120°}{45°}$$
$$\delta_{splines} = 3$$

It is noted that although the value of the roll angle or θ rotates the catheter to an angle that does not quite reach the next spline such that a ceiling function is applied to the calculation. In the shown example, the roll does not rotate the model so that spline D is the resultant spline but, rather the applied calculation takes into account a ceiling function and rounds the value to the nearest spline. In this case, an applied angle of 120° as applied to the formula, renders the value of 3 spline offset values which results in spline D now resulting in the observer's plane of view (1305) where a split will occur.

Note that any values that are calculated beyond 360° for θ are restricted to the following range:
0°≤θ≤360° by application of the formula listed below:
θ=mod(raw angle)

Therefore, by way of example if the raw angle=365°, θ=mod(raw angle) results in θ=5°. For any given raw angle, mod (raw angle) means the resultant angle θ lies between 0°≤θ≤360°. The angles are said to "wrap around" upon reaching a certain angle, in this case 360° is considered the "wrap around" modulus value.

Also shown in FIG. 13 is the concept that the letter of the offset spline can be determined applying the formula (1302) shown below:

(1302) $\lambda\text{spline} = {}^\prime A^\prime + \delta_{splines}$ wherein, A=unicode or ASCII value of the first arbitrary spline letter This value, λspline (1302), is the letter of the offset spline relative to the arbitrary first spline which in the shown example is spline 'A'. The application of this formula generates the displayable alphabetic character of the subject offset spline. Starting with Spline A (1307), the number of offset splines $\delta_{splines}$ (1301), generally implemented in a clockwise direction (but, a counterclockwise direction may also be applied depending on the embodiment) is calculated and applied to the representation. In the illustrated example above, $\delta_{splines}$=3, so applying 3 spline offset units starting from spline A in a clockwise direction, results in an alphabetic spline offset value of spline 'D' (1310). Other algorithms are contemplated that may result in the same displacement of the catheter model representation and in effecting, the shifting and bringing to view in the grid representation, an identifiable source, such as rotational activity at least for one cycle or centrifugal emanation for at least one time period.

Figure 14:
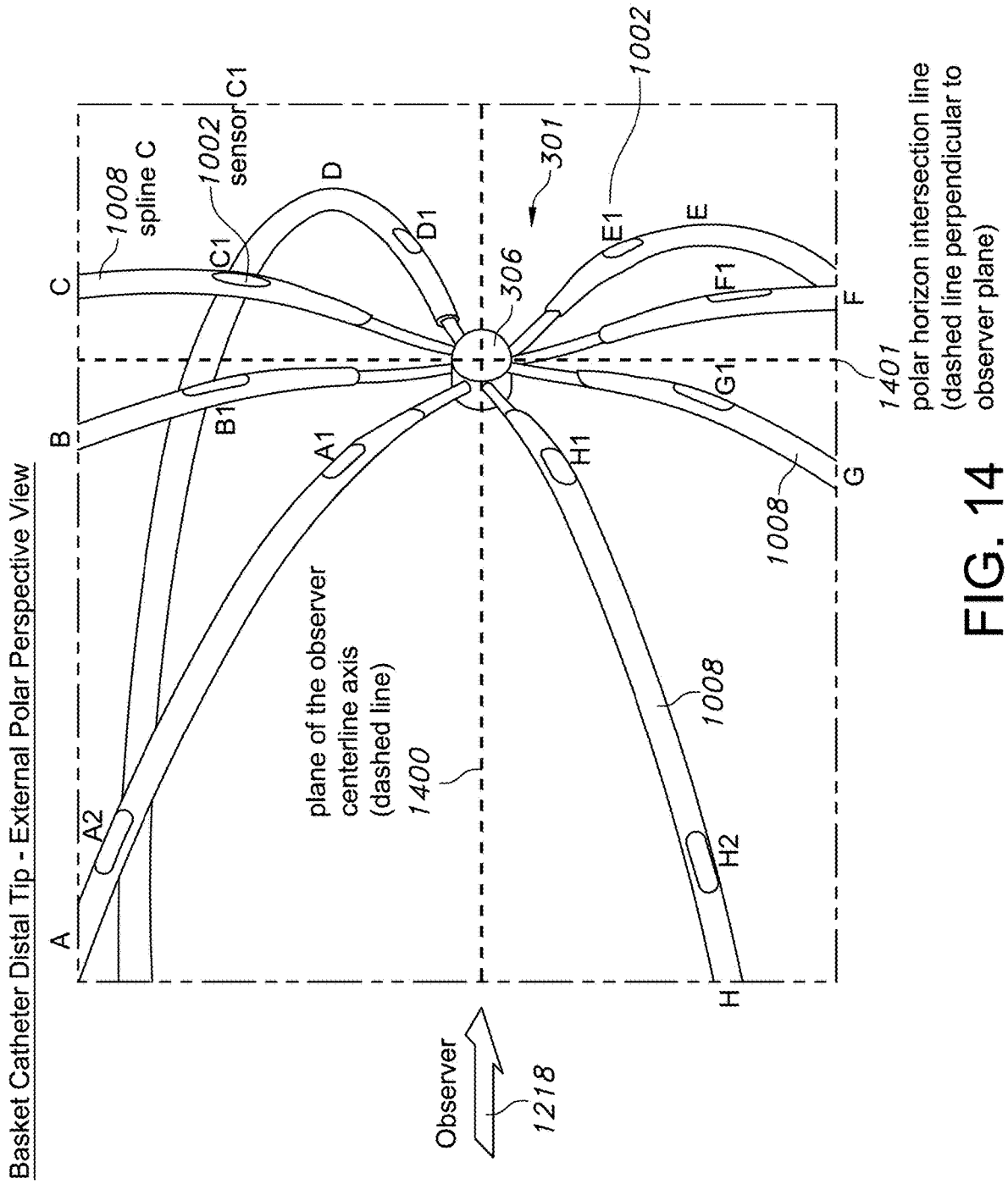
FIG. 14 illustrates a perspective frontal view of the basket catheter sub-assembly showing its distal tip with radially extended splines.

FIG. 14 is a perspective frontal view of the basket catheter sub-assembly (301). The splines (1008) of the basket catheter (301) are secured by a distal tip (306) at one end, i.e. the distal end of the basket catheter (301) and, further secured by a proximal anchor (307) at an opposed end, i.e. proximal end, of the basket catheter subassembly (301) as shown in FIG. 3(*a*). Other embodiments may implement basket sub-assemblies of other configurations.

The plane of the observer is shown as a centerline axis (1400) which forms the theoretical line at which the points on the plane do converge (also when projected onto the 3-D image plane). Each of the splines (1008) designated A-H radially extend from the distal tip (306) of the catheter subassembly (301) outwardly. The polar horizon intersection line (1401) lies perpendicular to the observer's plane (1400). The polar line (1401) generally serves as a guideline when uncovering potential edge conditions located near remote regions of the heart (120) or organ relative to the placement of the catheter subassembly (301), in accordance with methods disclosed hereinbelow. This figure illustrates the relationship between each of the splines (1008), sensors (1002) and the key planes, including the polar horizon intersection line (1401) and the plane of the observer centerline axis (1400).

The location of these guidelines relative to a 3-D catheter model (1001) is implemented in determining the location of a remotely located rotational source or other activity indicative of a source of a cardiac rhythm disorder. These remotely located rotational sources or other remotely located activity, such as polar sources, generally lie in regions of the organ that are not clearly discernible upon deployment of the catheter subassembly (301) into the heart or organ. The location of these sources in considered remote at least relative to the location of catheter subassembly (301) and the corresponding 3-D model of the catheter (1001) which may not clearly indicate initially, any such electrical activations in the heart, electric signals and other activity whether processed or unprocessed, indicative of a source, including rotors, centrifugal, focal or rotational sources. The signals may appear in a corresponding grid or 3-D model (1001), for example, as frayed or dispersed activity along the edges without any coherence of electrical activity and/or activations indicative of a rotor, centrifugal, focal or rotational source.

In accordance with disclosed methods described in greater detail below, the basket (1001) coordinate points such as the plane of the observer centerline axis (1400), the polar horizon line (1401), the location of each spline (1008) (designated A thru H), and/or the location sensors (designated A1 to A8 thru H1 to H8, respectively) (1002) are implemented in identifying the location of the source.

Figures 15A, 15B:
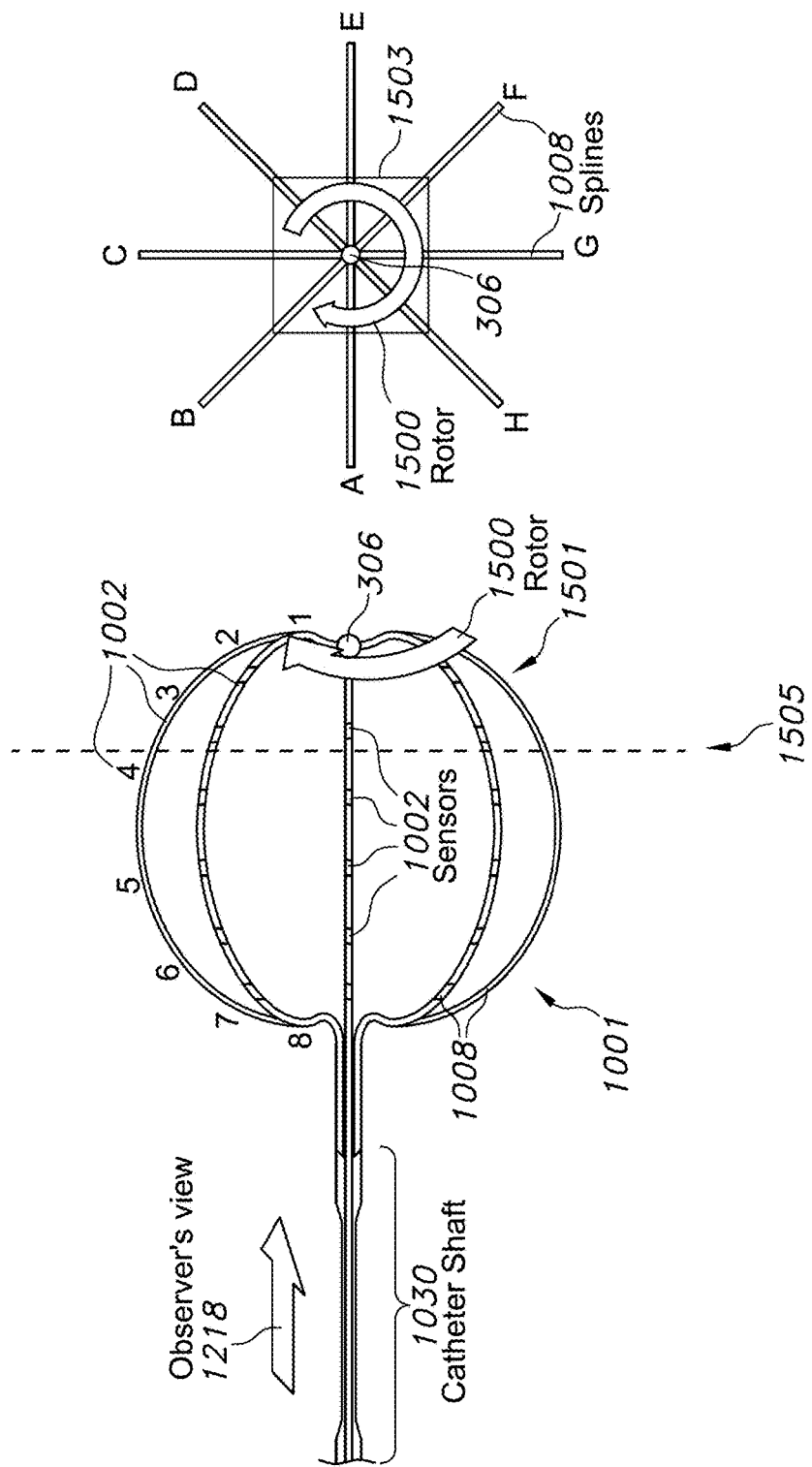
FIG. 15A illustrates a side view of the catheter model showing an example rotor located at a polar region relative to the catheter.
FIG. 15B illustrates a top view of the catheter model showing an example rotor located near the distal tip with radially extended splines.

FIG. 15A illustrates a side view of the catheter model (1001) showing an example rotor located at a polar region relative to the catheter sub-assembly (301). In this example, the catheter (301) is deployed in the atrial chamber where the distal tip (306) of the basket contacts the endocardial surface in a region that coincides with electrical activity exhibited in for example, a rotor (1500). The observer's viewpoint (1218) lies perpendicular to the catheter shaft (1030) but, in this case does not permit an activation wavefront projection in a corresponding grid display (1004) or other display such that it permits viewing and identification of the continuous progression of the wavefront, activations or electrical activity about a particular center of rotation (or even a center point that precesses). The viewer in this example, could not visualize or recognize the rotor, although present in the polar region (1501) located approximately in the area of the catheter model (1001) designated from dotted line (1505) to the distal tip (306), at least with the human eye. In the shown example, the activation wavefront exhibiting rotational activity, focal source or rotor (1500) follows a linear path with interrupted progression each cycle on a view projecting the electrical activity and thus, was non-discernible previously to the practitioner.

This example illustrates the conditions in which a rotor would be considered a "polar rotor" and why it is difficult to visualize the rotor on a grid view projection. Therefore, in accordance with the disclosed methods described in detail hereinbelow, the disclosed method splits the 2-dimensional grid (1004) view of the 3-D catheter model (1001) at either a spline (1008) and/or sensor (1002) level in accordance with the disclosed embodiments, as further described hereinbelow, in order to capture the electrical activity sensed by the distal polar electrodes as delineated in area (1503). The method permits the demonstration of the rotational activity (1500) about this delineated area (1503) of FIG. 15B and translates these signals to approximately the center region of the grid view (1004). This method permits the proper translation of the electrical activity manifested by the rotor, thus permitting visualization of the continuous rotation about a specific region of the heart (120) including polar regions relative to the catheter model (1001).

FIG. 15B illustrates a top view of the catheter model (1001) showing an example rotor located near the distal tip with radially extended splines (1008). In the shown example, the rotor (1500) rotates about the distal tip (306). The progress of the activation activity is shown in a continuous rotational path from this viewpoint. This illustrates the activity ideally being located, so that the respective area of the organ or heart can be treated either via ablation or other treatment technique even if the rotational source is located remotely relative to the catheter's location in the heart (120).

Figure 16A:
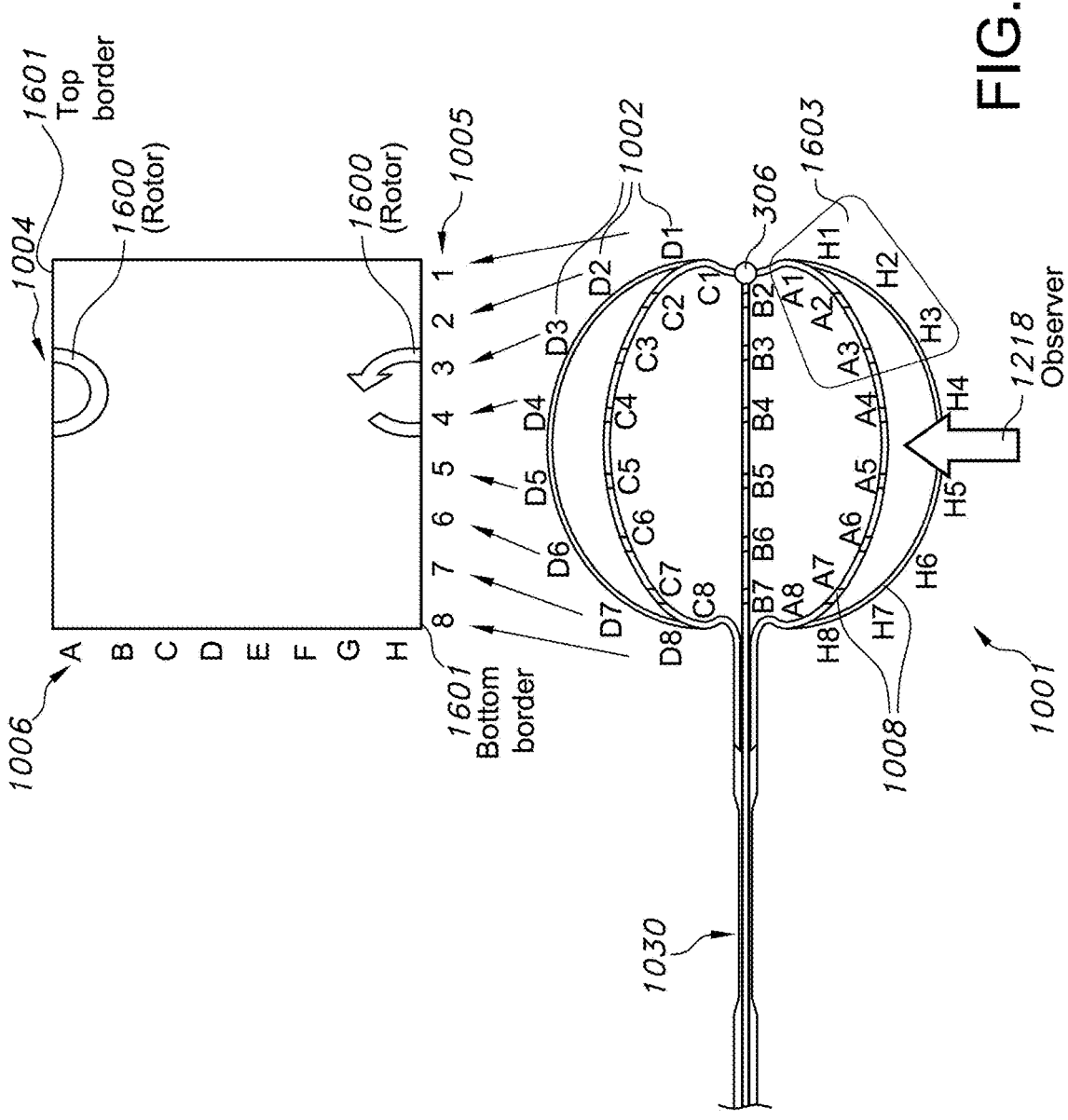
FIG. 16A illustrates an initial viewpoint of a rotor located at a distal pole with the rotor shown out of view on the translated 2-D grid.

FIG. 16A illustrates an initial viewpoint of a rotor located at a distal pole of the catheter with the rotor non-discernible, dispersed and not clearly or fully in view on the translated 2-D grid. The rotor (1600) translates on the 2-D grid (1004) as fragmented across the top and bottom borders (1601) of the grid (1004). This fragmented or random electrical activity of existing rotors on the translated 2-D grid may be associated with polar rotors or other edge conditions described in FIGS. 15A and 15B. Such remotely located rotors, activations, focal sources, wavefronts or other electrical activity generally manifest approximately at or near distal (306) portions of the catheter (1001) or relative areas of the heart that are considered more difficult for the catheter to sense, discern and process such activity or sources. As shown in the grid (1004), the rotor (1600) is fragmented at portions near splines A and H and respective sensors A3, A4, H4 and H3 designated in area (1603) of model (1001). This information regarding the locations of the random electrical activity is then used to make a determination as how to adjust the respective grid view (1004). At a minimum, it provides the user with an initial frame of reference as the observer's viewpoint (1218) is located and split between splines A and H on the catheter model (1001). The user can capture and join the fragmented portions of the rotor (1600) by adjusting the 3-D catheter model (1001) and center the full rotor such that it is translated onto the 2-D grid in full view, such methods are in accordance with algorithms as described in greater detail hereinbelow.

Figure 16B:
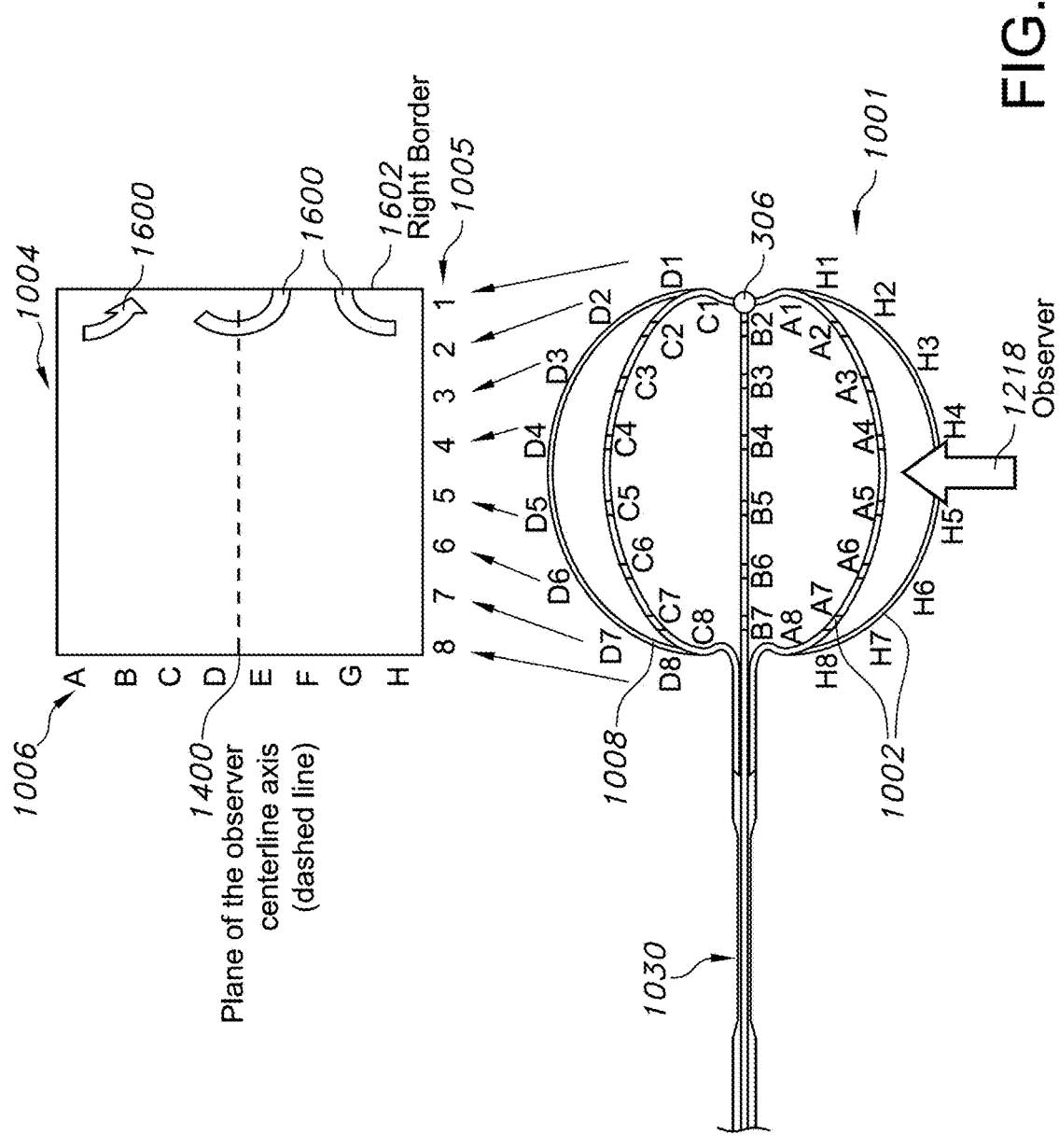
FIG. 16B illustrates an adjusted view of a rotor as split between splines A-H with the translated rotor out of view on the 2-D grid.

FIG. 16B illustrates an adjusted view of a rotor with a spline split implemented between splines A-H with the translated rotor fragmented and unidentifiable as translated on the 2-D grid (1004). This figure illustrates when edge conditions are present in a region of the heart relative to the catheter sub-assembly (301) and the translated source or rotor (1600) is not yet shifted into full view on the 2-D grid (1004). As shown, the plane of the observer (1218) as translated is located on the grid (1004) at centerline axis shown as a dotted line (1400) which lies between splines D and E. This illustrates that implementing a spline split between splines A and H (1002) on the 3-D model (1001), does not shift or bring the rotor into full view on the translated grid (1004). As shown on the grid (1004), the rotor is still visibly fragmented and/or dispersed along the right border (1602) of the grid (1004). When the rotational source or rotor lies at the distal point (306) of the catheter (301), there is generally required an additional offset adjustment of the signals to the 2-D grid (1004) in order to capture the complete rotational source onto the 2-D grid (1004). In this embodiment, splitting of the view at a sensor (1002) level is performed (in accordance with methods described hereinbelow) in addition to splitting the view at the spline (1008) in order to capture the full rotor in the translation of the various electrical signals sensed by the sensors onto the grid (1004).

Figure 16C:
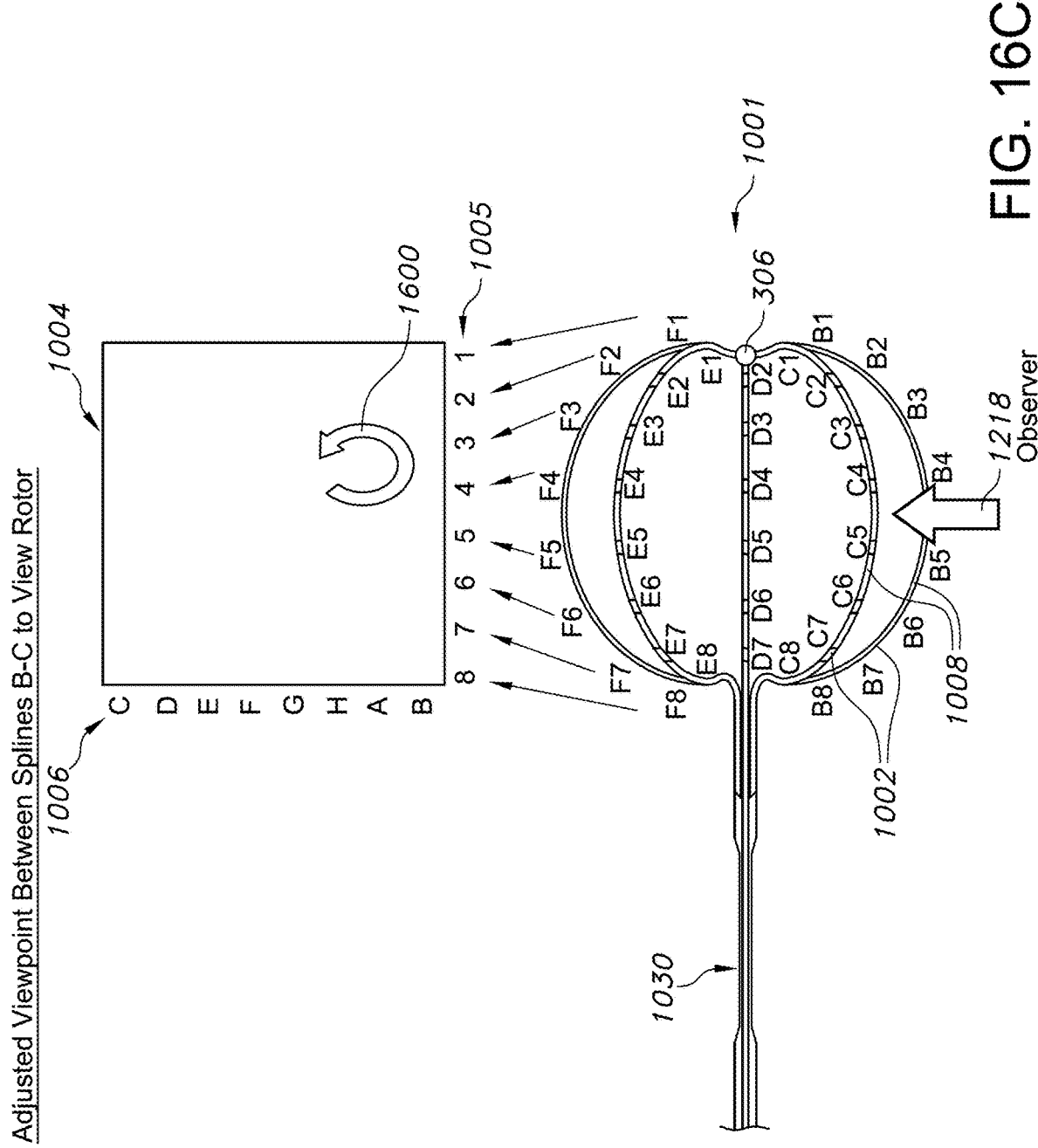
FIG. 16C illustrates an adjusted view of a rotor with a spline split implemented between splines so a continuous display of the rotor is discernible on the translated the 2-D grid.

FIG. 16C illustrates a further adjusted view of a rotor with a spline split implemented between splines so a continuous display of the rotor is discernible on the translated 2-D grid. The viewpoint on the 3-D catheter model (1001) is adjusted between splines B and C in the shown embodiment. The translated grid view (1004) indicates an entire or an approximate core area indicative of a rotor or rotational source discernible to the practitioner. In addition, the location of the continuous rotational source or rotor visible and identifiable over a discrete segment of time or multiple segments of time, can be used by the practitioner to target the area of the organ for potential ablation treatment or other treatment for lessening, treating, and/or ameliorating a cardiac rhythm disorder.

Figure 17A:
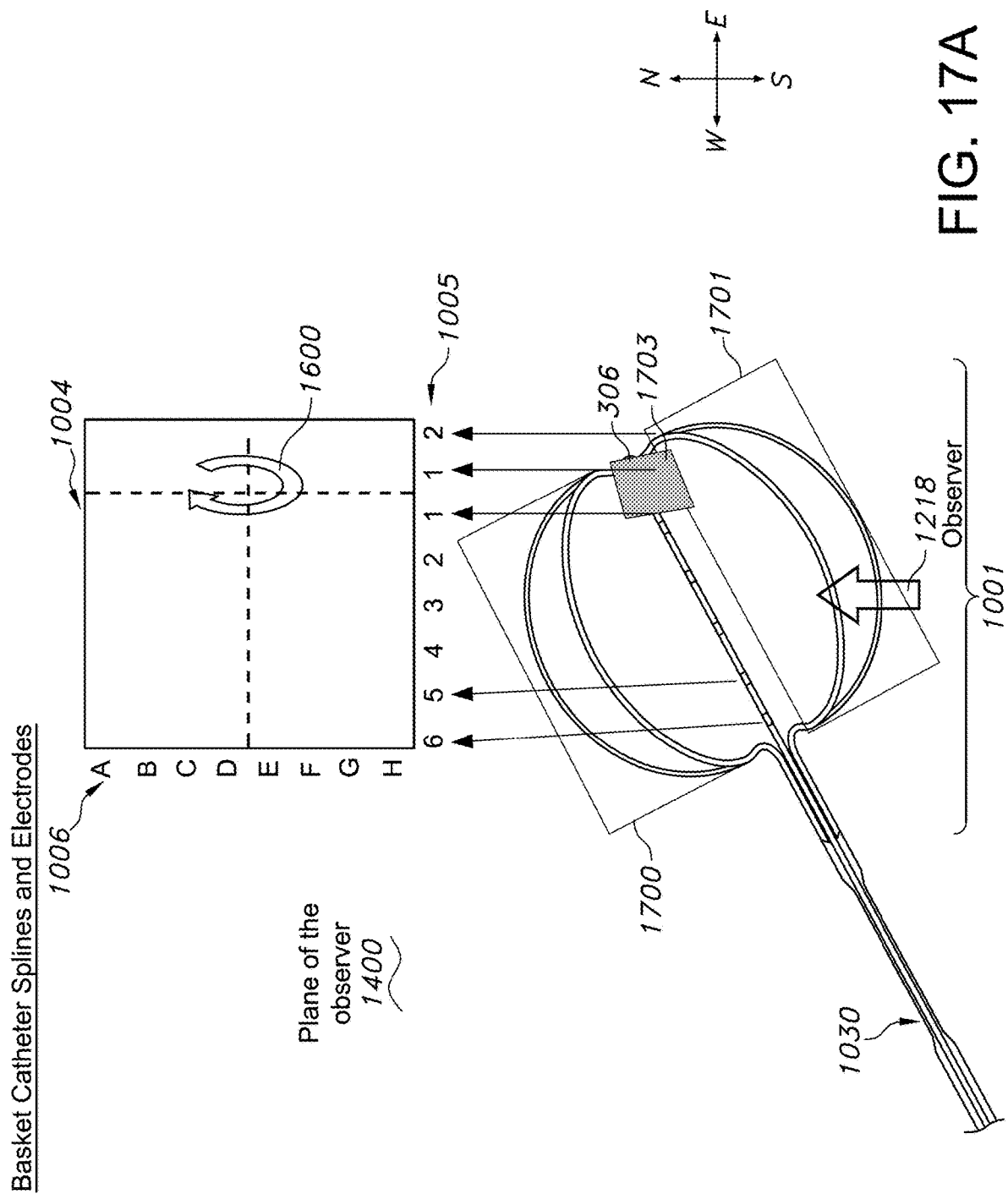
FIG. 17A illustrates an adjusted view of a 3-D catheter model with an angular tilt adjustment to the axis of the 3-D catheter shaft relative to its original axis.

FIG. 17A illustrates an adjusted view of a 3-D catheter model with an angular tilt adjustment applied by the system, computing device or processor, to the axis of the 3-D catheter shaft relative to its original axis. The catheter model (1001) shaft (1030) has been shifted downward at approximately a 45° angle relative to the plane of the observer axis line (1400) or horizontal x-axis. The catheter model (1001) has shifted approximately at a 45° angle in a northeast direction. An upward angular shift of the model (1001) is applied so that the distal point (306) is shifted in the northeast direction. The rotational source apparently is approximately located near the distal point of the catheter model (1001) relative to its original position. However, unable to bring the rotor into view by performing a split of the view at the spline (1008) level (such as for example, the scenario as described in FIG. 16B), an additional method is implemented to shift the complete circuit or near complete circuit of the rotor within the borders of the grid (1004) once the electrical signals are translated to the grid (1004). A split of the view at the sensor level is performed so that the grid (1004) representation only displays sensors 1 thru 6 of splines shown in area (1700) and sensor 1 thru 2 of splines shown in area (1701). The top hemisphere of the catheter model (1001) is translated onto the 2-D grid (1004) by performing a split at a spline-sensor reference located approximately in shaded area (1703) (the method described in greater detail hereinbelow), also located along a near spline and sensor approximately between areas (1700) and (1701). The practitioner is able to view at least one full rotational source (1600) or continuous rotational activity over at least one discrete time period that is indicative of a rotor or rotational source associated with a cardiac rhythm disorder as shown on grid (1004).

Figure 17B:
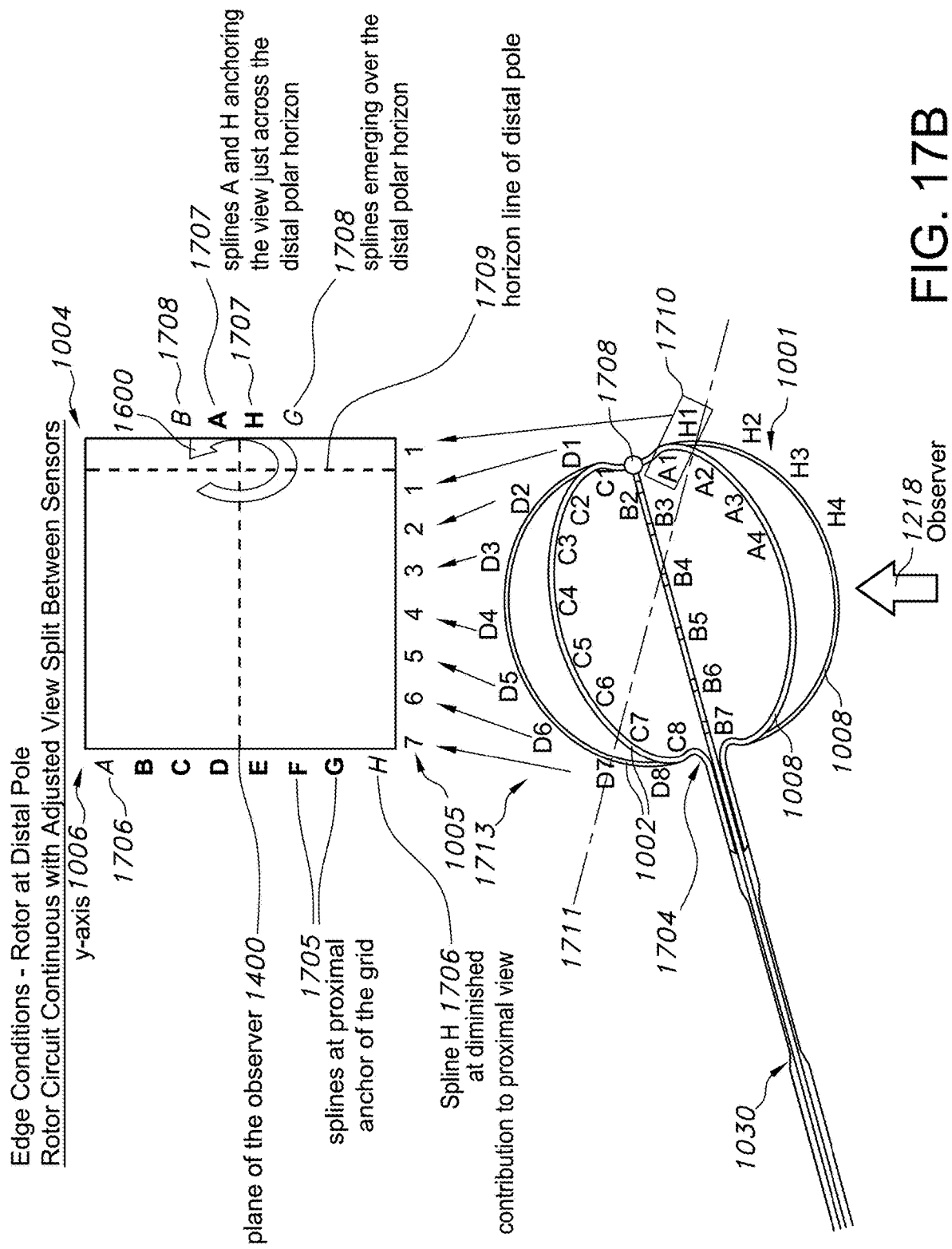
FIG. 17B illustrates an adjusted view of a 3-D catheter model with an angular tilt adjustment to catheter and a split performed between sensors at the distal hemisphere of the catheter.

FIG. 17B illustrates an adjusted view of a 3-D catheter model (1001) with an angular tilt adjustment applied by the system, processor and/or computing device, to the catheter model (1001) and a split performed between sensors located at the distal hemisphere (1708) of the catheter (1001) approximately in the distal polar region (1713) of the model (1001) approximately located above dotted line (1711). As shown in FIG. 17(b), the splines located at the proximal anchor of the grid (1705), are splines F & G. The relevance of splines A and H (1706) have a diminished contribution to the 2-D grid (1004). The adjustment to the catheter model (1001) and applied split at sensors and splines near the distal hemisphere (1708), has shifted the contribution of certain splines, namely A and H (approximately sensors 2-8) related to proximal anchor portions of the catheter model (1001). A and H have been shifted across the distal polar horizon (1707) on the grid (1004). The distal pole of the basket catheter (1708) has essentially been "flattened" so the observer is now "viewing" over the top of the distal hemisphere (1708) so the respective signals sensed by the spline-sensors in that region can be viewed comprehensively on the 2-D grid (1004) rather than in segmented fragments along the grid borders (as described in FIGS. 16A and 16B).

Therefore, in the shown example, splines B and G (1708) have emerged over the distal polar horizon (1709) once the view is split at the sensor-spline level. In the shown example, the split of the 3-D model (1001) occurs at splines A and H, at sensors A1 and H1, respectively. The observer's viewpoint (1218) is a guide point for the approximate determination of the spline-sensor split. It is also noted that Splines A and H particularly at sensors A1 and H1 (1710), anchor the view across the distal polar horizon (1707) as subsequently the 2-D translation of the signals at those respective sensors in its "flattened" view delineate the approximate location of the rotor on the grid (1004). The horizon line (1709) intersects the plane of the observer centerline axis (1400) at approximately the core or center region of the rotational source or rotor (1600). The full rotational source (1600) has not been shifted entirely into view on the grid (1004) but, the practitioner can now at least discern and identify that a rotational source or rotor emanates from or near the respective location of the organ since a significant portion of the rotor is now discernible. However, the rotor may also precess so the location may shift during the user's observation of the respective rotational activity during a discrete segment in time.

Figure 18:
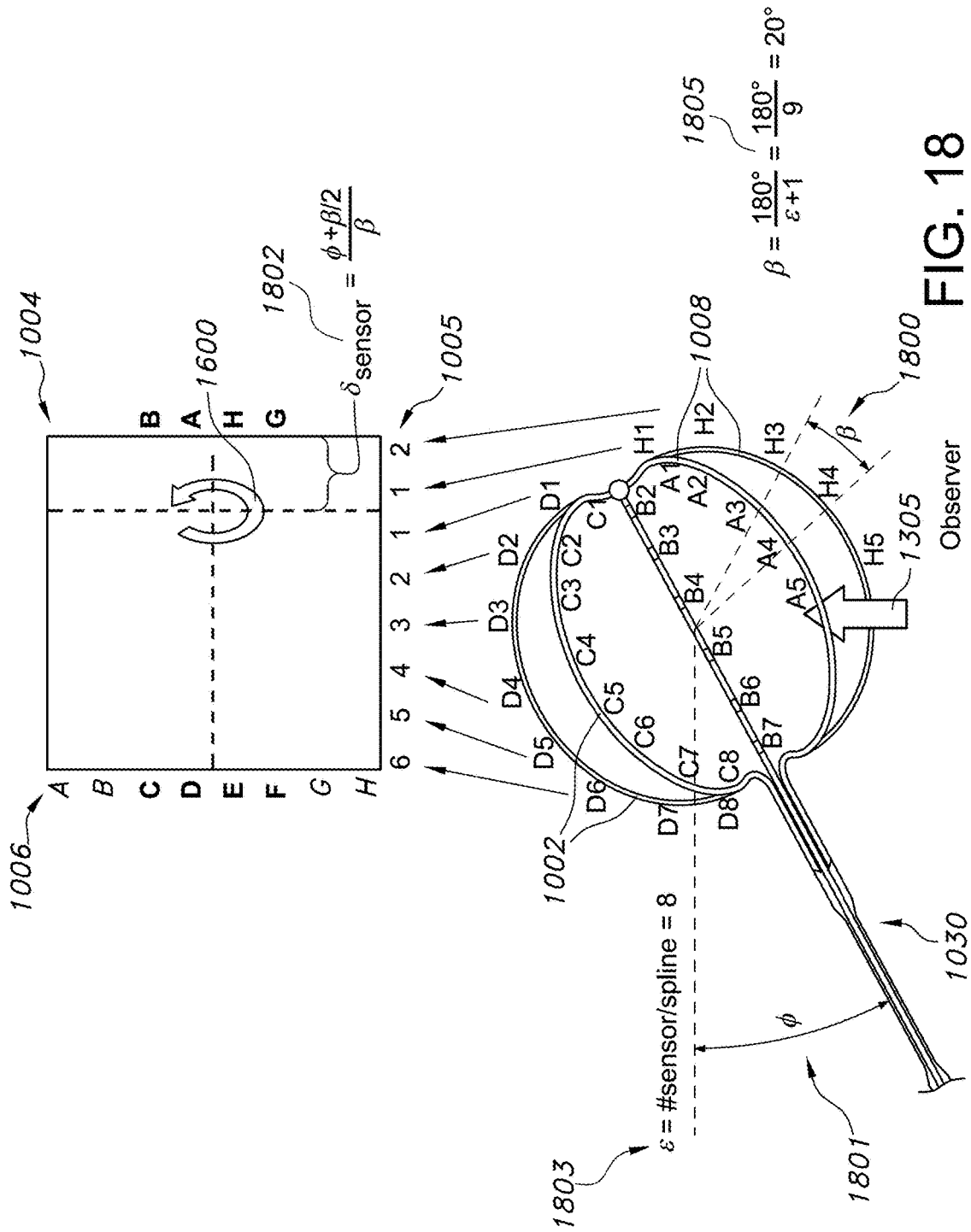
FIG. 18 illustrates an example method of calculating spline-sensor translations to grid resulting from an axis tilt of the 3-D catheter model.

FIG. 18 illustrates an example method of calculating spline-sensor translations to grid resulting from an axis tilt of the 3-D catheter model (1001) and further performing a split of the catheter model or representation. FIG. 18 further illustrates an example set of algorithms that are implemented in performing a split of the 3-D catheter model at a spline-sensor level relative to the observer's view (1305).

In the shown example, β=the angle between two splines (1800) which is generally a fixed value for a particular type of catheter being implemented. However, this value can also be variable in certain embodiments. If there are for example, 8 splines (1008) in the basket catheter sub-assembly (301) and 8 sensors, then ε=1, when applying the equation (1803) provided below, $$\beta = \frac{180°}{9} = 20°,$$

applying a value of ε, to the equation (1805) provided below.

$$\varepsilon = \frac{\text{\# sensors}}{\text{\# splines}} \quad (1803)$$

$$\beta = \frac{180°}{\varepsilon + 1} \quad (1805)$$

$\delta_{sensor}$ (1802) is a sensor-spline offset value, more particularly defined as the number of units (e.g. spline units) as adjusted on the sensor axis (1005) of the grid once an angular tilt of the 3-D catheter model (1001) is applied. This value is considered a discrete sensor spline offset value. Φ (1801) is defined as the tilt angle formed between the original orientation of the catheter shaft (1030) axis (generally the x-axis) and the shaft (1030) once the catheter (1001) and its shaft (1030) is tilted relative to any of the x-y-z plane.

As an example, if the tilt angle or roll angle, φ=45° (using 45° as the applied angle of tilt or rotation to the 3-D model), and applying the value of β (1805), wherein β=20% the spline-offset value would be considered to be a value of 2.75. In the shown embodiment, the spline-offset value can be rounded to the next whole integer, a unit value of 3 or $\delta_{sensor}$=3. The resultant sensor-spine offset value is considered the unit that each sensor is shifted as translated onto grid.

$$\delta_{sensor} = \left\lfloor \frac{\phi + \beta/2}{\beta} \right\rfloor \quad (1802)$$

Relative to FIG. 17B, the rotational source (1600) shown in FIG. 18, has since shifted two sensor-spline units to the left and is now discernible on the grid (1004) as a rotor or rotational source as continuous activity is evident for a particular time period. The adjusted view as split between the sensors (1002) reveals an entire rotor circuit region (1600). The observer (1304) can use this information to determine the approximate location of the source in the organ of the patient and possibly target the area of the organ for treatment using ablation or other available treatment methods.

Figure 19:
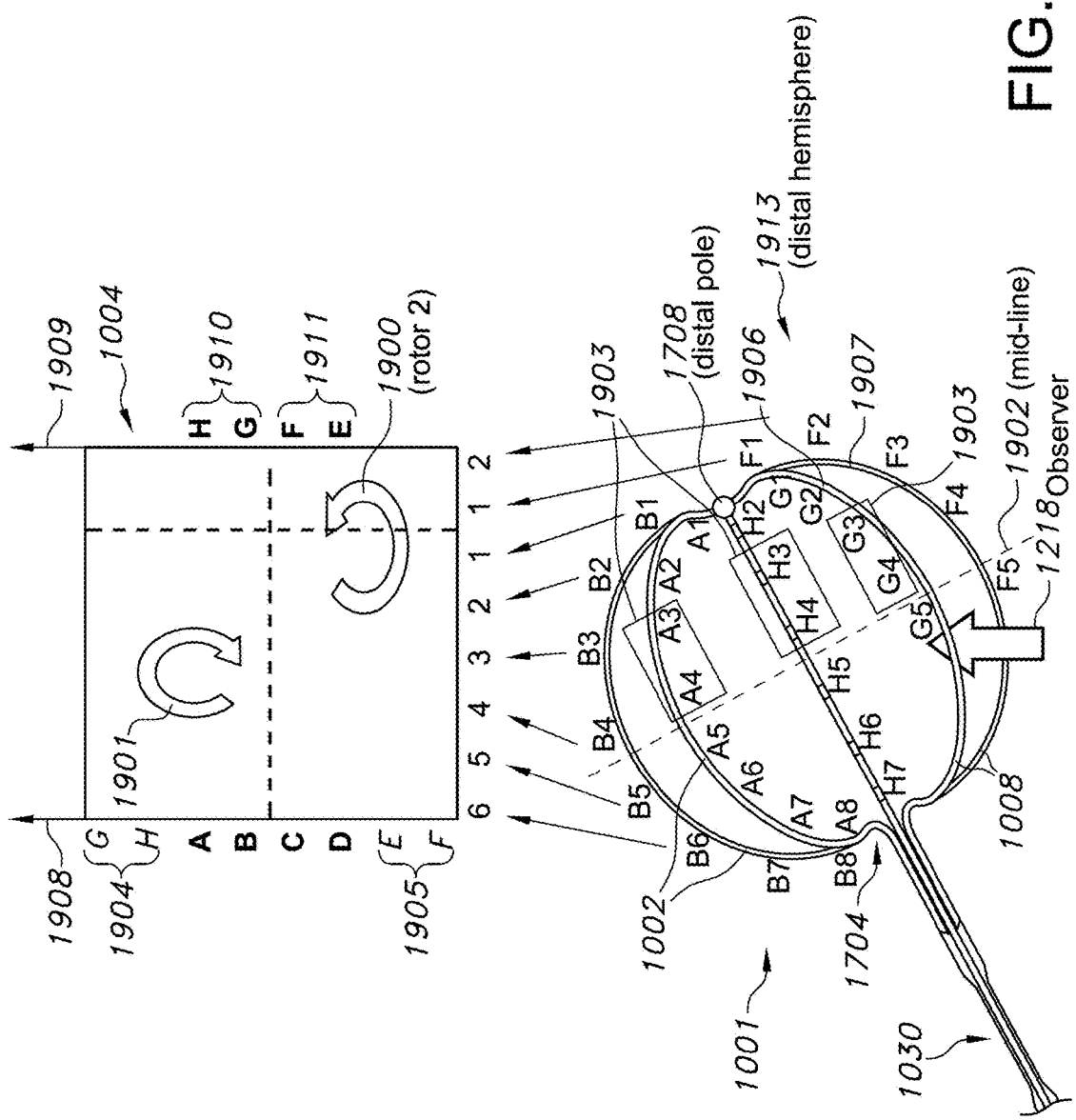
FIG. 19 illustrates an adjusted view of a 3-D catheter model with an angular tilt adjustment to catheter model and a split performed between sensors at the distal hemisphere of the catheter.

FIG. 19 illustrates an adjusted view of a 3-D catheter model with an angular tilt adjustment or roll angle applied to the catheter model with a split of the view performed between sensors at the distal hemisphere of the catheter. The adjusted grid view is offset at both spline and sensors for extended flexibility in viewing edge conditions located at both the distal pole (1708) and at least one other region of the heart (120). The model is adjusted at both the sensor and spline locations so that two rotors, rotor 1 (1901) and rotor 2 (1900) are visible on the grid (1004) and identifiable as rotational sources that are continuous for at least a discrete time period. The observed sources are associated with a cardiac rhythm disorder. The observer's initial viewpoint (1218) is split between splines G (1906) and F (1907).

Once the system performs a rotational tilt of the catheter model (1001) applying the algorithms as described in FIG. 18, the translated model shown in the grid (1004) centers the two rotors sufficiently so they are visible within the borders of the grid (1004) and sufficiently centered within the same borders of the grid. Rotor 1 (1901) is shifted into view by the split at the sensors performed approximately near the equator of the catheter model (1001), approximately sensors A4 to G4. The catheter model has been adjusted so that the shaft (301) is angled and pointing from out of the page as shown in FIG. 19 in 3-dimensional space relative to a certain angle. The area of rotor 2 (1900) is approximately located at or near sensors C1, F1, E1, D1 and D2 as shown in grid (1004). The practitioner may ablate the wall of the heart located near those same sensors on the catheter model (1001). The area of rotor 1 (1901) is approximately located at or near sensors A4, A3, H4, H3, G4, B3 and B4 as shown in grid (1004). The practitioner may ablate the wall of the heart located near those same sensors shown as at least corresponding to bounded areas (1903) on the catheter model (1001). There is generally at least 1 electrode unit in addition, which surrounds the shown areas of each visible rotor (1900) and (1901) where the practitioner may also ablate or treat the tissue of the heart.

FIG. 19 also illustrates that there may be more than one rotor or rotational source that is identifiable in the region of the heart located near the sensors indicating continuous activations or electrical activity on the grid (1004) for at least a discrete period of time. The view is adjusted such that each of the rotors or rotational sources are moved towards the center of the grid (1004) and shifted away from the borders of the grid (1004) but, sufficiently so that both rotors are identifiable and visible within the grid (1004). On average it is known that a patient suffering from cardiac rhythm disorders has at least two or even more rotors or rotational sources associated with the cardiac rhythm disorder.

In the shown example, the rotor 2 (1900) is located near the distal pole (1708) of the catheter and rotor 1 (1901) is located near the equator or along the mid-spline hemisphere line (1902) of the catheter model (3D) at or near sensors A4 to G4 which are spatially related to the patient's heart. It is also noted that as the rotational tilt of the catheter model (1001) is applied to the representation, the resulting splines G and H (1904) and splines E and F (1905) of the grid (1004) shift in view and resultantly, become less relevant to the left axis (1908) of the grid. Each of splines G and H (1904) and E and F (1905) have since shifted to the right side of the grid (1909) as shown in elements (1910) and (1911) of the grid (1004). This is relevant to the shift in the view of upper hemisphere of the model (1001) on the grid (1004) as the applied rotational tilt of the catheter model (1001) has permitted essentially, a "flattened" view of the top hemisphere (1913) of the catheter model (1001). This flattening occurs at and beyond the equator (1902) towards the distal pole (1708) of the catheter and translates the higher numbered sensors 4-8 towards the left portion of the grid (1004) closer to the left axis (1908) while translating the lower numbered sensors 1-2 and splines H to E towards the right portion of the grid (1004) closer to the right axis (1909). It is additionally noted that sensors 7 and 8 in the shown example, for each of the splines A-H, have been shifted entirely out of view on the translated grid (1004) and are no longer in view.

The system and method are described to have "flattened" the top hemisphere beyond the equator (1902) and focused the translation of corresponding activation signals to grid (1004) on the upper half of the hemisphere from the distal pole (1708) towards the center hemisphere line (1902). The disclosed method is similar to a zooming in feature with a focus on only a portion of the 3-D hemisphere model (1001) as flattened from the distal pole (1708) in order to shift into grid view the full rotational source(s) which otherwise were not readily discernible or identifiable. Other embodiments may zoom in on a portion of the catheter model with a flattening of the proximal hemisphere of the catheter model (1001) from the proximal pole (1708) towards the mid-spline line (1902) of the catheter (1001). In other embodiments, there is yet a focus on any other areas of the catheter model (1001). The application of the disclosed method on a particular region of the heart (and catheter model) depends on what is considered a relevant area for treatment of a cardiac rhythm disorder. The practitioner may also identify multiple activations, including activations of focal source(s), or other sources that inter-relate and interact with each other. The translated view of the activation signals and/or source(s) in such cases would need to be tailored or shifted in order for the cardiac activation signals, focal source(s) or multiple rotational sources to be identifiable as shifted on the grid view.

FIG. 20A illustrates an adjusted view of a 3-D catheter model with a split performed between sensors in order to center the rotor's circuit region with the grid. The split is performed between sensors from the mid-line (1902) to the distal pole (1708) of the catheter. In the disclosed embodiment, the grid view (1004) is further adjusted by applying a rotational shift to the catheter shaft (1030) with the distal pole (1708) moved away from the observer's view along the z-axis. The catheter shaft (1030) is essentially rotated more in alignment with the distal pole but, approximately at a 30° angle relative to the y-axis. This may be accomplished by a rotational tilt of the catheter model (1001) such that its shaft (1030) now extends in a southward direction relative to the distal pole (1708) axis or y-axis. The adjustment is applied to the 3-D catheter model (1001) in order to shift the rotor (1600) as translated on the grid (1004) into an approximately centered position or at least within the shown area of the grid (1004). The rotor in this figure is located near the distal pole (1708) region of the catheter (1001) which required a flattening of the 3-D model from its distal point (1708) towards its equator or mid-line (1902), the distal hemisphere (1913).

Splines A and B (1904) and Splines G and H (1905) have been shifted to the opposite edge (1909) of the grid as a result of the flattening and focus on the distal hemisphere (1913) of the catheter model (1001). The applied rotational tilt of the catheter model (1001) has essentially "flattened" and focused the view on the activations emanating from the top hemisphere (1913) of the catheter (1001). This flattening occurs at and beyond the equator (1902) towards the distal pole (1708) and translates the lower numbered sensors 1 to 5, west of line (1914) and sensors 1 to 3, east of line (1914). Meanwhile, splines B, A, H and G, respectively are translated, as shifted towards the right edge (1909) of the grid (1004) at locations (1910) and (1911), respectively. It is additionally noted, that sensors 6 to 8 for each of the splines A-H have been shifted entirely out of view on the translated grid (1004) and thus, are no longer in view. The source (1600) is identifiable as a continuous rotational source (or a rotor) at least for a discrete time period as translated and identifiable within the borders of the grid (1004).

Figure 20B:
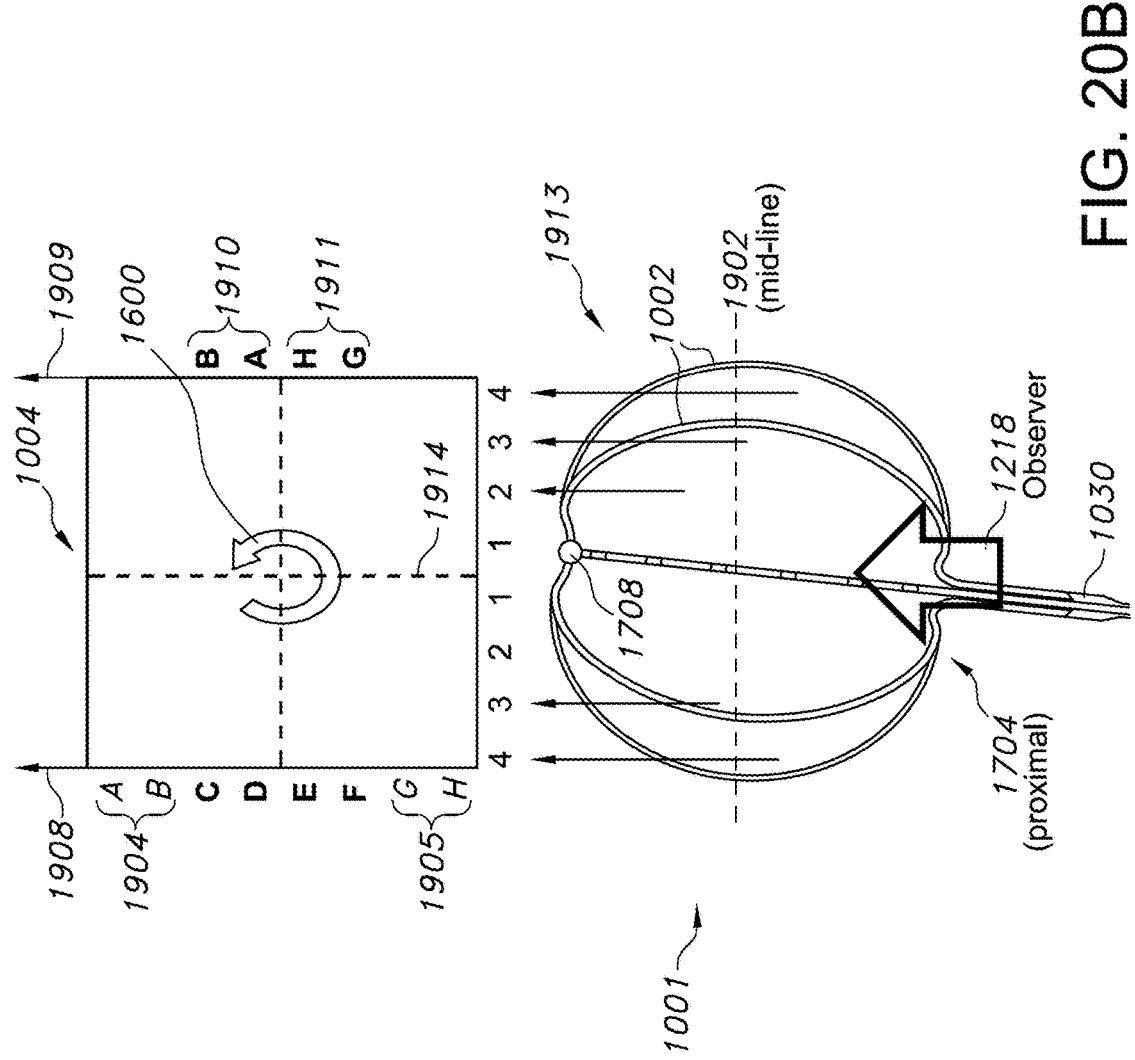
FIG. 20B illustrates an adjusted view of the 3-D catheter model of FIG. 20(a) with catheter model being aligned to distal polar axis and a split performed between sensors from the mid-line to the distal pole of the catheter.

FIG. 20B illustrates an adjusted view of the 3-D catheter model of FIG. 20A with catheter model now aligned to distal polar axis and a split performed between the sensors (1002) from the mid-line (1902) to the distal pole (1708) of the catheter. The grid view (1004) is adjusted by aligning the catheter shaft (1030) with the distal pole (1708) of the catheter model (1001). This may be accomplished by a rotational tilt of the catheter model (1001) such that its shaft (1030) now extends in a southward direction relative to the distal pole (1708). This adjustment is applied to the 3-D catheter model in order to shift the rotor (1600) into an approximately centered position on the grid (1004). The rotor in this figure was centered at the distal pole region of the catheter (1001) which required a flattening of the 3-D model from its distal region (1708) towards its equator or mid-line (1902).

Splines A and B (1904) and Splines G and H (1905) have since been shifted to the opposite edge (1909) of the grid as a result of the flattening and focus on the distal hemisphere (1913) of the catheter model (1001). As described in FIG. 19B, the applied rotational tilt of the catheter model (1001) has essentially "flattened" and focused the view on the activations emanating from the top hemisphere (1913) of the catheter (1001). This flattening occurs at and beyond the equator (1902) towards the distal pole (1708) and translates the lower numbered sensors 1 to 4 so they are symmetrically in view starting from line (1914) on the grid (1004). Meanwhile, splines B, A, H and G, respectively are translated towards the right edge (1909) of the grid (1004). It is additionally noted that sensors 5 to 8 for each of the splines A-H have been shifted entirely out of view on the translated grid (1004) and are no longer in view. The source (1600) is identifiable as a continuous rotational source (or a rotor) at least for a discrete time period as shown centered on the grid (1004).

Figure 21A:
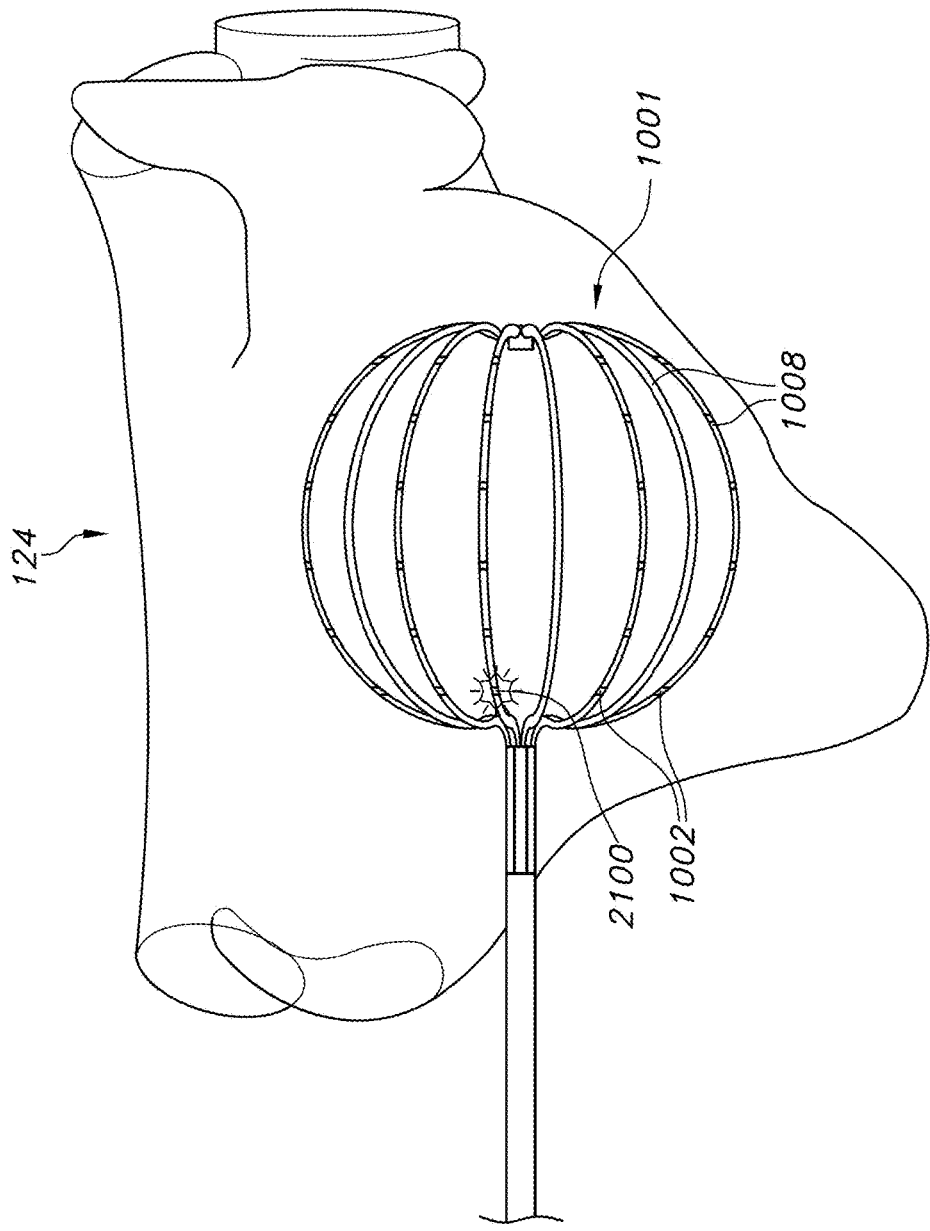
FIG. 21A illustrates a target electrode selected by the user as a starting point for adjustment of the 3-D catheter model.

FIG. 21A illustrates a target electrode selected by the user as a starting point for adjustment of the 3-D catheter model (1001), once the catheter subassembly 301 is delivered in the left atrium (124) of the patient's heart (120) in accordance with the disclosed methods. The practitioner selects a target electrode visible as a lit-up sensor (2100), and may select additional sensors (1002) as points of reference to adjust the model at a spline(s) (1008) and/or sensor(s) (1002) level. Generally, the practitioner has noted more significant activity, e.g., activations or other activity associated with source (s) at least near the selected electrode (2100), and selects the sensor (2100) as a starting point to further observe a region of the catheter model (1001) located near the electrode (2100). In other embodiments, the practitioner may also use the sensor (2100) as a starting point for adjustment of the model (1001) in accordance with already described methods hereinabove. Additional embodiments using this feature are disclosed in greater detail hereinbelow.

Figure 21B:
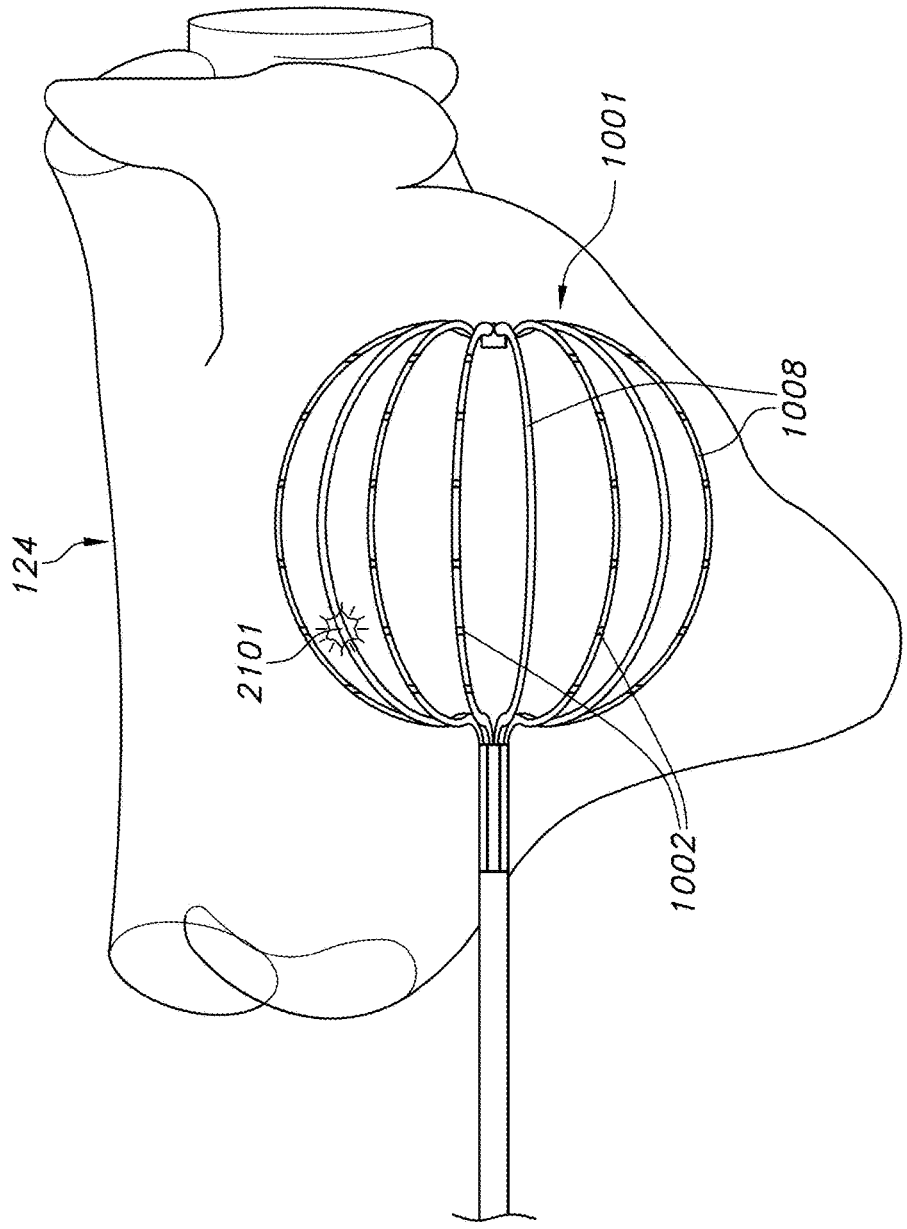
FIG. 21B illustrates a target electrode selected by the user as an alternate starting point for adjustment of the 3-D catheter model.

FIG. 21B illustrates a target electrode selected by the user as an alternate starting point for adjustment of the 3-D catheter model (1001) once the basket subassembly 301 is delivered in the left atrium (124) of the patient's heart (120) in accordance with the disclosed methods. The user selects a target electrode visible as a lit-up sensor (2101), and may select additional sensors (1002) to adjust the 3-D model (1001) at a spline and/or sensor level in order to identify a rotational source on the translated grid view (1004). Generally, the practitioner can determine more significant activity, e.g. activations or other activity associated with source (s) at least near the selected electrode (2101), using the catheter model (1001) and selects the sensor (2101) as a starting point to further observe a region of the catheter model (1001) located near the electrode (2101). In other embodiments, the user may use the sensor (2101) as a starting point for adjustment of the model (1001) in accordance with already described methods hereinabove. Additional embodiments using this feature are disclosed in greater detail hereinbelow.

Figure 21C:
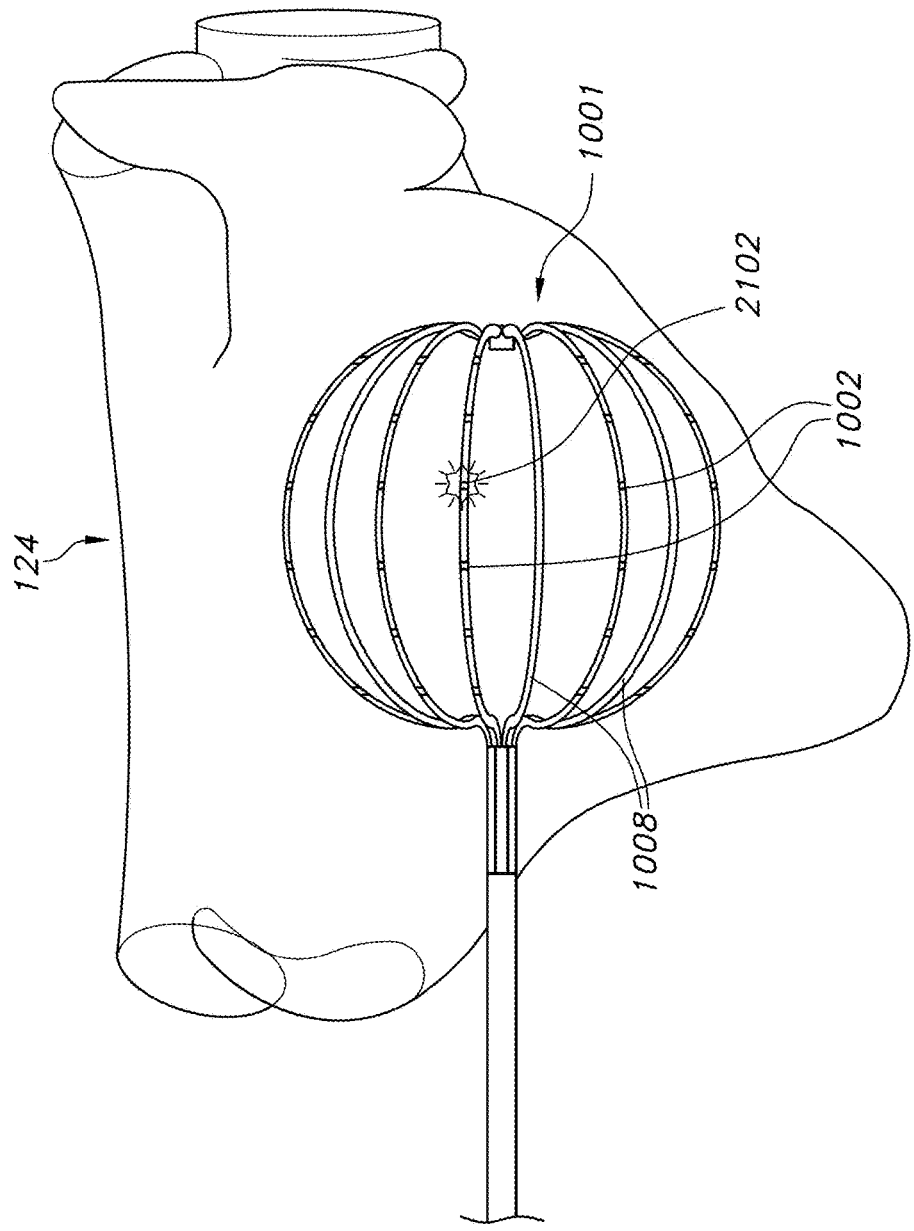
FIG. 21C illustrates a target electrode selected by the user as an alternate starting point for adjustment of the 3-D catheter model.

FIG. 21C illustrates a target electrode selected as an alternate starting point for adjustment of the 3-D catheter model (1001) delivered in the left atrium (124) of the patient's heart (120) in accordance with the disclosed methods. A target electrode visible as a lit-up sensor (2102), is selected by the system and additional sensors (1002) can also be selected to adjust the catheter model (1001) at a spline and/or sensor level in order to identify a rotational source on the translated grid view (1004). Generally, there is noted more significant activity, e.g. activations or any other identifiable activity associated with source(s) at least near the selected electrode (2102), and the sensor (2102) is selected as a starting point to further observe a region of the catheter model (1001) located near the electrode (2102). In other embodiments, the practitioner may also use the sensor (2102) as a starting point for adjustment of the model (1001) in accordance with already described methods hereinabove. Additional embodiments using this feature are disclosed in greater detail hereinbelow.

Figure 22A:
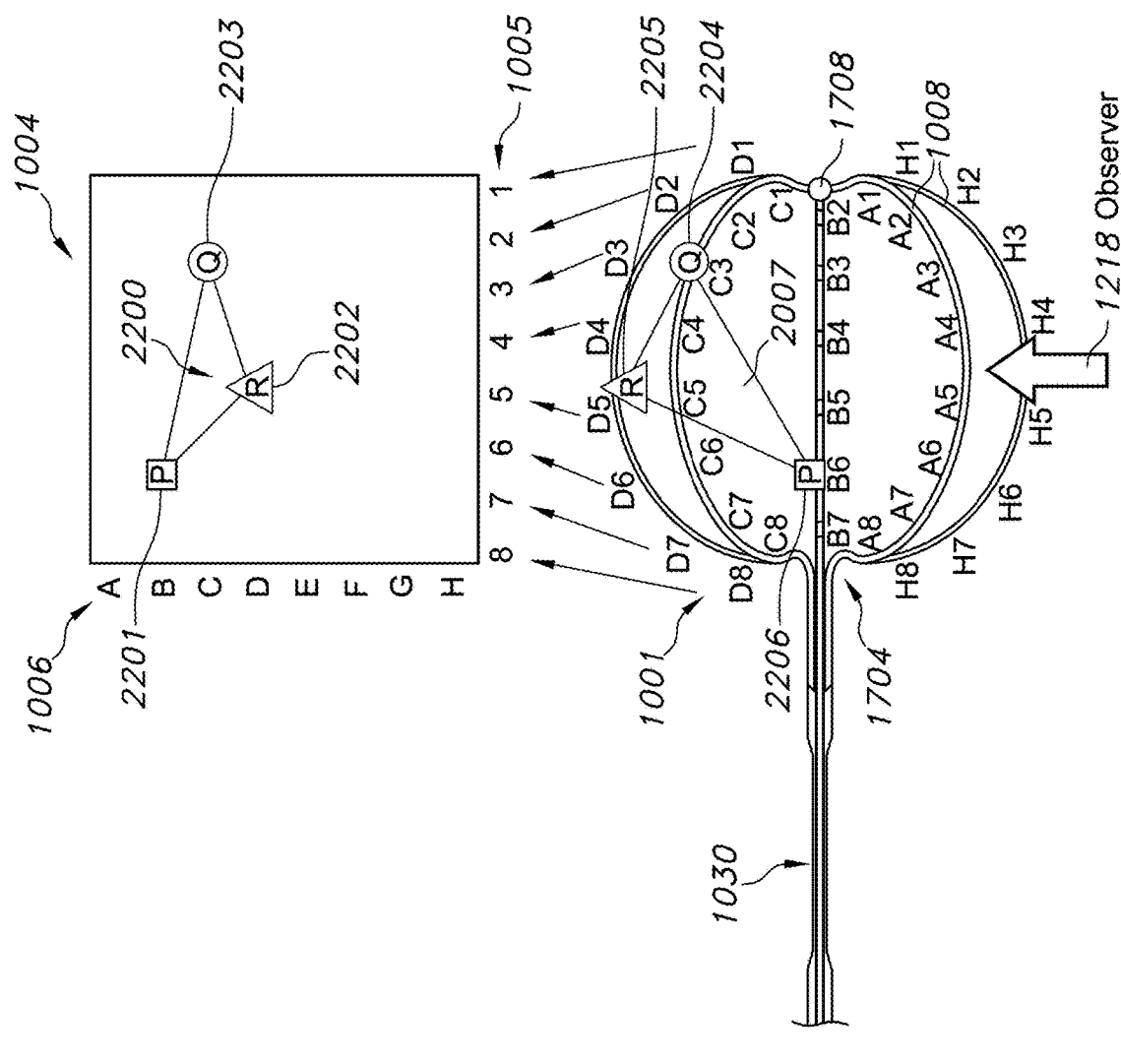
FIG. 22A illustrates a 3-D catheter model with three co-located vertices as selected and translated on the grid.

FIG. 22A illustrates a 3-D catheter model with three co-located vertices as selected and translated on the grid. The three vertices, namely P (2206), Q (2204) and R (2205) are selected as an area indicating repeated activations and/or some continuous activity or propagation such as a rotational source or focal source. The selection of the area can also be the result of an arbitrary selection of an area of the patient's heart (120) bounded by at least three sensor locations as represented on the translated grid by positional vertices P (2201), Q (2203) and R (2202). The area (2200) bounded by the three positional vertices may indicate for example, repeated activations, other repeated activity, a rotational source, focal source, centrifugal propagation, a rotor, or any other identifiable activity associated with a source(s), (whether focal source, rotational source, driver of a source, approximate core region, inner core of a source and/or other activity indicative of a source), once the cardiac information signals detected by the sensors in the 3-D model (1001) are translated to the grid (1004). The three positional vertices, R (2205), Q (2204) and P (2206) are located approximately near sensors D5, C3 and B6 on the 3-D catheter model (1001). As translated to grid (1004), the cardiac information signals detected by sensors at vertices R (2205), Q (2204) and P (2206), correspond to the same sensor locations shown on the grid (1004) at D5 (2202), C3 (2203) and B6 (2201). It is noted that the vertices or bounded area (2007) of the 3-D model (1001) may be selected as indicated, for example, by illuminated electrodes described in FIGS. 21A-21C.

Figure 22B:
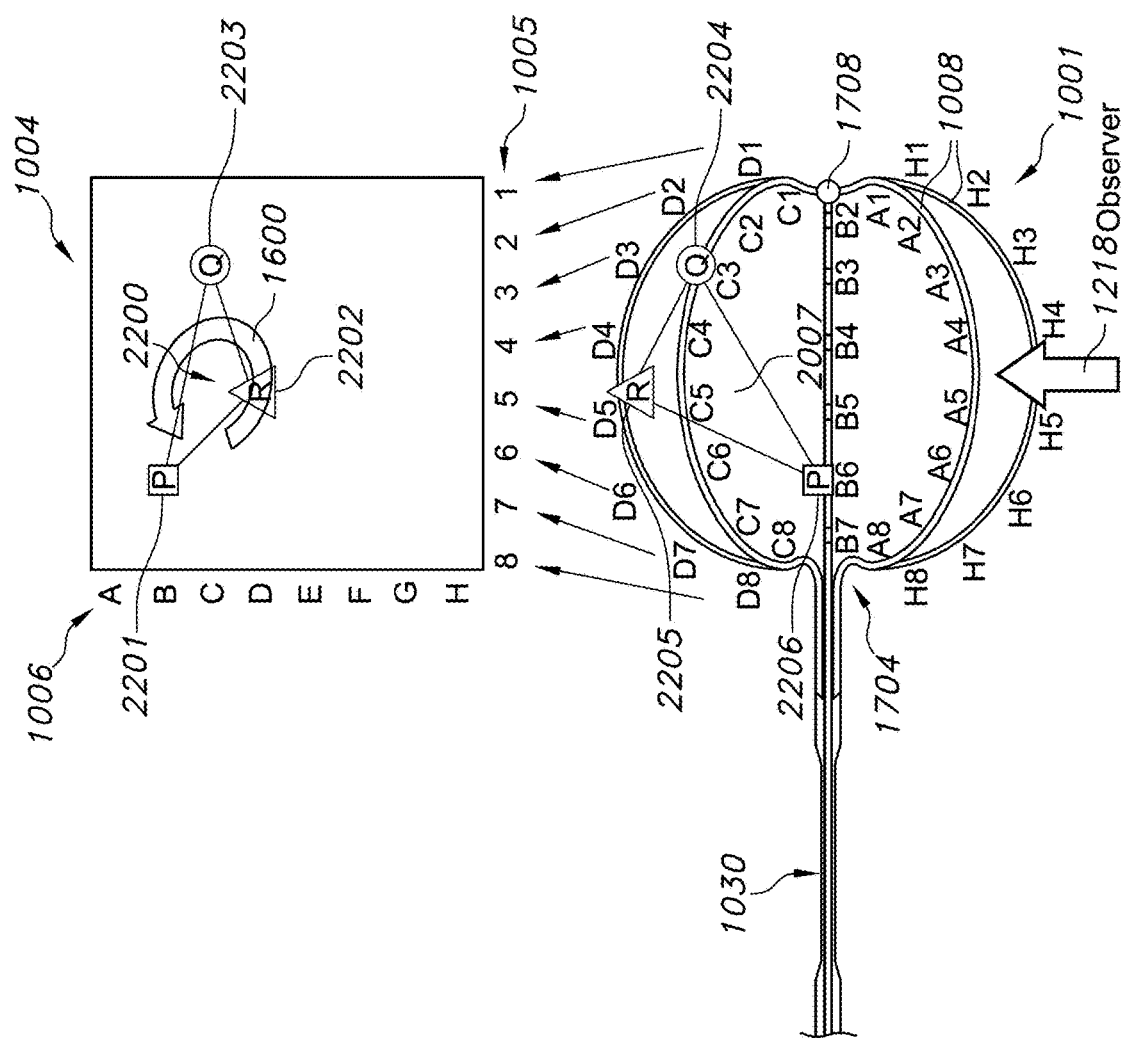
FIG. 22B illustrates a 3-D catheter model with three selected co-located vertices translated on the grid and bounding a rotational source.

FIG. 22B illustrates a 3-D catheter model with three selected co-located vertices translated on the grid and shown bounding a rotational source (1600). The three vertices, namely P (2206), Q (2204) and R (2205) selected as an area indicating repeated activations, centrifugal propagation, and/or some continuous activity such as a rotational source or focal source or otherwise any other identifiable activity associated with source(s) or driver. The selection of the area can also be the result of an arbitrary selection of an area of the patient's heart (120) bounded by at least three sensor locations as represented on the translated grid by positional vertices P (2201), Q (2203) and R (2202). The area (2200) bounded by the three positional vertices may indicate repeated activations, other repeated activity, a rotational source or a rotor once the cardiac information signals detected by the sensors in the 3-D model (1001) are translated to the grid (1004). The three positional vertices, R (2205), Q (2204) and P (2206) are located approximately near sensors D5, C3 and B6 on the 3-D catheter model. As translated, the cardiac information signals detected by sensors at the shown vertices R (2205), Q (2204) and P (2206), correspond to the same sensor locations shown on the grid (1004) at D5 (2202), C3 (2203) and B6 (2201). It is also noted that the vertices or bounded area (2007) of the 3-D model (1001) may be selected as indicated by illuminated electrodes described in FIGS. 21(a)-21(c).

Figure 22C:
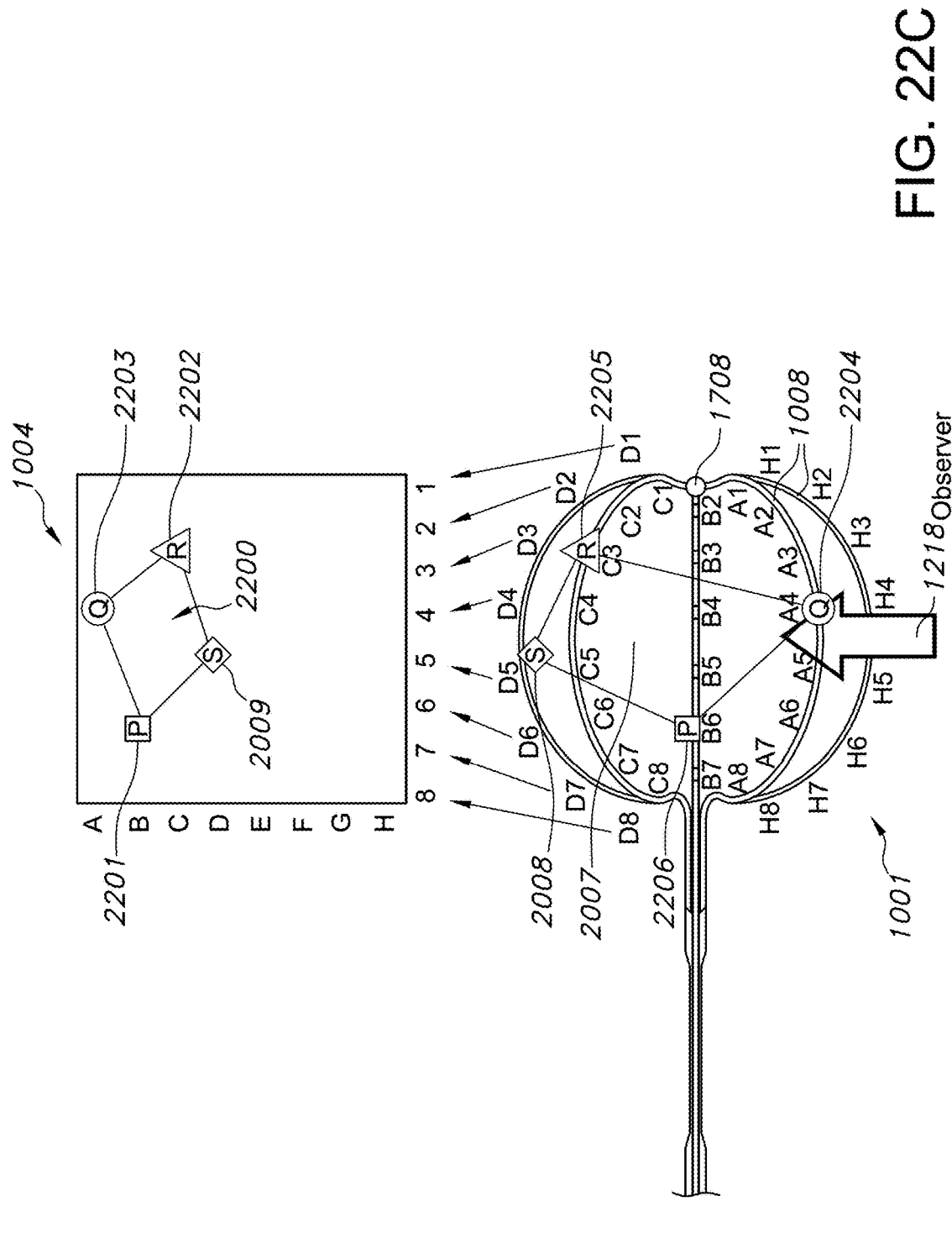
FIG. 22C illustrates a 3-D catheter model with n positional vertices bounding an arbitrary area as translated to grid.

FIG. 22C illustrates a 3-D catheter model with n positional vertices determined by the system and thereby bounding an arbitrary area, as translated to grid. In the shown example, the four positional vertices, namely P (2206), Q (2204), R (2205) and S (2009), are selected as an arbitrary area (2007) indicating repeated activations, focal source, centrifugal propagation and/or some continuous activity such as a rotational source. The selection of the arbitrary area (2007) can also be the result of an arbitrary selection of an area of the patient's heart (120) bounded by at least four sensor locations as represented on the translated grid by positional vertices P (2201), Q (2203), R (2202) and S (2008). The arbitrary area (2200) bounded by the three positional vertices may indicate repeated activations, other repeated activity, a rotational source, focal source or a rotor once the cardiac information signals detected by the sensors in the 3-D model (1001) are translated to the grid (1004). The selected positional vertices, R (2205), Q (2204), P (2206) and S (2008) are located approximately near sensors C3, A4, B6 and D5, on the 3-D catheter model (1001). As translated, the cardiac information signals detected by sensors at the shown vertices P (2201), Q (2203), R (2202) and S (2008), correspond to the same sensor locations shown on the grid (1004) at D5 (2009), C3 (2202), B6 (2201) and A4 (2203). The vertices or bounded area (2007) of the 3-D model (1001) may be selected as indicated by illuminated electrodes as described in FIGS. 21(a)-21(c).

Figure 22D:
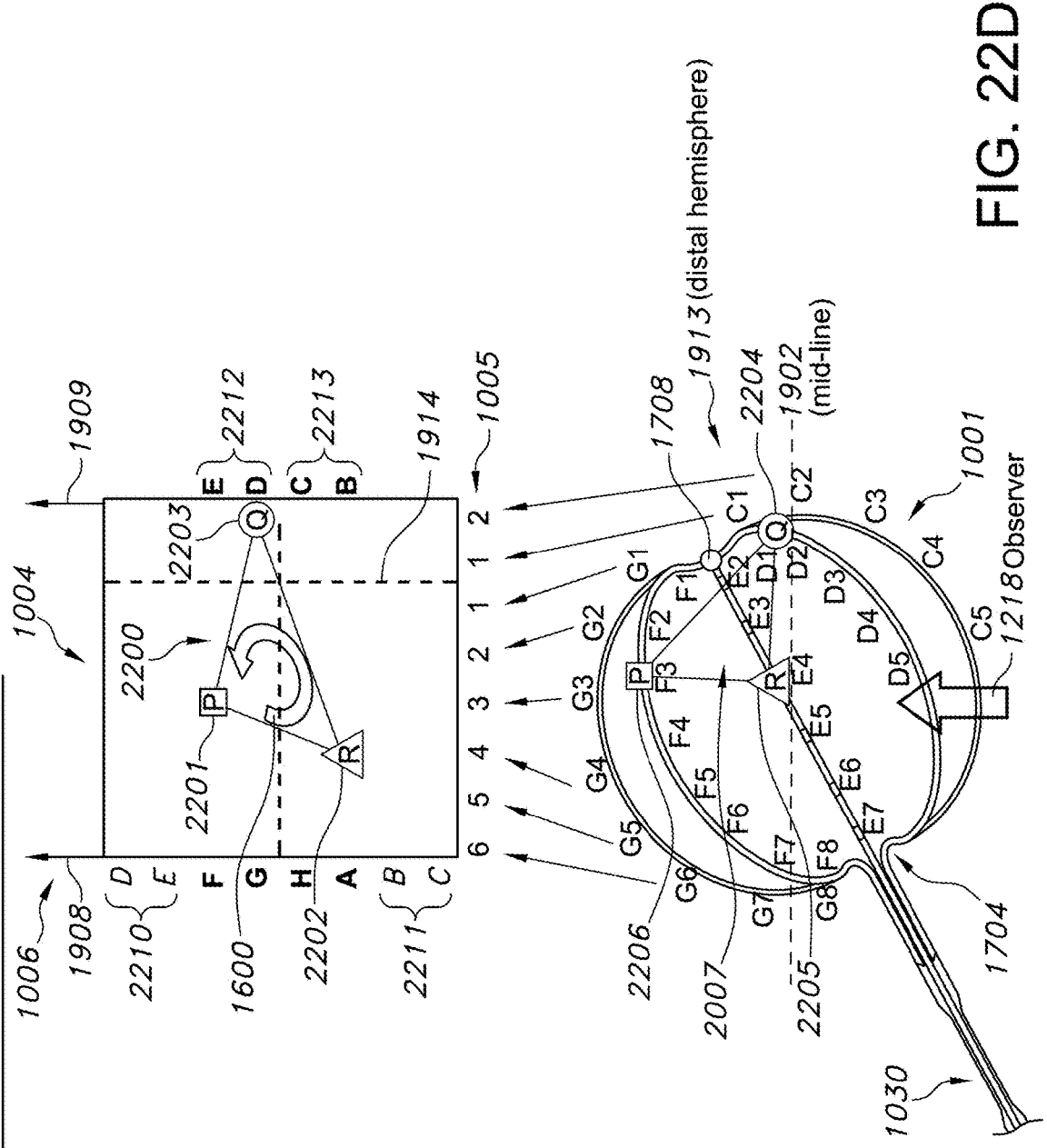
FIG. 22D illustrates a 3-D catheter model with three co-located vertices as selected and translated on the grid with applied spline-sensor adjustments.

FIG. 22D illustrates a 3-D catheter model (1001) with three co-located vertices as selected and translated on the grid with applied spline-sensor adjustments. The three vertices, namely P (2206), Q (2204) and R (2205) are selected as an area indicating repeated activations, centrifugal propagation and/or some continuous activity such as a rotational source or focal source including drivers and/or inner core region(s) of driving source(s). The selection of the area can also be the result of an arbitrary selection of an area of the patient's heart (120) bounded by at least three sensor locations as represented on the translated grid by positional vertices P (2201), Q (2203) and R (2202). The area (2207) bounded by the three positional vertices may indicate repeated activations, other repeated activity, a rotational source, focal source, or a rotor, once the cardiac information signals detected by the sensors in the 3-D model (1001) are translated to the grid (1004). The three positional vertices, R (2205), Q (2204) and P (2206) are located approximately near sensors E4, D2 and F3 on the 3-D catheter model (1001).

The observer (1218) in the shown embodiment has applied a rotational tilt or roll angle to the catheter (1001) model in accordance with the method described in FIG. 18. Spline-sensor offset adjustments are applied to the translated grid (1004) in order to view a continuous rotational source, centrifugal or repeated activations as bounded by the positional vertices P (2201), Q (2203) and R (2202) but, shifting the bounded area (2200) with the borders of the grid (1004).

As translated, the cardiac information signals detected by sensors at vertices R (2205), Q (2204) and P (2206), correspond to the same sensor locations shown on the grid (1004) at A4 (2202), D2 (2203) and F3 (2201). In addition, as described in FIG. 20A, Splines D and E (2210) and Splines B and C (2211) have since been shifted to the opposite edge (1909) of the grid as a result of the flattening and focus on the distal hemisphere (1913) of the catheter model (1001). The applied rotational tilt of the catheter model (1001) has essentially "flattened" and focused the view on the activations emanating from the top hemisphere (1913) of the catheter (1001). This flattening occurs at and beyond the mid-line equator (1902) towards the distal pole (1708) and depending on the applied angle of tilt, in this case translates the lowered lower numbered sensors 1 to 2, west of line (1914) and sensors 1 to 6, east of line (1914). Meanwhile, splines E, D, C, and B, respectively are translated as shifted towards the right edge (1909) of the grid (1004) at locations (2212) and (2213), respectively. It is additionally noted, that sensors 7 and 8 for each of the splines A-H, have been shifted entirely out of view on the translated grid (1004), and thus, are no longer in view. The source (1600) is identifiable as a continuous rotational source (or a rotor) at least for a discrete time period as translated and identifiable within the borders of the grid (1004) and bounded by vertices P (2201), Q (2203) and R (2202). It is also noted that the vertices or bounded area (2007) of the 3-D model (1001) may be selected as indicated by illuminated electrodes described in FIGS. 21A-21C.

As described in FIGS. 22A-D, the vertices or bounded area (2007) of the 3-D model (1001) may be selected as indicated by illuminated electrodes described in FIGS. 21A-21C. Additionally, it is noted that in certain embodiments implementing the methods described in FIGS. 22A-D, the positional vertices representing the three or more sensor locations can be selected on the user's computer screen (or display) either by manual entry of spline and/or sensor data or using a mouse or similar device that performs a "click and drag" of the selected vertices on the catheter model (1001). Using a mouse or similar device, the user may select the bounded area (2007) and drag the location so that a rotational tilt or roll angle is applied to the 3-D catheter model (1001). The signals are translated in accordance with the method described in FIG. 13 for spline adjustments and FIG. 18 for sensor adjustments. The user then determines based on the translation of the bounded signals to grid (1004) whether some repetitive electrical activity, a continuous rotational source, or a rotor, is identifiable. The user may then perform one or more adjustments to the catheter model (1001) until a continuous source, repeated activations (including centrifugal) and/or any other identifiable activity or activations associated with a source, as translated on the 2-D grid (1004) is identified. The user may also enter a value of a spline (1008) and/or sensor (1002) in which to apply a rotational shift and/or roll angle. Then a spline-offset and/or sensor-offset can be applied to each of the translated signals of each relevant spline and/or sensors, as selected on the catheter model (1001).

Figure 23:
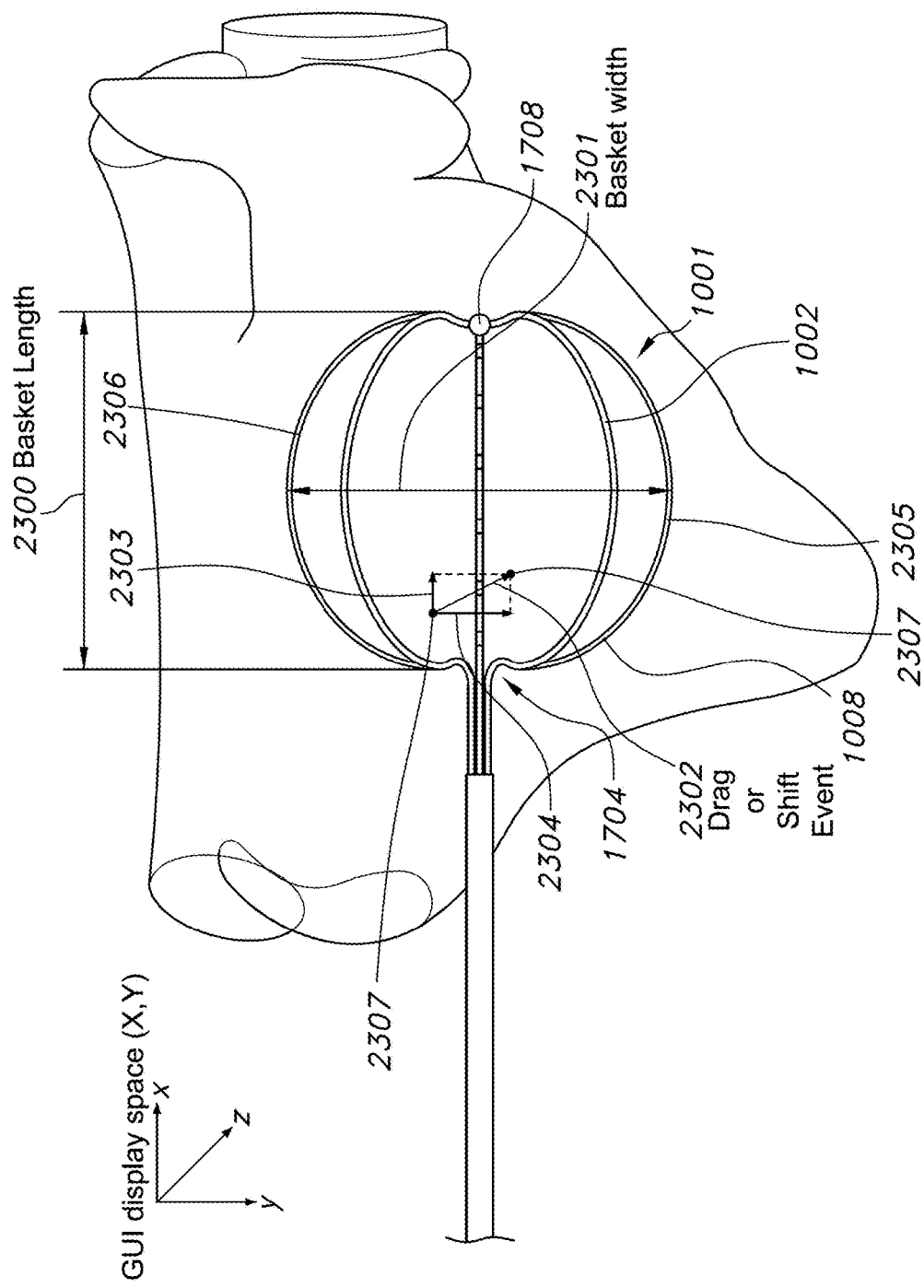
FIG. 23 illustrates mouse drag or shift events implemented to realize spline-offset events and/or spline-offset events on the translated grid.

FIG. 23 illustrates mouse drag or shift events, implemented to realize spline-offset events and/or spline-offset events on the translated grid. The user may implement a mouse drag event by selection of a random or a specific sensor (1002) on the catheter model (1001). The user may shift the catheter model (1001) in the x-direction in space, a unit distance of dx (2303) and/or may shift the catheter model (1001) at a particular sensor and/or random location on the catheter (1001), a unit distance of dy (2304). In the shown figure, the catheter model (1001) is shifted the distance dx (2303) in the x-direction starting at point (2307). The catheter model (1001) is further shifted, a unit dy (2304) in the y-direction, starting from point (2307). The basket width (2301) linearly extends from bottommost point (2305) to topmost point (2306) of the model (1001). The basket length (2300) linearly extends between the distal point (1708) and most proximal point (1704) of the catheter model (1001). The shift in the dx component (2303) corresponds with the axis of the basket length (2300) of the catheter model (1001). The shift in the dy component (2304) corresponds with the axis of the basket width (2301) of the catheter model (1001).

The shift event (2302) may be accomplished by user entry of relevant starting point (2307) for initiating the shift event (2302) and any other data entry required to achieve the shift event (2302) including entry of dx, dy and/or dz distance units to achieve a shift in the catheter model (1001) and/or a rotational tilt (e.g. 3-D space) in order to identify and view remote rotational sources on the 2-D grid. User entry of data may also include entry of target spline (1008) and/or sensor (1002) points the user is shifting and/or rotating the model from. This data entry may include starting spline and/or sensors points, the number of splines (1008) and/or sensor (1002) points the user seeks to shift to in a particular direction, the actual identification of the letter spline (1008) and/or number of the sensor (1002) point the user to the goal endpoint (2307) for accomplishing the shift event (2302) and/or rotational tilt of the catheter model (1001).

Each of dx, dy and/or dz indicates a shift in discrete units of one or more of the three axes in 3-dimensional space, x, y and z. These distance units are implemented in accordance with the methods described in greater detail hereinbelow in FIG. 24.

A mouse drag event (2302) as described may also initiate an event that shifts the 3-D model (1001) or accomplishes a rotational tilt of the model (1001) using a click and drag feature of a mouse, for example, or any other portable input device with click and drag or similar feature. The user will select starting point (2307) and drag the mouse to endpoint (2307) so that a shift and/or rotational tilt of the model (1001) in either the x, y and/or z direction(s) is achieved.

Figure 24:
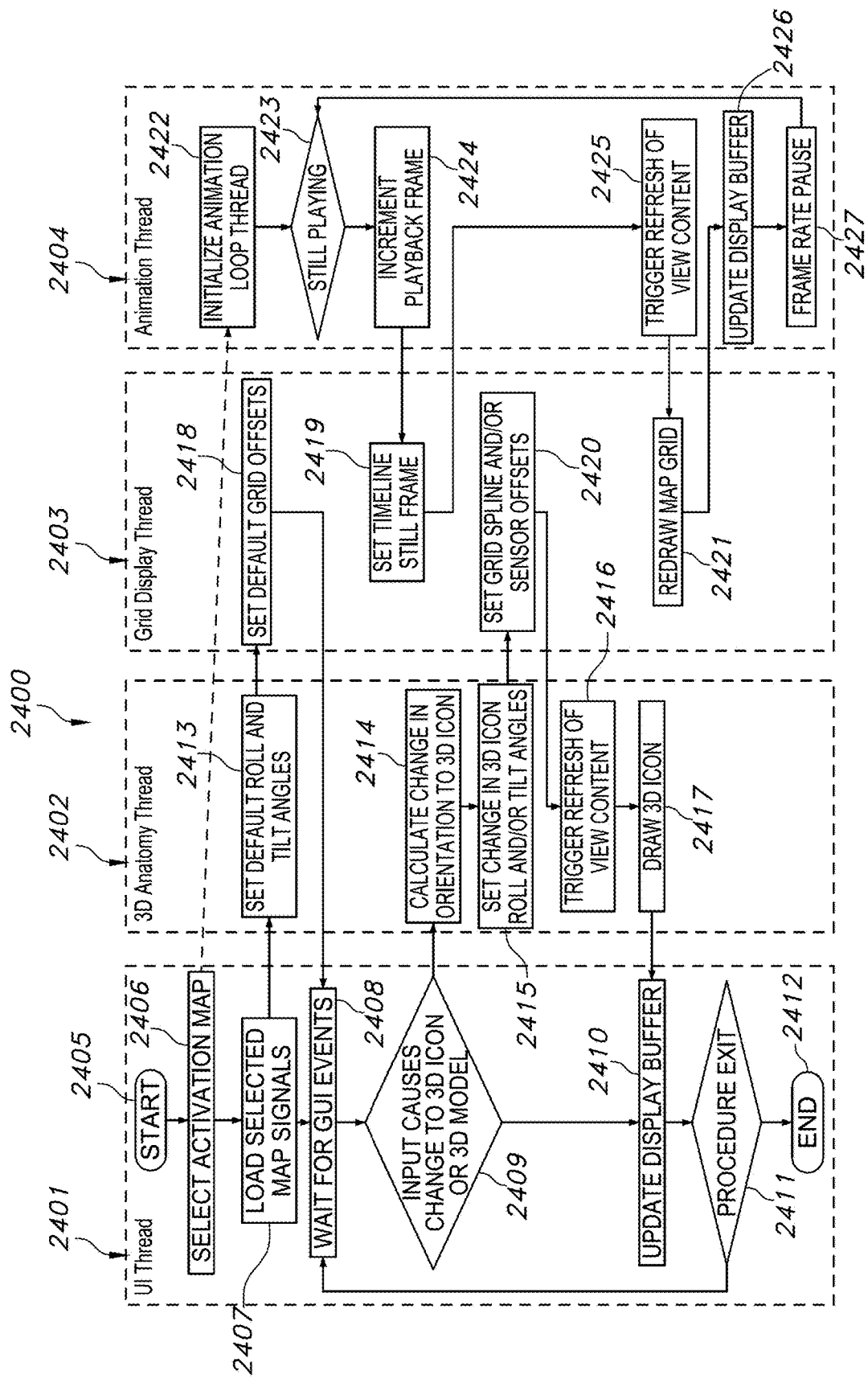
FIG. 24 is a flowchart that illustrates an example method of identifying a rotational source of a cardiac rhythm disorder by applying spline-sensor offsets to catheter model using methods illustrated in FIG. 13, FIG. 18 and FIG. 23.

FIG. 24 is a flowchart that illustrates an example method (2400) of identifying a rotational source of a cardiac rhythm disorder by applying spline-sensor offsets to catheter model using methods illustrated in at least FIG. 13, FIG. 18 and/or FIG. 23. The example method can be performed by the computing system (2500) described hereinbelow, and in greater detail with reference to FIG. 25.

More specifically, the example method (2400) implements four shown simultaneous methods including a user interface thread (2401), a 3D anatomy model thread (2402), a grid display thread (2403) and an animation thread (2404).

The four simultaneous threads start at operation (2405) at which reconstructed signal data (e.g., having assigned activation onset times) associated with the rotational source (806) of a heart rhythm disorder in FIG. 8 is provided or can be accessed by the example method (2405). At operation 2406, the activation map (e.g. maps of activation onsets) is selected by the disclosed system and method, thus initiating the animation thread (2404) at operation (2422). A continuous feed of the activation map will play at operation (2423). The UI thread (2401) which asynchronously operates while each of the other three threads are functioning, next performs operation (2407), in which the thread (2401) loads the selected activation map signals. The 3D anatomy model thread (2402) is initiated at operation (2413) with the system setting default roll and/or tilt angles of the 3-D model (1001). The grid display thread (2403) initiates operation at (2418) in response to operation (2413) of the 3D anatomy model thread (2402). At operation (2418) the system sets default grid offsets of the 2-D grid model based on the activation map. The system loops back to the UI thread (2401) at operation (2408) as it awaits user interface (UI) events (for e.g. shift event or mouse drag event (2302)), as described hereinabove in FIG. 23.

At operation (2409), the determination is made whether an input causes a change to the 3-D icon or 3-D catheter model (1001). If the determination is made that a user input caused a change to the 3-D icon or 3D catheter model (1001), then the method loops back to the 3-D anatomy model thread (2402) at operation 2414. Operation 2415 sets a change in the 3D icon or 3D model based on calculated roll and tilt angles based on the spline-offset and/or spline-sensor offset calculations described hereinabove in FIG. 13 and/or FIG. 18, as applicable. The grid display thread (2403) will next set grid spline and/or sensor offsets to the grid display at operation 2420, as applicable, based on calculated roll and/or tilt angles at operation 2415. The refresh of the 3D view content is triggered at operation 2416. At operation 2417 the 3D icon is redrawn as a new icon or 3D model is redrawn, and the display buffer of the UI thread is next updated at operation (2410).

Once the determination is made at operation 2409 that a user input has not yet caused a change to the 3D icon or 3D model at operation 2409, then the method will also update the display buffer at operation 2410 of the UI thread (2401).

Simultaneously operating are the grid display thread (2403) and animation thread (2404) as these methods are asynchronously implemented. As the animation thread initiates operations at step (2422), and continuously plays the selected activation map at operation (2423), it will increment the playback frame at operation (2424) and sets the timeline for the playback of the still frame at operation (2419) of the grid display thread (2403). This step accomplishes display of activation maps on the 2D grid within a discrete time period (e.g. 2 ms) and akin to a still movie. Next, the refresh content of viewed content is refreshed at operation 2425 as the method loops back to the animation thread (2404). At operation (2421), the map grid is redrawn and the display buffer is next updated at operation (2426) to which there may be a frame rate pause at operation (2427) and the animation thread loops back to operation (2423) in a continuous playback operation.

Simultaneously functioning is the UI thread (2401) at operation 2411 checking if the procedure (2411) is completed and/or the user requested an exit, the user will exit at step (2412). If the procedure is still underway and the user is still attempting to identify for e.g., a rotational source of a cardiac rhythm disorder, such as a rotor or a remotely located rotor such as sources located in edge conditions of the heart (120) relative to the catheter subassembly (301), then the method will loop back to operation (2408) as it awaits further user interface (UI) events (2408).

It should be noted that the foregoing data that is accessed, transformed, determined and calculated can be stored (such as in computer memory or storage device) for later use in accordance with the example method 2400.

In operation, the rotational source of the heart rhythm disorder illustrated in FIG. 1, as defined according to the foregoing disclosure, can be treated in the patient's heart to eliminate the heart rhythm disorder. For example, heart tissue of the patient on or within the defined rotational path can thus be targeted for treatment. In cases where the core is identified, treatment can be targeted to heart tissue on or within the core, sparing heart tissue outside the core. In various cases, a margin beyond the rotational path or the core can be established for treatment purposes. For example, a region of heart tissue slightly larger (e.g., a millimeter or several millimeters) than the rotational path or the likely core can be targeted for treatment.

The treatment can be successfully delivered to the targeted heart tissue (rotational path or core—with/without margin) by ablation, for example. Other treatments of the targeted heart tissue are of course possible, e.g., various energy sources (including but not limited to radiofrequency, cryoenergy, microwave, and ultrasound), gene therapy, stem cell therapy, pacing stimulation, drug or other therapy.

Figure 25:
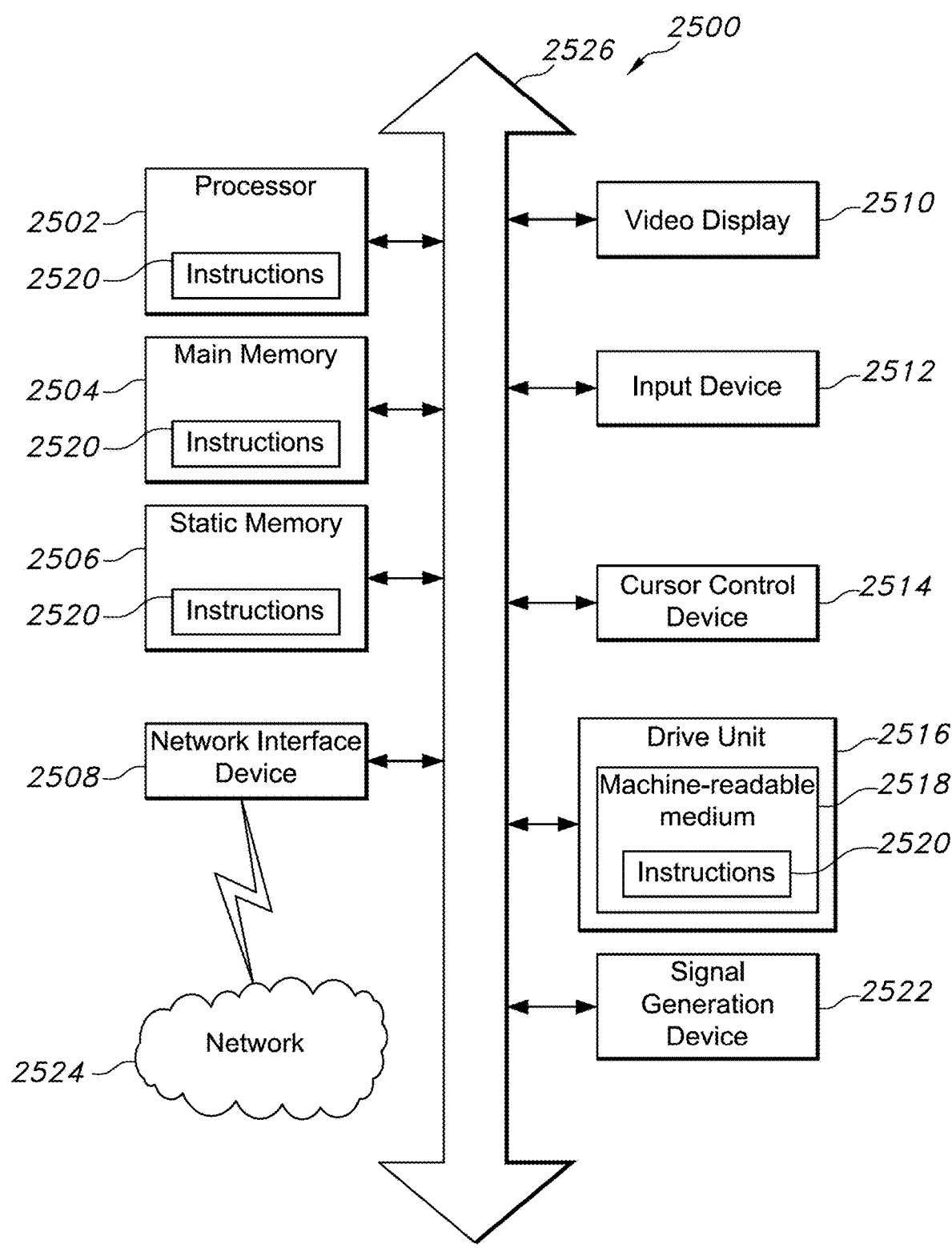
FIG. 25 is a block diagram of an illustrative embodiment of a general computing system.

FIG. 25 is a block diagram of an illustrative embodiment of a general computing system 2500. The computing system 2500 can include a set of instructions that can be executed to cause the computing system 2500 to perform any one or more of the methods or computer based functions disclosed herein. The computing system 2500, or any portion thereof, may operate as a standalone device or may be connected, e.g., using a network 2524 or other connection, to other computing systems or peripheral devices.

The computing system 2500 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computing system 2500 is illustrated, the term "system" shall also be taken to include any collection of systems or sub-systems that individually or jointly execute a set, or multiple sets, of instructions to perform one or more computer functions.

As illustrated in FIG. 25, the computing system 2500 may include a processor 2502, e.g., a central processing unit (CPU), a graphics-processing unit (GPU), or both. Moreover, the computing system 2500 may include a main memory 2504 and a static memory 2506 that can communicate with each other via a bus 2526. As shown, the computing system 2500 may further include a video display unit 2510, such as a liquid crystal display (LCD), an organic light emitting diode (OLED), a flat panel display, a solid state display, or a cathode ray tube (CRT). Additionally, the computing system 2500 may include an input device 2512, such as a keyboard, and a cursor control device 2514, such as a mouse. The computing system 2500 can also include a disk drive unit 2516, a signal generation device 2522, such as a speaker or remote control, and a network interface device 2508.

In a particular embodiment or aspect, as depicted in FIG. 25, the disk drive unit 2516 may include a machine-readable or computer-readable medium 2518 in which one or more sets of instructions 2520, e.g., software, can be embedded, encoded or stored. Further, the instructions 2520 may embody one or more of the methods or logic as described herein. In a particular embodiment or aspect, the instructions 2520 may reside completely, or at least partially, within the main memory 2504, the static memory 2506, and/or within the processor 2502 during execution by the computing system 2500. The main memory 2504 and the processor 2502 also may include computer-readable media.

In an alternative embodiment or aspect, dedicated hardware implementations, such as application specific integrated circuits, programmable logic arrays and other hardware devices, can be constructed to implement one or more of the methods described herein. Applications that may include the apparatus and systems of various embodiments or aspects can broadly include a variety of electronic and computing systems. One or more embodiments or aspects described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments or aspects, the methods described herein may be implemented by software programs tangibly embodied in a processor-readable medium and may be executed by a processor. Further, in an exemplary, non-limited embodiment or aspect, implementations can include distributed processing, component/object distributed processing, and parallel processing. Alternatively, virtual computing system processing can be constructed to implement one or more of the methods or functionality as described herein.

It is also contemplated that a computer-readable medium includes instructions 2520 or receives and executes instructions 2520 responsive to a propagated signal, so that a device connected to a network 2524 can communicate voice, video or data over the network 2524. Further, the instructions 2520 may be transmitted or received over the network 2524 via the network interface device 2508.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any tangible medium that is capable of storing or encoding a set of instructions for execution by a processor or that cause a computing system to perform any one or more of the methods or operations disclosed herein.

In a particular non-limiting, example embodiment or aspect, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture and store carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments or aspects, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Thus, a system and method to define a rational source associated with a biological rhythm disorder, such a heart rhythm disorder, has been described herein. Although specific example embodiments or aspects have been described, it will be evident that various modifications and changes may be made to these embodiments or aspects without departing from the broader scope of the invention. Accordingly, the specification and drawings are to be regarded in an illustrative rather than a restrictive sense. The accompanying drawings that form a part hereof, show by way of illustration, and not of limitation, specific embodiments or aspects in which the subject matter may be practiced. The embodiments or aspects illustrated are described in sufficient detail to enable those skilled in the art to practice the teachings disclosed herein. Other embodiments or aspects may be utilized and derived therefrom, such that structural and logical substitutions and changes may be made without departing from the scope of this disclosure. This Detailed Description, therefore, is not to be taken in a limiting sense, and the scope of various embodiments or aspects is defined only by the appended claims, along with the full range of equivalents to which such claims are entitled.

Such embodiments or aspects of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or aspects have been illustrated and described herein, it should be appreciated that any arrangement calculated to achieve the same purpose may be substituted for the specific embodiments or aspects shown. This disclosure is intended to cover any and all adaptations or variations of various embodiments or aspects. Combinations of the above embodiments or aspects, and other embodiments or aspects not specifically described herein, will be apparent to those of skill in the art upon reviewing the above description.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments or aspects, various features are grouped together in a single embodiment for the purpose of streamlining the disclosure. This method of disclosure is not to be interpreted as reflecting that the claimed embodiments or aspects have more features than are expressly recited in each claim. Rather, as the following claims reflect, inventive subject matter lies in less than all features of a single disclosed embodiment or aspect. Thus, the following claims are hereby incorporated into the Detailed Description, with each claim standing on its own as a separate example embodiment or aspect. It is contemplated that various embodiments or aspects described herein can be combined or grouped in different combinations that are not expressly noted in the Detailed Description. Moreover, it is further contemplated that claims covering such different combinations can similarly stand on their own as separate example embodiments or aspects, which can be incorporated into the Detailed Description.

What is claimed is:

1. A system associated with identifying a remote or polar source associated with a cardiac rhythm disorder, the system comprising:
   a plurality of sensors of a catheter, the sensors adapted to be located at multiple locations in relation to a heart to sense cardiac information signals; and
   a processor interfacing with the plurality of sensors, wherein the processor is configured to:
   receive the cardiac information signals from the sensors of the catheter associated with the heart during the cardiac rhythm disorder;
   generate a representation using the cardiac information signals received from the sensors by transformation of spline-sensor locations of the catheter to x-y coordinate pairs of locations;
   determine a first offset resulting from a perturbation to corresponding x-y coordinate pairs of locations associated with the representation, the first offset displacing coordinate pairs of sensor locations of the representation at least one unit of displacement in a first direction; and
   identify the remote or polar source associated with the cardiac rhythm disorder when activations associated with the cardiac information signals rotate in sequence at least once, or emanate centrifugally for at least a first time period, the source being identified based on the representation as displaced.

2. The system of claim 1, wherein the processor is further configured to determine a second offset of corresponding coordinate pairs of locations of the representation in one or more second units of displacements in at least one direction, in identifying one or more remote sources.

3. The system of claim 1, wherein the unit of displacement includes at least one of an angle between splines, spline-sensor offset, a spline offset, a sensor offset, and an angle of tilt.

4. The system of claim 3, wherein the perturbation associated with the representation includes displacing the coordinate pairs of locations in one or more units of displacement in two or more directions, the unit of displacement being above a threshold.

5. The system of claim 4, wherein at least one source of the cardiac rhythm disorder is a remote source relative to the sensors or the catheter.

6. The system of claim 1, wherein the processor is further configured to determine an angle of tilt above a threshold, the perturbation displacing coordinate pairs of locations of the representation in two or more directions in order to identify one or more sources of the cardiac rhythm disorder.

7. The system of claim 1, wherein the processor is further configured to:
   determine an approximate location of the source based on sensor locations associated with the cardiac information signals that rotate in sequence at least once, or emanate centrifugally for at least a first time period using transformed spline-sensor (x-y) coordinate points of the representation.

8. The system of claim 1, wherein the processor is further configured to:
   determine an approximate location of the source using a polygon based on coordinate pairs of sensor locations bounding at least one source.

9. The system of claim 8, wherein the processor is further configured to generate the polygon based on three or more co-located positional vertices bounding the source as the source rotates or emanates centrifugally for one or more time periods on or near the polygon.

10. The system of claim 9, wherein the processor is further configured to determine a likely core associated with at least one rotational or centrifugal path based on the polygon bounding the rotational or centrifugal path for at least one time period.

11. The system of claim 8, wherein the processor is further configured to identify at least one continuous rotational or centrifugal path of one or more sources located near or within the polygon bounding the source.

12. The system of claim 1, wherein the processor is further configured to:
   detect an angular tilt associated with coordinate pairs of sensors of the catheter model;
   calculate at least one spline-sensor translation of the plurality of spline-sensor references to x-y coordinate points based on the angular tilt displacing the representation; and
   determine a path of a rotational or centrifugal source using positional vertices bounding the source in a polygon as it rotates or emanates centrifugally for one or more time periods on or near the polygon.

13. The system of claim 12, wherein the translation of the at least one spline-sensor comprises the processor being further configured to:
   detect the angle between two splines of the catheter as indicated in the representation;
   calculate the translated sensor-spline value using: the tilt angle formed between the original axis of the representation and the representation once tilted and the detected angle between two splines; and apply the translated sensor-spline value to a transformed x-y coordinate representation of the cardiac information signals.

14. The system of claim 1, wherein the processor is further configured to identify a remotely located rotational or centrifugal source relative to the representation by applying one or more offsets to the representation in one or more units of displacement as determined, the remotely located rotational or centrifugal source being displaced within grid boundaries of the representation.

15. The system of claim 14, further comprising the processor being configured to determine an origin of the spline-sensor location(s) the representation is fragmented into a panoramic grid representation in order to identify the likely location of the remotely located source of the cardiac rhythm disorder.

16. The system of claim 15, further comprising the processor being configured to determine an origin of a sensor location the representation is fragmented into the panoramic grid representation in order to identify the likely location of a remote source located at or near a polar region of the heart relative to the representation.

17. A system associated with identifying a remote source associated with a biological rhythm disorder, the system comprising:
a plurality of sensors of a catheter adapted to be located at multiple locations in relation to an organ to sense biological information signals; and
a processor interfacing with the plurality of sensors, wherein the processor is configured to:
receive biological information signals from the sensors of the catheter associated with a patient's organ during the biological rhythm disorder;
generate a representation using the biological information signals received from the sensors by transformation of spline-sensor locations of the catheter to x-y coordinate pairs of locations;
determine a first offset resulting from a perturbation to corresponding x-y coordinate pairs of locations associated with the representation, the first offset displacing coordinate pairs of sensor locations of the representation at least one unit of displacement in a first direction; and
identify the remote source associated with the biological rhythm disorder when activations associated with the biological information signals rotate in sequence at least once, or emanate centrifugally for at least a first time period, the source being identified based on the representation as displaced.

18. A non-transitory computer readable medium comprising instructions that when executed by a computing device perform operations that include:
receiving cardiac information signals from sensors of a catheter associated with a patient's heart during the cardiac rhythm disorder;
generating a representation using the cardiac information signals received from the sensors by transformation of spline-sensor locations of the catheter to x-y coordinate pairs of locations;
determining a first offset resulting from a perturbation to corresponding x-y coordinate pairs of locations associated with the representation, the first offset displacing coordinate pairs of sensor locations of the representation at least one unit of displacement in a first direction; and
identifying a remote or polar source associated with the cardiac rhythm disorder when activations associated with the cardiac information signals rotate in sequence at least once, or emanate centrifugally for at least a first time period, the source being identified based on the representation as displaced.

19. A method of identifying a remote or polar source associated with a cardiac rhythm disorder, the method comprising:
receiving cardiac information signals from sensors of a catheter associated with a patient's heart during the cardiac rhythm disorder;
generating a representation using the cardiac information signals received from the sensors by transformation of spline-sensor locations of the catheter to x-y coordinate pairs of locations;
determining a first offset resulting from a perturbation to corresponding x-y coordinate pairs of locations associated with the representation, the first offset displacing coordinate pairs of sensor locations of the representation at least one unit of displacement in a first direction; and
identifying the remote or polar source associated with the cardiac rhythm disorder when activations associated with the cardiac information signals rotate in sequence at least once, or emanate centrifugally for at least a first time period, the source being identified based on the representation as displaced.

20. The method of claim 19, wherein the method further comprises determining a second offset of corresponding coordinate pairs of locations of the representation in one or more second units of displacements in at least one direction, in identifying one or more remote sources.

21. The method of claim 19, wherein the unit of displacement includes at least one of an angle between splines, spline-sensor offset, a spline offset, a sensor offset, and an angle of tilt.

22. The method of claim 21, wherein the perturbation associated with the representation includes displacing the coordinate pairs of locations in one or more units of displacement in two or more directions, the unit of displacement being above a threshold.

23. The method of claim 22, wherein at least one source of the cardiac rhythm disorder is a remote source relative to the sensors or the catheter.

24. The method of claim 19, wherein the method further comprises determining an angle of tilt above a threshold, the perturbation displacing coordinate pairs of locations of the representation in two or more directions in order to identify one or more sources of the cardiac rhythm disorder.

25. The method of claim 19, wherein the method further comprises:
determining an approximate location of the source based on sensor locations associated with the cardiac information signals that rotate in sequence at least once, or emanate centrifugally for at least a first time period using transformed spline-sensor (x-y) coordinate points of the representation.

26. The method of claim 19, wherein the method further comprises:
determining an approximate location of the source based on a polygon formed of coordinate pairs of sensor locations bounding at least one source.

27. The method of claim 26, wherein the polygon is formed by three or more co-located positional vertices bounding the source as the source rotates or emanates centrifugally for one or more time periods on or near the polygon.

28. The method of claim 27, wherein the method further comprises determining a likely core associated with at least one rotational or centrifugal path based on the polygon bounding the rotational or centrifugal path for at least one time period.

29. The method of claim 26, wherein the method further comprises identifying at least one continuous rotational or centrifugal path of one or more sources located near or within the polygon bounding the source.

30. The method of claim 19, wherein the method further comprises:
   detecting an angular tilt associated with coordinate pairs of sensors of the catheter model;
   calculating at least one spline-sensor translation of the plurality of spline-sensor references to x-y coordinate points based on the angular tilt displacing the representation; and
   determining a path of a rotational or centrifugal source using positional vertices bounding the source in a polygon as it rotates or emanates centrifugally for one or more time periods on or near the polygon.

31. The method of claim 30, wherein translation of the at least one spline-sensor comprises:
   detecting the angle between two splines of the catheter as indicated in the representation;
   calculating the translated sensor-spline value using: the tilt angle formed between the original axis of the representation and the representation once tilted and the detected angle between two splines; and
   applying the translated sensor-spline value to a transformed x-y coordinate representation of the cardiac information signals.

32. The method of claim 19, wherein the method further comprises identifying a remotely located rotational or centrifugal source relative to the representation by applying one or more offsets to the representation in one or more units of displacement as determined, the remotely located rotational or centrifugal source being displaced within grid boundaries of the representation.

33. The method of claim 32, further comprising determining an origin of the spline-sensor location(s) the representation is fragmented into a panoramic grid representation in order to identify the likely location of the remotely located source of the cardiac rhythm disorder.

34. The method of claim 33, further comprising determining an origin of a sensor location the representation is fragmented into the panoramic grid representation in order to identify the likely location of a remote source located at or near a polar region of the heart relative to the representation.

35. A method of identifying a remote or polar source associated with a biological rhythm disorder, the method comprising:
   receiving biological information signals from sensors of a catheter associated with a patient's organ during the biological rhythm disorder;
   generating a representation using the biological information signals received from the sensors by transformation of spline-sensor locations of the catheter to x-y coordinate pairs of locations;
   determining a first offset resulting from a perturbation to corresponding x-y coordinate pairs of locations associated with the representation, the first offset displacing coordinate pairs of sensor locations of the representation at least one unit of displacement in a first direction; and
   identifying the remote or polar source associated with the biological rhythm disorder when activations associated with the biological information signals rotate in sequence at least once, or emanate centrifugally for at least a first time period, the source being identified based on the representation as displaced.

* * * * *